US011980434B2

United States Patent
Rabindran et al.

(10) Patent No.: US 11,980,434 B2
(45) Date of Patent: May 14, 2024

(54) SYSTEMS AND METHODS FOR CONTROL OF END EFFECTORS

(71) Applicant: INTUITIVE SURGICAL OPERATIONS, INC., Sunnyvale, CA (US)

(72) Inventors: Dinesh Rabindran, San Jose, CA (US); Ryan C. Abbott, San Jose, CA (US); Daniel H. Gomez, Los Gatos, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 877 days.

(21) Appl. No.: 16/971,277

(22) PCT Filed: Feb. 19, 2019

(86) PCT No.: PCT/US2019/018648
§ 371 (c)(1),
(2) Date: Aug. 19, 2020

(87) PCT Pub. No.: WO2019/164856
PCT Pub. Date: Aug. 29, 2019

(65) Prior Publication Data
US 2021/0052340 A1 Feb. 25, 2021

Related U.S. Application Data

(60) Provisional application No. 62/632,841, filed on Feb. 20, 2018.

(51) Int. Cl.
*A61B 18/12* (2006.01)
*A61B 17/29* (2006.01)
(Continued)

(52) U.S. Cl.
CPC .......... *A61B 34/35* (2016.02); *A61B 17/2909* (2013.01); *A61B 17/3201* (2013.01);
(Continued)

(58) Field of Classification Search
CPC ......... A61B 34/35; A61B 34/37; A61B 34/71; A61B 2034/301; A61B 18/1445
See application file for complete search history.

(56) References Cited

U.S. PATENT DOCUMENTS

| 8,623,044 B2 | 1/2014 | Timm et al. |
| 8,888,688 B2 | 11/2014 | Julian et al. |

(Continued)

FOREIGN PATENT DOCUMENTS

| WO | WO-2015142290 A1 | 9/2015 |
| WO | WO-2016043845 A1 | 3/2016 |

(Continued)

OTHER PUBLICATIONS

International Search Report and Written Opinion for Application No. PCT/US2019/018648, dated Jun. 5, 2019, 10 pages.
(Continued)

*Primary Examiner* — Daniel W Fowler
(74) *Attorney, Agent, or Firm* — Artegis Law Group, LLP

(57) ABSTRACT

A system and method of controlling an end effector includes a drive unit having a first actuator and a second actuator, a moveable platform drivably coupled to the first actuator, first and second engagement members drivably coupled to the second actuator; and a control unit. The control unit is configured to actuate the first actuator to drive the platform, detect engagement of the first engagement member with a third engagement member of an instrument, detect engagement of the second engagement member with a fourth engagement member of the instrument, and actuate the second actuator to drive the first and second engagement
(Continued)

members. Movement of the third and engagement member causes movement of a degree of freedom of an end effector of the instrument in a first direction. Movement of the fourth engagement member causes movement of the degree of freedom in a second direction opposite the first direction.

21 Claims, 22 Drawing Sheets

(51) Int. Cl.
*A61B 17/3201* (2006.01)
*A61B 18/14* (2006.01)
*A61B 34/00* (2016.01)
*A61B 34/35* (2016.01)
*A61B 34/37* (2016.01)
*A61B 90/00* (2016.01)
*B25J 9/10* (2006.01)
*B25J 9/16* (2006.01)
*B25J 13/08* (2006.01)
*A61B 17/34* (2006.01)
*A61B 18/00* (2006.01)
*A61B 34/30* (2016.01)

(52) U.S. Cl.
CPC .......... *A61B 18/1445* (2013.01); *A61B 34/37* (2016.02); *A61B 34/71* (2016.02); *A61B 90/06* (2016.02); *B25J 9/104* (2013.01); *B25J 9/1633* (2013.01); *B25J 9/1641* (2013.01); *B25J 13/085* (2013.01); *A61B 17/3421* (2013.01); *A61B 2018/00595* (2013.01); *A61B 2034/301* (2016.02); *A61B 2090/064* (2016.02); *A61B 2090/066* (2016.02)

(56) References Cited

U.S. PATENT DOCUMENTS

| | | | |
|---|---|---|---|
| 9,101,379 | B2 | 8/2015 | Au et al. |
| 11,020,192 | B2 | 6/2021 | Abbott et al. |
| 2006/0052664 | A1* | 3/2006 | Julian ................ A61B 1/0053 600/152 |
| 2010/0168559 | A1* | 7/2010 | Tegg ................ A61M 25/0054 604/523 |
| 2011/0213384 | A1 | 9/2011 | Jeong |
| 2011/0270046 | A1* | 11/2011 | Paul .................... A61B 5/68 604/533 |
| 2013/0060278 | A1* | 3/2013 | Bozung .............. A61B 17/1675 606/205 |
| 2013/0172906 | A1 | 7/2013 | Olson et al. |
| 2014/0276078 | A1* | 9/2014 | Schweitzer .......... A61B 5/283 600/459 |
| 2015/0112363 | A1 | 4/2015 | Steege et al. |
| 2016/0030121 | A1* | 2/2016 | Inoue ................... A61B 34/70 606/130 |
| 2016/0239525 | A1 | 8/2016 | Treves et al. |
| 2016/0303743 | A1 | 10/2016 | Rockrohr |
| 2017/0020615 | A1 | 1/2017 | Koenig et al. |
| 2017/0143436 | A1* | 5/2017 | Lathrop ............... A61B 34/30 |
| 2017/0165009 | A1 | 6/2017 | Chaplin et al. |
| 2017/0231653 | A1 | 8/2017 | Kapadia |
| 2018/0153628 | A1* | 6/2018 | Grover ................ A61B 34/71 |
| 2018/0214219 | A1* | 8/2018 | Overmyer ........ A61B 17/00234 |
| 2018/0243035 | A1* | 8/2018 | Kopp ................... A61B 34/25 |
| 2019/0175294 | A1 | 6/2019 | Abbott et al. |
| 2019/0192245 | A1 | 6/2019 | Abbott et al. |
| 2019/0357988 | A1 | 11/2019 | Abbott |
| 2020/0275984 | A1 | 9/2020 | Brisson et al. |

FOREIGN PATENT DOCUMENTS

| | | |
|---|---|---|
| WO | WO-2016081286 A1 | 5/2016 |
| WO | WO-2016137611 A1 | 9/2016 |
| WO | WO-2016144937 A1 | 9/2016 |
| WO | WO-2016144998 A1 | 9/2016 |
| WO | WO-2016181432 A1 | 11/2016 |
| WO | WO-2016183054 A1 | 11/2016 |
| WO | WO-2016189284 A1 | 12/2016 |
| WO | WO-2016196238 A1 | 12/2016 |
| WO | WO-2016205452 A1 | 12/2016 |
| WO | WO-2017053358 A1 | 3/2017 |
| WO | WO-2017098264 A1 | 6/2017 |
| WO | WO-2018039459 A1 | 3/2018 |
| WO | WO-2018053305 A1 | 3/2018 |
| WO | WO-2018148030 A1 | 8/2018 |

OTHER PUBLICATIONS

Liang Y., et al., "A Novel Position Compensation Scheme for Cable-pulley Mechanisms used in Laparoscopic Surgical Robots," Sensors, 2017, vol. 17 (2257), pp. 1-17.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP19757192 dated Mar. 2, 2021, 6 pages.

Extended European Search Report for Application No. EP24152863. 7, mailed on Feb. 12, 2024, 06 pages.

* cited by examiner

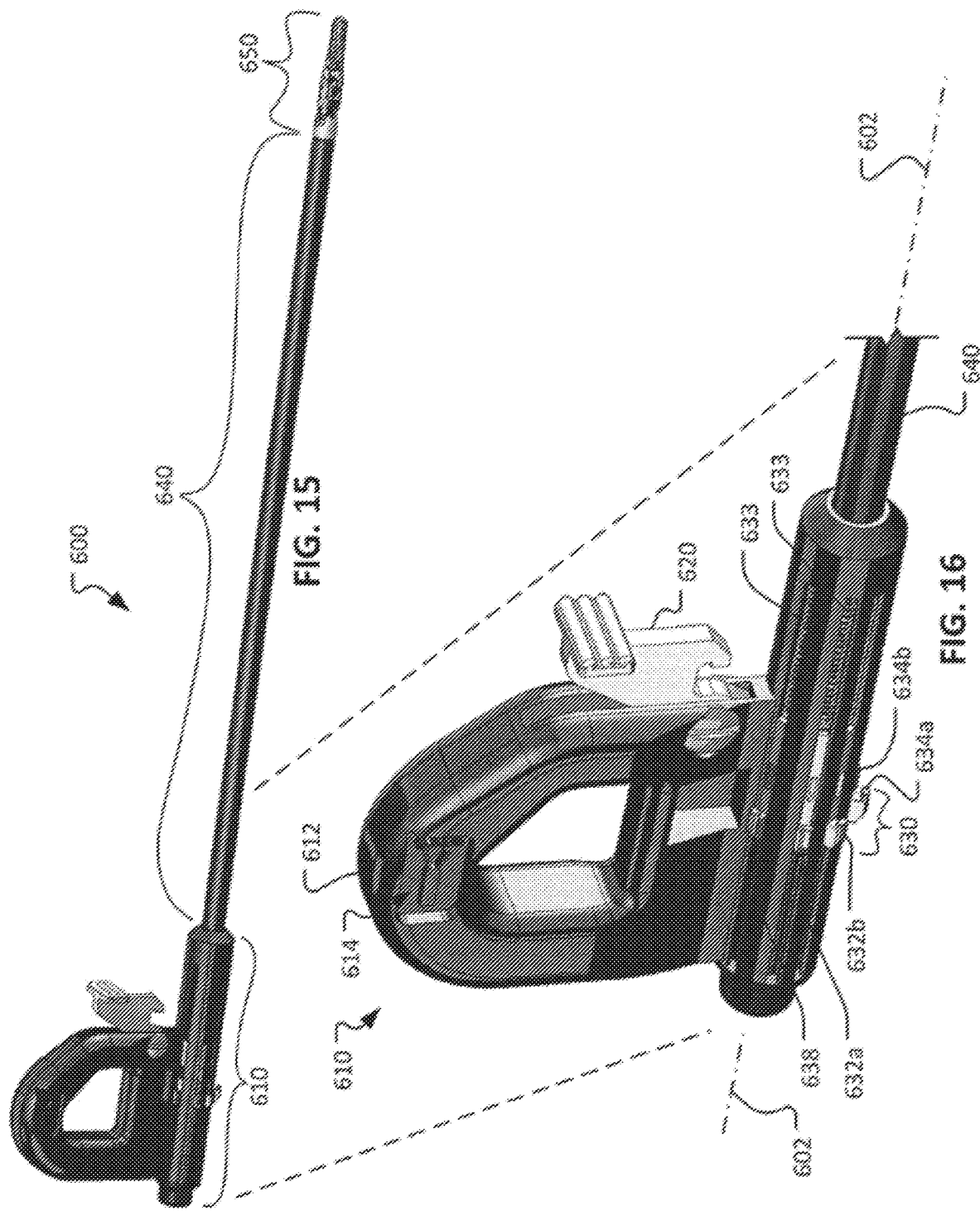

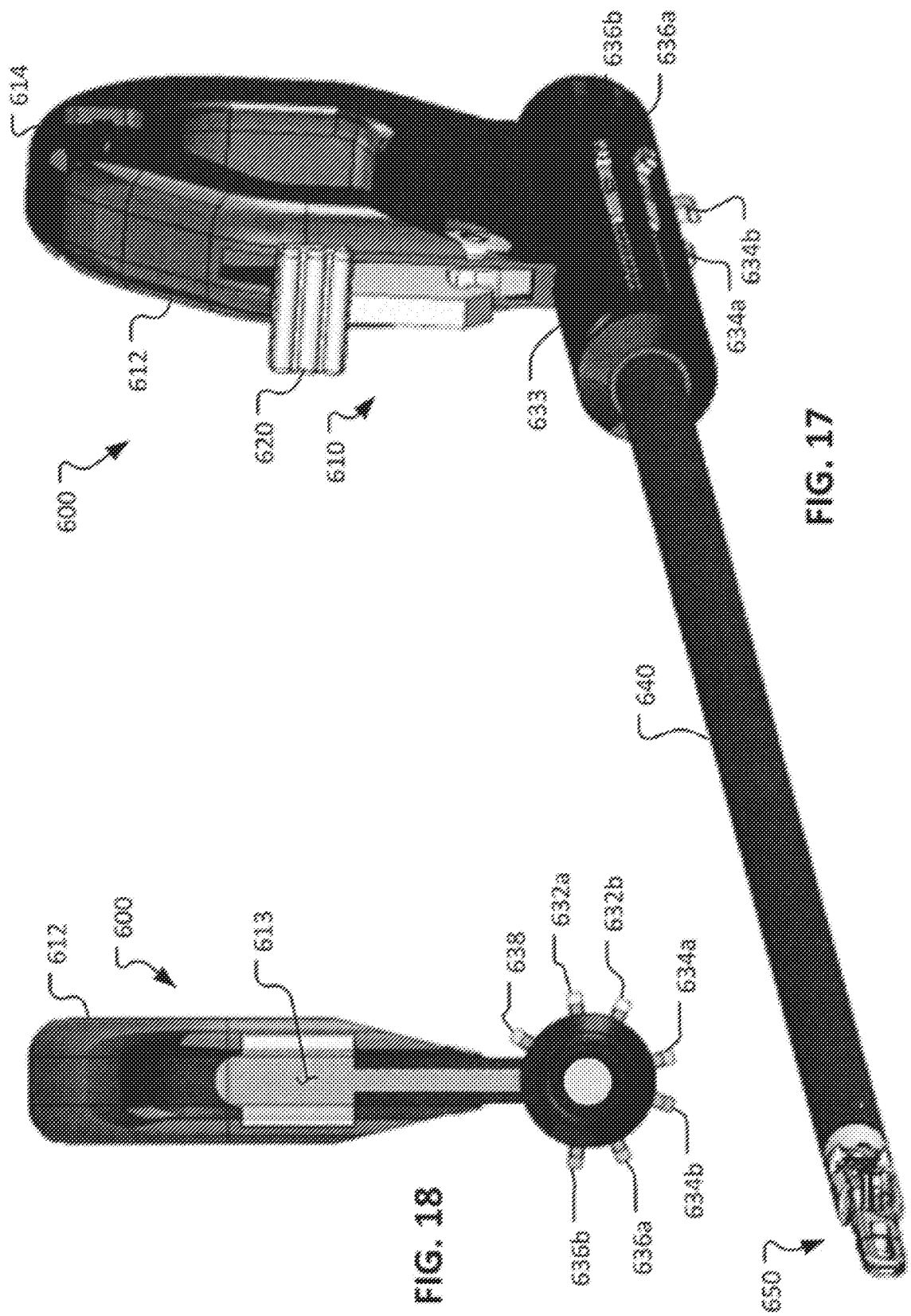

SYSTEMS AND METHODS FOR CONTROL OF END EFFECTORS

RELATED APPLICATIONS

This application is a U.S. National Stage patent application of International Patent Application No. PCT/US2019/018648, filed on Feb. 19, 2019, the benefit of which is claimed, and claims priority to and benefit of U.S. Provisional Patent Application No. 62/632,841, filed Feb. 20, 2018 and entitled "Systems and Methods for Control of End Effectors," each of which is incorporated by reference herein in its entirety.

TECHNICAL FIELD

The present disclosure relates generally to control of end effectors and more particularly to assisting with the engagement between actuators and degrees of freedom in the end effectors and the homing of the degrees of freedom.

BACKGROUND

Computer-assisted devices often include multiple movable manipulators operable to manipulate instruments for performing a task at a work site. The computer-assisted devices can include at least one movable manipulator for supporting an image capturing device that captures images of the work site. A movable manipulator can include interconnected links that are coupled together by one or more actively controlled joints. The manipulator can include one or more passive joints that are not actively controlled and comply with movement of an actively controlled joint.

The computer-assisted devices can include industrial and recreational systems, and also medical robotic systems used in procedures for diagnosis, cosmetics, therapeutics, non-surgical treatment, surgical treatment, etc. As a specific example, computer-assisted devices include minimally invasive, computer-assisted, telesurgical systems that allow a surgeon to operate on a patient from bedside or a remote location. Telesurgery is a general term for surgical systems in which the surgeon, rather than directly holding and moving all parts of the instruments by hand, uses some form of indirect or remote control, e.g., a servomechanism, or the like, to manipulate surgical instrument movements. The surgical instruments for such surgical systems can be inserted through minimally invasive surgical apertures or natural orifices to treat tissues at sites within the patient, often reducing the trauma generally associated with accessing a surgical worksite by open surgery techniques.

These computer-assisted systems can move end effectors of the instruments with sufficient dexterity to perform industrial, recreational, medical (including surgical) tasks. Such tasks may pivoting shafts of the instruments, sliding of the shaft axially (such as through an aperture if applicable), rotating of the shaft (such as outside of or within an aperture if an aperture is used), and/or the like.

SUMMARY

Consistent with some embodiments, a computer-assisted device includes a drive unit including a first actuator and a second actuator; a moveable platform drivably coupled to the first actuator; a first engagement member and a second engagement member drivably coupled to the second actuator; and a control unit coupled to the drive unit. The control unit is configured to, in an engagement mode, actuate the first actuator to drive the platform, detect engagement of a first engagement member with a second engagement member of an instrument, detect engagement of a third engagement member with a fourth engagement member of the instrument, and actuate the second actuator to drive the second and fourth engagement members. Movement of the second engagement member causes a movement of an end effector of the instrument in a first direction of a degree of freedom. Movement of the fourth engagement member causes a movement of the end effector in a second direction of the degree of freedom. The second direction is opposite the first direction.

Consistent with some embodiments, a method is performed by a drive unit including a moveable platform, a first actuator, and a second actuator. The method includes actuating the first actuator to drive the platform, detecting engagement of a first engagement member with a second engagement member of an instrument, detecting engagement of a third engagement member with a fourth engagement member of the instrument, and actuating a second actuator to drive the second and third engagement members to control the degree of freedom. Movement of the second engagement member causes a movement of an end effector of the instrument in a first direction of a degree of freedom. Movement of the fourth engagement member causes a movement of the end effector in a second direction of the degree of freedom. The second direction is opposite the first direction.

Consistent with some embodiments, a computer-assisted device includes a first engagement member drivably coupled to a first actuator, a second engagement member drivably coupled to a second actuator, and a control unit coupled to the first and second actuators. The control unit is configured to engage the first engagement member with a third engagement member of an instrument, engage the second engagement member with a fourth engagement member of the instrument, actuate a degree of freedom of an end effector in a first direction to a first detectable position, actuate the degree of freedom in a second direction opposite the first direction to a second detectable position, and actuate the degree of freedom to a third position between the first detectable position and the second detectable position. A movement of the third engagement member causes movement of a degree of freedom of an end effector of the instrument in a first direction. A movement of the fourth engagement member causes movement of the degree of freedom in a second direction opposite the first direction.

Consistent with some embodiments, a computer-assisted device includes a drive unit including a first actuator and a second actuator, a first engagement member drivably coupled to the first actuator, a second engagement member drivably coupled to the second actuator, and a control unit coupled to the drive unit. The control unit is configured to, in an engagement mode, actuate the first actuator to drive the first engagement member, detect engagement of the first engagement member with a third engagement member of an instrument, actuate the second actuator to drive the second engagement member, and detect engagement of the second engagement member with a fourth engagement member of the instrument. A movement of the third engagement member causes a movement of an end effector of the instrument in a first direction of a degree of freedom. A movement of the fourth engagement member causes a movement of the end effector in a second direction of the degree of freedom, the second direction being opposite the first direction.

Consistent with some embodiments, a method of engaging a drive unit with an instrument includes actuating a first actuator of the drive unit to drive a first engagement member, detecting engagement of the first engagement member with a third engagement member of the instrument, actuating a second actuator of the drive unit to drive a second engagement member, and detecting engagement of the second engagement member with a fourth engagement member of the instrument. Actuation of the third engagement member causes a movement of a degree of freedom of an end effector of the instrument in a first direction. Actuation of the fourth engagement member causes a movement of the degree of freedom in a second direction opposite the first direction.

Consistent with some embodiments, a non-transitory machine-readable medium including a plurality of machine-readable instructions which when executed by one or more processors associated with a control unit are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 15 is a perspective view of an example instrument that is configured in accordance with the schematic diagram of FIGS. 9A and 9B.

FIG. 16 is a perspective view of a proximal end portion of the instrument of FIG. 15.

FIG. 17 is another perspective view of the instrument of FIG. 15.

FIG. 18 is a proximal end view of the instrument of FIG. 15.

Figure 1A:
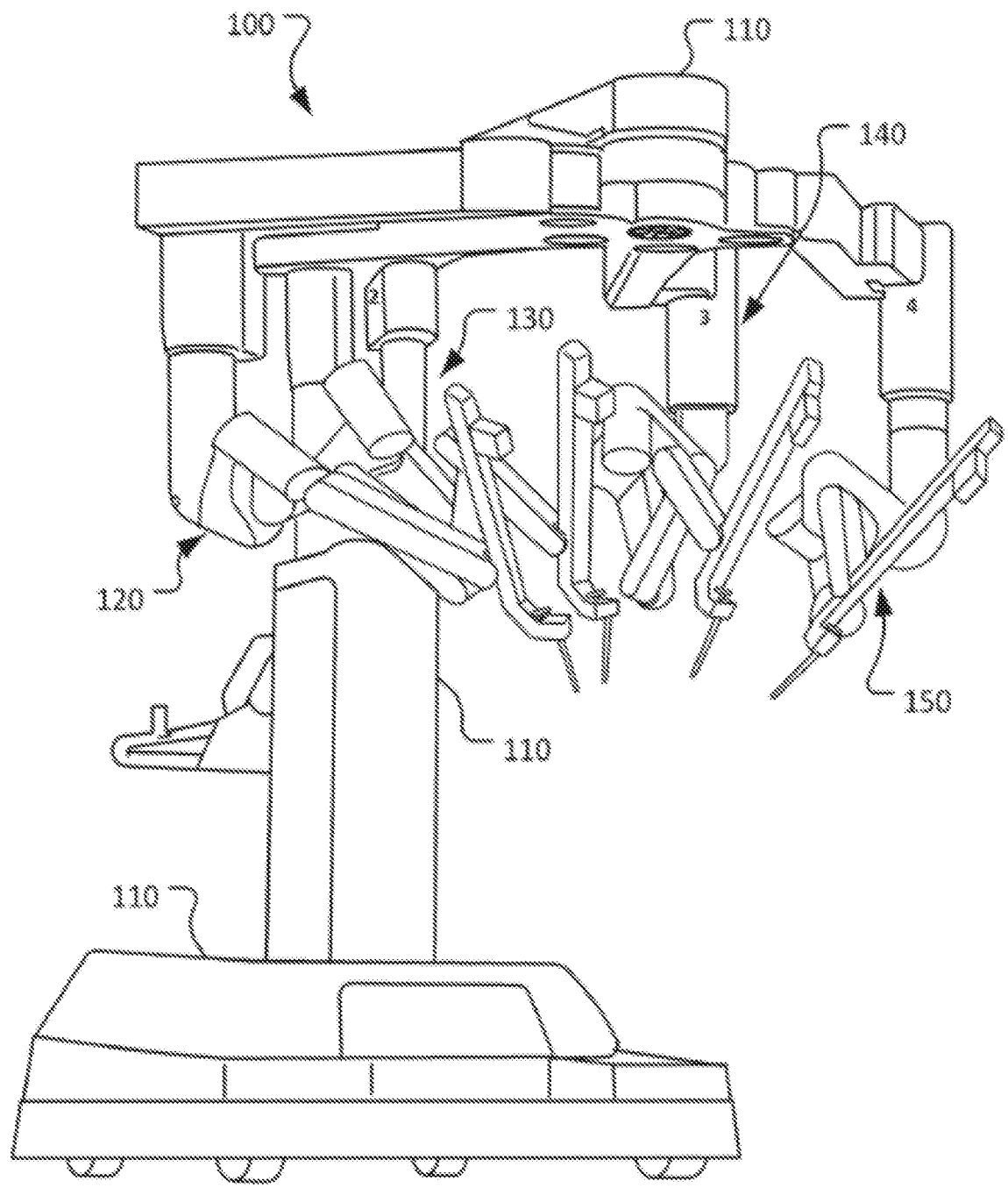
FIG. 1A is a perspective view of an example patient-side computer-assisted teleoperated system.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of the devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the device and "distal" refers to a direction away from the base.

As used herein, the term "estimate" refers to a direct measurement, or a computed quantity based on a mathematical model, or a combination of a direct measurement and a computed quantity based on a sensor fusion technique.

Aspects of the invention are described primarily in terms of an implementation using a da Vinci® Surgical System commercialized by Intuitive Surgical, Inc. of Sunnyvale, California Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, any reference to surgical instruments and surgical methods is non-limiting as the instruments, systems, and methods described herein may be used for animals, human cadavers, animal cadavers, portions of human or animal anatomy, tissue removed from human or animal anatomies (without return to a human or animal anatomy), non-surgical diagnosis, industrial systems, and general robotic or teleoperated systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

A computer-assisted teleoperated system includes one or more drive systems to control a position of an instrument within an environment. In some examples, a remotely controllable or otherwise teleoperated manipulator is operated to move the instrument in its entirety about the environment. In further examples, the one or more drive systems are operable to control a position of the instrument relative to the manipulator and/or to control a position of an end effector relative to a shaft of the instrument. As described herein, the one or more drive systems can be controlled in a manner to maintain tensions in tensioning members used to drive the end effector. Sensors associated with the one or more drive systems can also be used to detect conditions of the instrument, and readings from these sensors can be used to inform a user of the conditions of the instrument.

Although some of the examples described herein refer to surgical procedures or tools, or medical procedures and medical tools, the techniques disclosed apply to non-medical procedures and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

Further, although some of the examples presented in this disclosure discuss teleoperated robotic systems or remotely operable systems, the techniques disclosed are also applicable to computer-assisted systems that are directly and manually moved by operators, in part or in whole. For example, these techniques can be applied to robotic systems designed to help steady a tool held by the robotic arm while the tool is manipulated by a hand of an operator. As another example, the manipulators discussed herein may be configured to allow direct manipulation, and accept operator instruction through input directly applied to a link or a joint of the manipulator.

Example Systems

Example system are described herein with respect to FIGS. 1-27C, however, additional variations in structure and arrangements of the various elements are further described in U.S. Provisional Patent Application No. 62/379,112 filed Aug. 24, 2016 and entitled "Computer-Assisted Tele-Operated Surgery Systems and Methods", International Patent Application No. PCT/US2017/48425 filed Aug. 24, 2017 and entitled "Computer-Assisted Tele-Operated Surgery Systems and Methods", U.S. Provisional Patent Application No. 62/395,025 filed Sep. 15, 2016 and entitled "Computer-Assisted Tele-Operated Surgery Systems and Methods", International Patent Application No. PCT/US2017/51846 filed Sep. 15, 2017 and entitled "Computer-Assisted Tele-Operated Surgery Systems and Methods", and U.S. Provisional Patent Application No. 62/456,262 filed Feb. 8, 2017 and entitled "Control of Computer-Assisted Tele-Operated Surgical Systems", each of which is incorporated by reference herein.

Figure 1B:
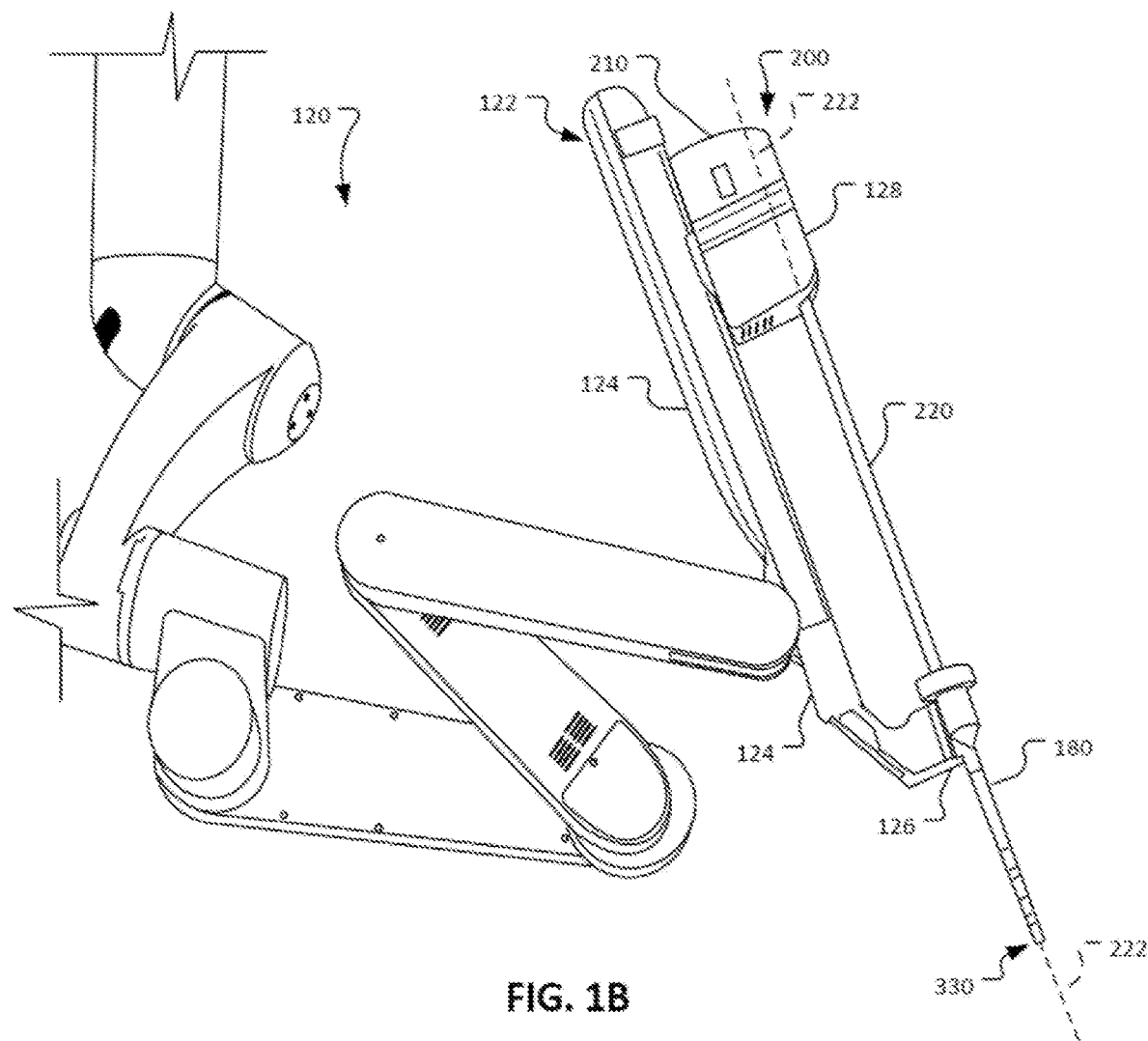
FIG. 1B is a side view of an example manipulator system of a computer-assisted teleoperated system.
Figure 2:
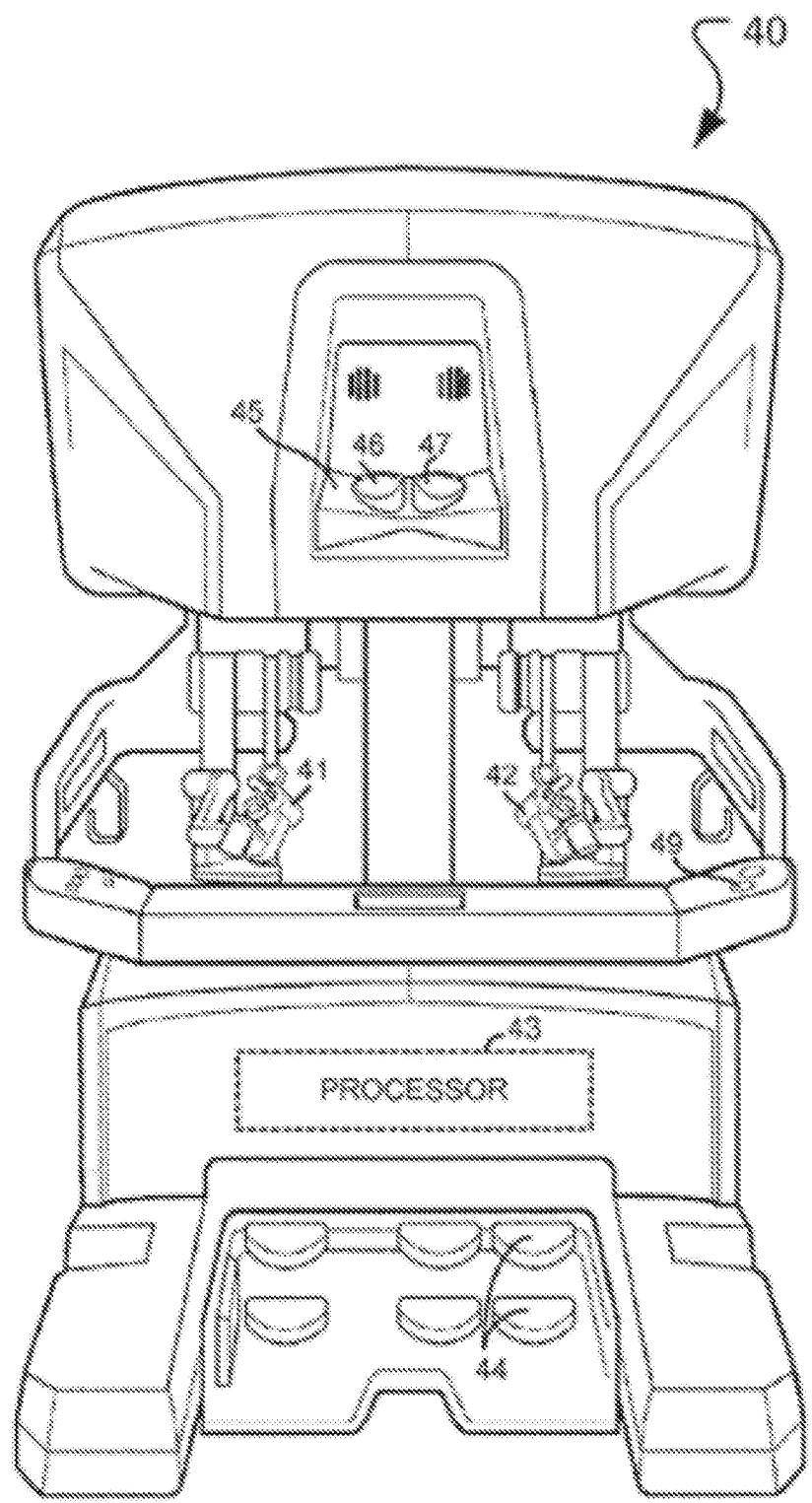
FIG. 2 is a front view of an example operator console of a computer-assisted teleoperated system.

Referring to FIGS. 1 and 2, example surgical systems for minimally invasive computer-assisted telesurgery are depicted that include a patient-side cart 100 and an operator console 40 (in this particular example, the operator console comprises an operator console that is usually used by surgical personnel such as surgeons). The patient-side cart 100 includes a base 110, a first remotely controllable manipulator system 120, a second remotely controllable manipulator system 130, a third remotely controllable manipulator system 140, and a fourth remotely controllable manipulator system 150. Each manipulator system 120, 130, 140, and 150 is pivotably coupled to the base 110. In some implementations, fewer than four or more than four remotely controllable manipulator systems may be included as part of the patient-side cart 100. While in the depicted example, the base 110 includes casters to allow ease of mobility, in some implementations, the patient-side cart 100 is fixedly mounted to a floor, ceiling, operating table, structural framework, or the like.

Many of the exemplary manipulator assemblies described herein will have more degrees of freedom (DOFs) than needed to position and move an end effector within a surgical site. For example, a surgical end effector that can be positioned with six DOFs at an internal surgical site through a minimally invasive aperture, in some implementations, has nine DOFs. These nine DOFs include, for example, six end effector DOFs, with three of these DOFs for location and three of these DOFs for orientation. These nine DOFs also include, for example, three DOFs to comply with the access site constraints. In certain implementations, additional DOFs are provided. Highly configurable manipulator assemblies having more DOFs than are needed for a given end effector position can be described as having or providing sufficient DOFs to allow a range of joint states for an end effector pose in a workspace. For example, for a given end effector position, the manipulator may occupy (and be driven between) any of a range of alternative manipulator linkage positions. Similarly, for a given end effector velocity vector, the manipulator may have a range of differing joint movement speeds for the various joints of the manipulator.

When used for minimally invasive robotic surgery, movement of the manipulator systems 120, 130, 140, 150 may be controlled by a controller of the system so that a shaft or intermediate portion of instruments mounted to the manipulator systems 120, 130, 140, 150 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator systems 120, 130, 140, 150 at the access sites may be imposed using mechanical manipulator joint linkages that inhibit improper motions, or may in part or in full be imposed using robotic data processing and control techniques. Hence, such minimally invasive aperture-constrained motion of the manipulator may employ between zero and three DOFs of the manipulator.

In some examples, a first manipulator system and a second manipulator system of the manipulator systems 120, 130, 140, 150 hold instruments, and a third manipulator system of the manipulator systems 120, 130, 140, 150 holds an image capturing device such as a monoscopic or stereoscopic endoscope. In this example, the remaining, fourth manipulator system is available so that another instrument may be introduced at the work site. Alternatively, the remaining manipulator system may be used for introducing a second endoscope or another image capturing device, such as an ultrasound transducer, to the work site.

Each of the manipulator systems 120, 130, 140, and 150 is formed of links that are coupled together and manipulated through actuatable joints. Each of the manipulator systems 120, 130, 140, and 150 includes a setup assembly and a device manipulator. The setup assembly positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted example, the operator console 40 shown in FIG. 2 includes a stereo vision display 45 so that the user may view the work site (e.g. a surgical work) site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the work site on a suitable viewer or display, the operator (e.g. a surgeon) performs the procedure on the patient by manipulating master control input devices, which in turn control the motion of robotic instruments.

The operator console 40 also includes left and right input devices 41, 42 that the user may grasp respectively with his/her left and right hands to manipulate devices (e.g., instruments) being held by the manipulator systems 120, 130, 140, and 150 of the patient-side cart 100 in preferably six DOFs. Foot pedals 44 with toe and heel controls are provided on the operator console 40 so the user may control movement and/or actuation of devices associated with the foot pedals.

A processor 43 is provided in the operator console 40 for control and other purposes. The processor 43 performs various functions in the medical robotic system. In some examples, the processor 43 is operable to translate and transfer the mechanical motion of input devices 41, 42 to actuate their respective joints in their associated manipulator systems 120, 130, 140, and 150 so that the operator can manipulate devices, such as the instruments, from a remote location of the operator console 40. The processor 43 can also be configured to implement the methods, cross-coupling control logic, and controllers described herein.

Although described as a processor, it is to be appreciated that the processor 43 may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the operator console 40, the processor 43 may also be distributed as subunits throughout the telesurgery system.

Referring also to FIG. 1B, the manipulator systems 120, 130, 140, and 150 can manipulate devices such as instruments to perform tasks such as those associated with minimally invasive surgery. For example, in the depicted arrangement the manipulator system 120 is pivotably coupled to an instrument holder 122. A cannula 180 and an instrument 200 and are, in turn, releasably coupled to the instrument holder 122. The cannula 180 is a tubular member that is located at the patient interface site during a procedure such as a surgery. The cannula 180 defines a lumen in which an instrument shaft 302 of the instrument 200 is slidably disposed. As described further below, in some implementations, the cannula 180 includes a distal end portion with a body wall retractor member.

The instrument holder 122 is pivotably coupled to a distal portion (e.g. a distal link, a distal end portion such as a distal end, etc.) of the manipulator system 120. In some implementations, the pivotable coupling between the instrument holder 122 and the distal portion of manipulator system 120 is a motorized joint that is actuatable from the operator console 40 and processor 43.

The instrument holder 122 includes an instrument holder frame 124, a cannula clamp 126, and an instrument holder carriage 128. The cannula clamp 126 is fixed to a distal portion (e.g. a distal end or some other distal portion) of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some implementations, the movement of the instrument holder carriage 128 along the instrument holder frame 124 is a motorized, translational movement that is controllable by the processor 43.

The instrument 200 includes a transmission assembly 210, the shaft 302, and an end effector 330. The transmission assembly 210 is configured to be releasably coupled with the instrument holder carriage 128. The shaft 302 extends distally from the transmission assembly 210. The end effector 330 is disposed at a distal portion (e.g. a distal end or some other distal portion) of the shaft 302. The end effector 330 can move in the workspace with between two and six DOFs.

The shaft 302 defines a longitudinal axis 222 that is coincident with a longitudinal axis of the cannula 180. As the instrument holder carriage 128 translates along the instrument holder frame 124, the shaft 302 of the instrument 200 is moved along the longitudinal axis 222. In such a manner, the end effector 330 can be inserted and/or retracted from a workspace within the body of a patient.

Figure 3:
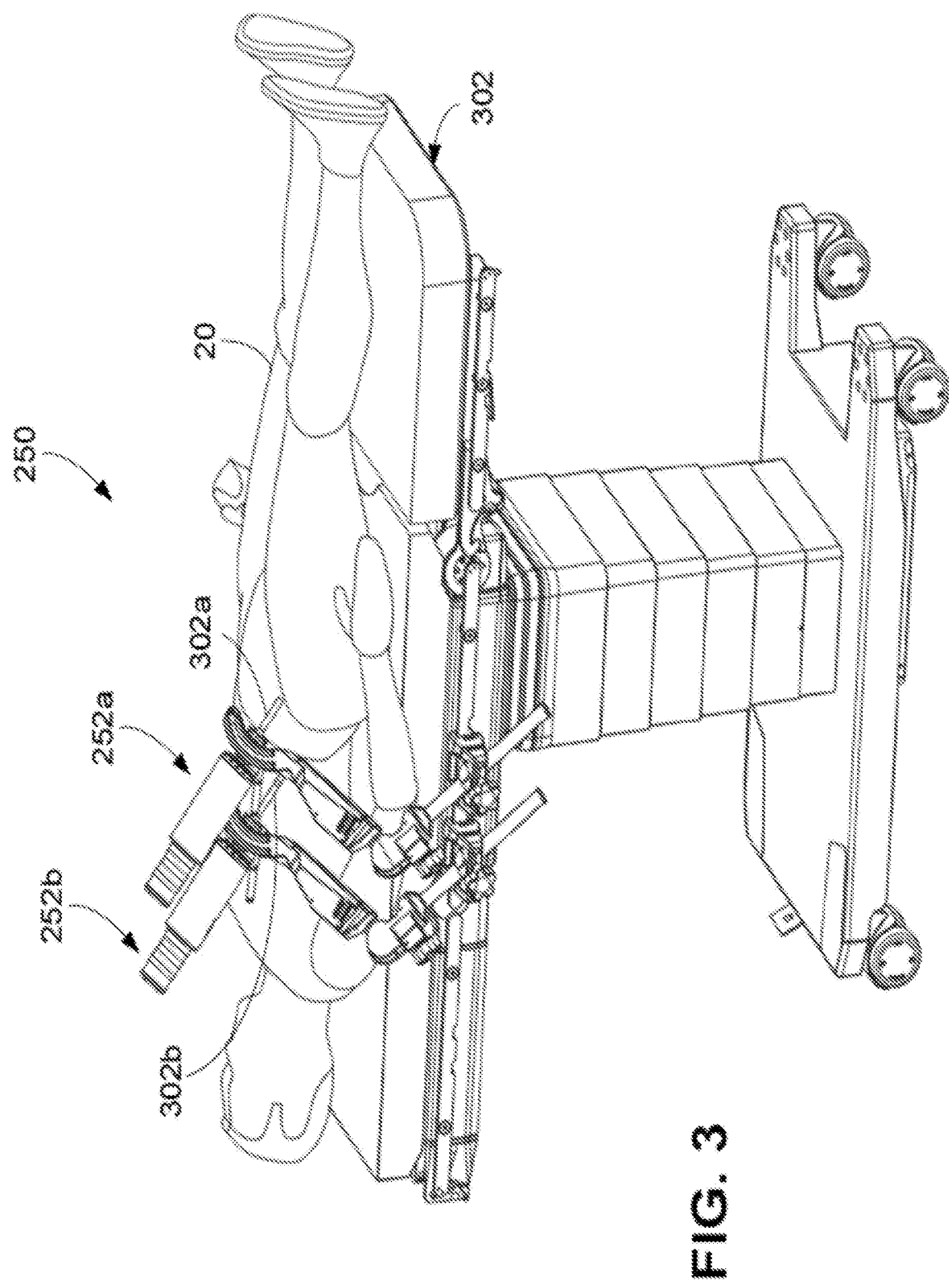
FIG. 3 is a perspective view of another example of a patient-side computer-assisted teleoperated system.

FIG. 3 is perspective view of another example of a patient-side system 250 for minimally invasive computer-assisted teleoperated surgery or other medical procedures. A patient 20 is supported on an operating table 10. The patient-side system 250 includes a first manipulator system 252a and a second manipulator system 252b that are each mounted to the operating table 10. In some cases, this configuration of patient-side system 250 can be used as an alternative to the patient-side cart 100 of FIG. 1. While only two manipulator systems 252a and 252b are depicted, it should be understood that more than two (e.g., three, four, five, six, and more than six) can be included in some configurations.

In some cases, the operating table 10 may be moved or reconfigured during the surgery or other medical procedure. For example, in some cases, the operating table 10 may be tilted about various axes, raised, lowered, pivoted, rotated, and the like. In some cases, such movements of the operating table 10 may be integrated as a part of the computer-assisted system, and controlled by the system.

The manipulator systems 252a, 252b are driven to move instruments 300a, 300b within the operating environment (e.g. a training environment in the case of training, a medical environment in the case of medical procedures—including a surgical environment in the case of surgery), e.g., relative to the patient 20. As described herein with respect to FIG. 4, in some implementations, the manipulator systems 252a, 252b include remotely operable powered joints that, when driven, reposition and reorient the instruments 300a, 300b such that the instruments 300a, 300b can be placed in desired poses during a procedure.

Figure 4:
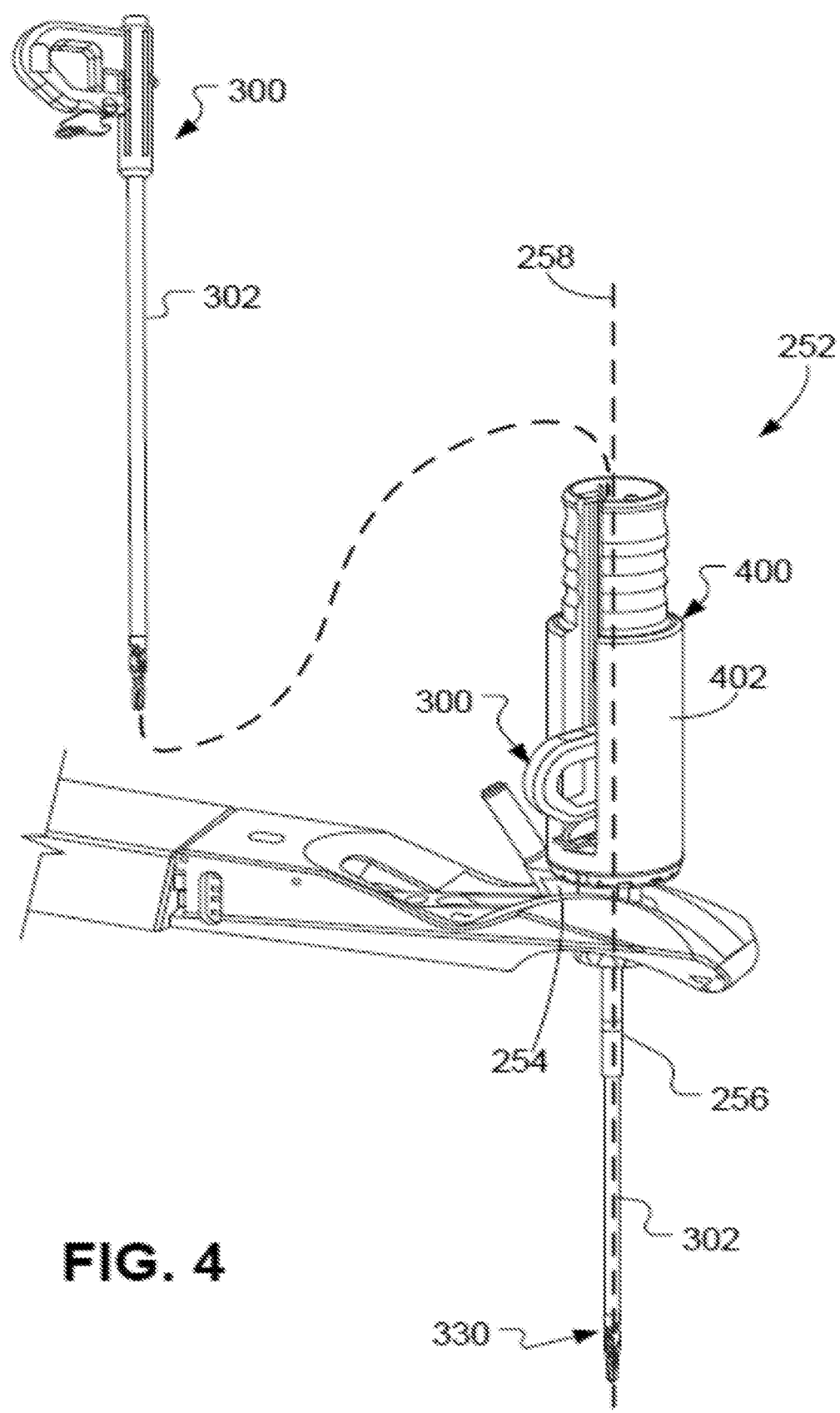
FIG. 4 is a perspective view of an example manipulator system of a computer-assisted teleoperated system.

FIG. 4 depicts a perspective view of a manipulator portion of a manipulator system 252, e.g., the manipulator system 252a or the manipulator system 252b, and an instrument 300 to be mounted to the manipulator system 252. The manipulator system 252 includes an instrument drive system coupling 254 to releasably couple with an instrument drive system 400 to which the instrument 300 is mounted. In particular, the coupling 254 is configured to releasably couple with a housing 402 of the drive system 400. The coupling 254 is also configured to releasably couple with a patient body wall access cannula 256 that is coaxial with an insertion axis 258 of the instrument 300. The cannula 256 defines a lumen that slidably receives a shaft 302 of the instrument 300 (or of other devices such as, but not limited to, an endoscope) along the insertion axis 258. During a medical operation, the cannula 256 extends distally from the coupling 254 through the patient via an access location on the patient body wall.

The drive system 400 releasably receives the instrument 300. In particular, the instrument 300 is inserted through the housing 402 of the instrument 300 and extends through the housing 402 into the cannula 256. The drive system 400 is, for example, detachable from the manipulator system 252 to enable the drive system 400 to be easily interchanged with another actuator system. When the instrument 300 is mounted to the drive system 400, the shaft 302 of the instrument 300 extends through the cannula 256. The cannula 256 extends through the patient body wall to guide the shaft 302 and an end effector 330 of the instrument 300 through the patient body wall into a cavity where the end effector 330 is to perform the operation. The end effector 330 is remotely controlled by the operator (e.g. surgeon 202 shown in FIG. 2) when the computer-assisted operation is performed.

The drive system 400 is, for example, a standalone unit including a system of drive mechanisms housed in the housing 402. The drive mechanisms are operated to control motion of the instrument 300 in multiple DOFs when the instrument 300 is mounted to the drive system 400. In some examples, the motions of the instrument 300 controllable by the drive mechanisms include a motion of part or all of the instrument 300 relative to the housing 402 of the drive system 400. The motions can also include a motion of the end effector 330 of the instrument 300. The manipulator system 252 drives the coupling 254 to control motion of the drive system 400 and the instrument 300 mounted to the drive system 400. The drive mechanisms include actuators to drive the actuation engagement members of the instrument 300, as described herein.

To control the motion of the instrument 300, the operator provides inputs using the operator console 40 as described in reference to FIG. 2 to generate control signals to operate the actuators of the drive system 400. In one example, the manipulator system 252 includes actuators to control a first set of DOFs of the instrument 300, and the drive system 400 includes one or more actuators to control a second set of DOFs of the instrument 300. The first set of DOFs includes, for example, a pitch motion, a yaw motion, and a roll motion of the instrument 300 relative to the patient 20. The instrument 300 is configured to undergo the pitch motion, the yaw motion, and the roll motion when the instrument 300 is mounted to the drive system 400 and the drive system 400 is mounted to the coupling 254. The second set of DOFs of the instrument 300 includes, for example, an insertion motion of the instrument 300 and an end effector motion of the end effector 330. In some examples, the insertion motion corresponds to a translation of the instrument 300 in its entirety along the longitudinal axis. In some examples, the insertion motion corresponds to a translation of a part of the instrument 300 along the longitudinal axis. In some examples, the manipulator system 252 does not include an actuator to cause actuation of the insertion motion or to actuate the end effector 330. Rather, the drive system 400 includes these actuators, and the drive system 400 can be disconnected from the manipulator system 252 to enable different actuation modules to be easily mounted to the manipulator system 252.

Example End Effectors

Figure 5:
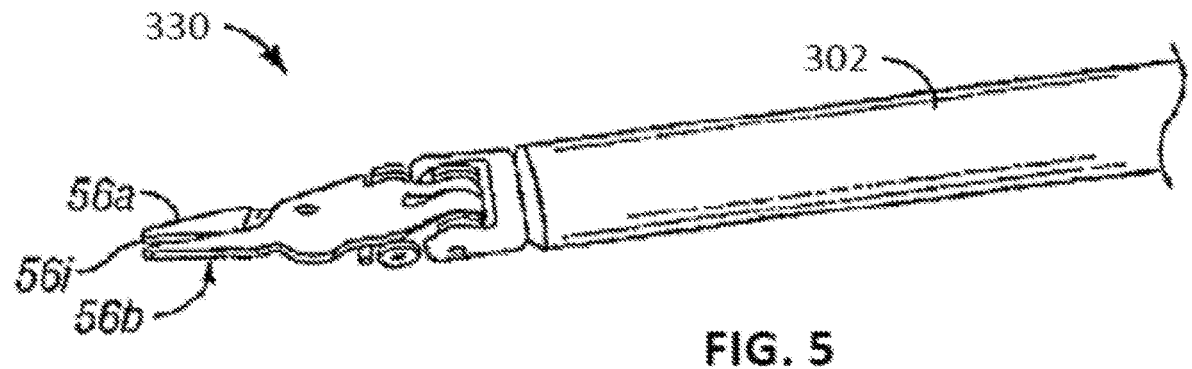
FIG. 5 is a perspective view of a distal end portion of an example instrument in a first configuration.
Figure 6:
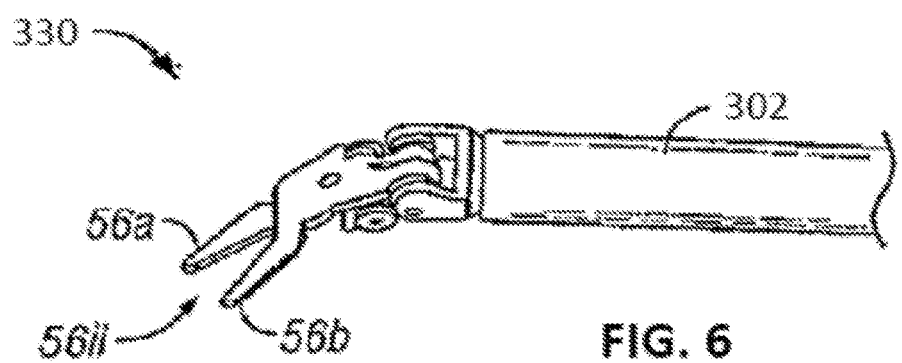
FIG. 6 is a perspective view of the distal end portion of the instrument of FIG. 5 in a second configuration.
Figure 7:
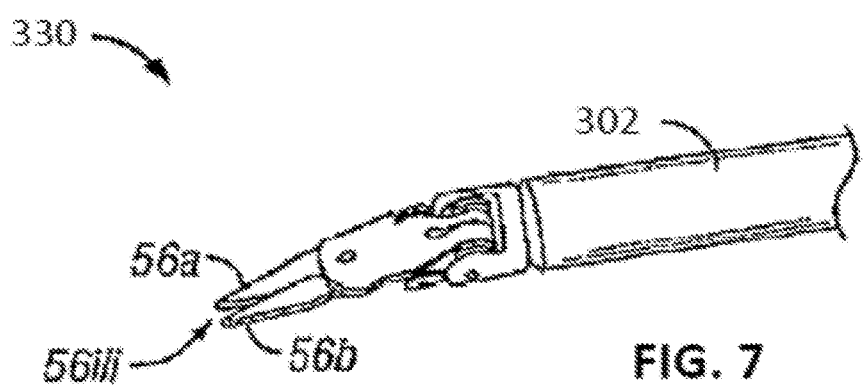
FIG. 7 is a perspective view of the distal end portion of the instrument of FIG. 5 in a third configuration.

Referring to FIGS. 5-7, the end effector motion of the second set of DOFs can vary between implementations. FIGS. 5-7 depict a variety of alternative computer-assisted teleoperated instruments of different types and differing end effectors 330 may be used, with the instruments of at least some of the manipulators being removed and replaced during a procedure. FIGS. 5-7 show instruments useful for a medical procedure such as a surgical procedure, and other non-surgical or non-medical instruments are contemplated. Several of these end effectors shown in FIGS. 5-7, including, for example, DeBakey Forceps 56*i*, microforceps 56*ii*, and Potts scissors 56*iii* include first and second end effector elements 56*a*, 56*b* which pivot relative to each other so as to define a pair of end effector jaws. Other end effectors, including scalpels and electrocautery probes, have a single end effector element. For instruments having end effector jaws, the end effector motion includes a clamping motion of the jaws. The jaws will often be actuated by squeezing the grip members of input devices 41, 42.

In some cases, the computer-assisted teleoperated instruments include multiple DOFs such as, but not limited to, roll, pitch, yaw, insertion depth, opening/closing of jaws, actuation of staple delivery, activation of electro-cautery, and the like. At least some of such DOFs can be actuated by an instrument drive system to which the instrument can be selectively coupled. While the descriptions of FIGS. 8-14 indicate that the second set of DOFs facilitated by the drive system 400 includes two DOFs with one of the DOFs being an insertion DOF and the other of the DOF being an end effector pitch DOF, in some implementations, additional DOFs are facilitated by the drive system 400. The end effector motion can include multiple modes of motion, e.g., motion in multiple DOFs. The end effector is, for example, movable in two or more of a roll motion, a pitch motion, a yaw motion, and/or a clamping motion. The end effector is further movable along a longitudinal axis of the instrument 300 in the insertion motion.

In some implementations, the computer-assisted teleoperated instruments include end effectors with two individually movable components such as, but not limited to, opposing jaws designed for grasping or shearing. When a first one of the individually movable components is moved as a second one of the individually movable components remains generally stationary or is moved in an opposing manner, the end effector can perform useful motions such as opening and closing for grasping, shearing, releasing, and the like. When the two components are moved synchronously in the same direction, speed and distance, the resulting motion is a type of pitch or yaw movement of the end effector. Hence, in some examples of instruments that have end effectors with two individually movable components, such as jaws, the arrangement can provide two DOFs (e.g., pitch/yaw movements and opening/closing movements).

In a medical application, the shaft 302 allow the end effector 330 and the distal end of the shaft 302 to be inserted distally into a medical worksite, such as a surgical worksite, through a minimally invasive aperture (via cannula 180), which may be through a body wall (e.g., abdominal wall), a natural orifice such as the mouth or anus, or the like. In some cases, a body wall retractor member on a distal portion (e.g. a distal end or some other distal portion) of the cannula 180 can be used to tent the body wall, thereby changing the workspace size or shape, and in some cases increasing the workspace size. In some cases, a worksite may be insufflated, and movement of the end effectors 330 within the patient will often be effected, at least in part, by pivoting of the instruments 200 about the location at which the shaft 302 passes through the minimally invasive aperture. In other words, the manipulator systems 120, 130, 140, and 150 will move the transmission assembly 210 outside the patient so that the shaft 302 extends through a minimally invasive aperture location so as to help provide a desired movement of end effector 50. Hence, in a surgical application, the manipulator systems 120, 130, 140, and 150 will often undergo significant movement outside of the patient during a surgical procedure.

Example Instruments

Figure 8:
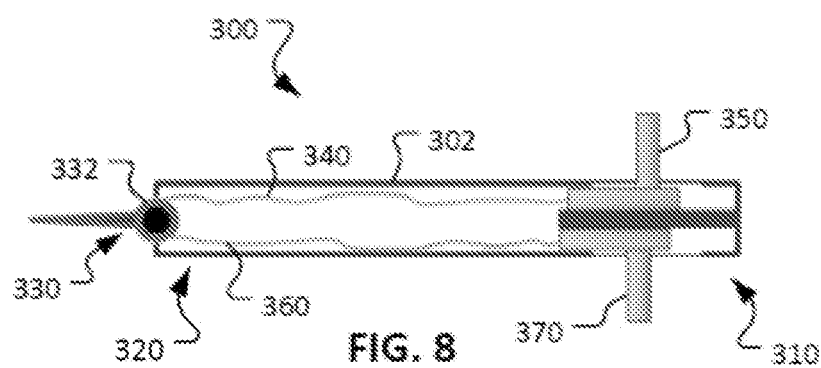
FIG. 8 is a schematic diagram of an example teleoperated instrument.

Referring to FIG. 8, an example instrument 300 that can be used as part of a computer-assisted teleoperated surgery system is schematically depicted. The instrument 300 includes an instrument shaft 302 having a proximal end portion 310 and a distal end portion 320 opposite from the proximal end portion 310. The instrument 300 also includes an end effector 330. In this schematic diagram, the end effector 330 is depicted as having a single degree of freedom (DOF) in relation to the shaft 302 (i.e., a freedom to pan the end effector 330 in a rotary or pivoting fashion). It should be understood, however, that the end effectors 330 of the instruments described herein can have more than one DOF (e.g., two, three, four, five, six, or more than six DOFs). Moreover, it should be understood that the concepts described in the context of the single DOF of the end effector 330 can be extended to each DOF of multiple DOFs of the instrument 300 and of other types of instruments for computer-assisted teleoperated surgery systems.

Example instrument 300 also includes a first tensioning member 340, a first engagement member 350, a second tensioning member 360, and a second engagement member 370. The first tensioning member 340 and the second tensioning member 360 comprise a flexible tensioning member for the instrument 300. The first tensioning member 340 is coupled to the end effector 330 and extends along the shaft 302 where it terminates at the first engagement member 350. Similarly, the second tensioning member 360 is coupled to the end effector 330 and extends along the shaft 302 where it terminates at the second engagement member 370. The first engagement member 350 and the second engagement member 370 are movably coupled to the proximal end portion 310 of the instrument. In some implementations, the first engagement member 350 and the second engagement member 370 are slidably coupled to the proximal end portion 310 of the instrument.

In some implementations, some or all portions of the first tensioning member 340 and the second tensioning member 360 include flexible cables (e.g., without limitation, stranded tungsten cables). In some implementations, the first tensioning member 340 and the second tensioning member 360 are different portions of a single, continuous component, such as a single, continuous cable. In some implementations, the first tensioning member 340 and the second tensioning member 360 comprise components physically separate from each other, such as two or more separate cables. The first tensioning member 340 and the second tensioning member 360 may additionally or alternatively include other components such as, but not limited to, hypo-tubes.

The first tensioning member 340 and the second tensioning member 360 are each coupled to the end effector 330. In the depicted example, the first tensioning member 340 and the second tensioning member 360 are each coupled to the end effector 330 via a pulley 332 (which can be a capstan, crank arm, rotary drive member, etc.). Hence, a proximal movement of the first engagement member 350 moves the second engagement member 370 distally, and moves the end effector 330 in a first manner relative to the shaft 302. Conversely, a proximal movement of the second engagement member 370 moves the first engagement member 350 distally, and moves the end effector 330 in a second manner relative to the shaft 302.

The instrument 300 is depicted here as being separated from an instrument drive system. Accordingly, in some implementations, the tension in the first tensioning member 340 and the second tensioning member 360 can be less than the tension used during the operation of the instrument 300. In some cases, having a relatively low tension in the first tensioning member 340 and the second tensioning member 360 while the instrument 300 is not in use can be advantageous (e.g., to reduce the potential for cable stretch). In some implementations, pre-load tensioning members (e.g., springs, not shown) may be included in instrument 300 to maintain a minimal tension in the first tensioning member 340 and the second tensioning member 360 while the instrument 300 is separated from an instrument drive system. Such minimal pre-tensioning may help ensure that the first tensioning member 340 and the second tensioning member 360 remain oriented within the instrument 300 as desired.

While the instrument 300 is depicted as having a single DOF, it should be understood that this is a simplified schematic diagram and that the instrument 300 can have two or more DOFs. The concepts described herein in reference to the single DOF of instrument 300 (as depicted) can be extrapolated to the two or more DOFs of the instruments provided herein. For example, when the end effector 330 includes two individually movable components, such as opposing jaws designed for grasping or shearing as described above, the arrangement provides two DOFs (e.g., pitch/yaw movements when the components are moved synchronously and opening/closing movements when the components are moved asynchronously or in an opposing manner). Extending the concepts described in reference to the instrument 300 to such an end effector would result in an instrument having four engagement members and four tensioning members to actuate the two DOFs.

Figure 9A:
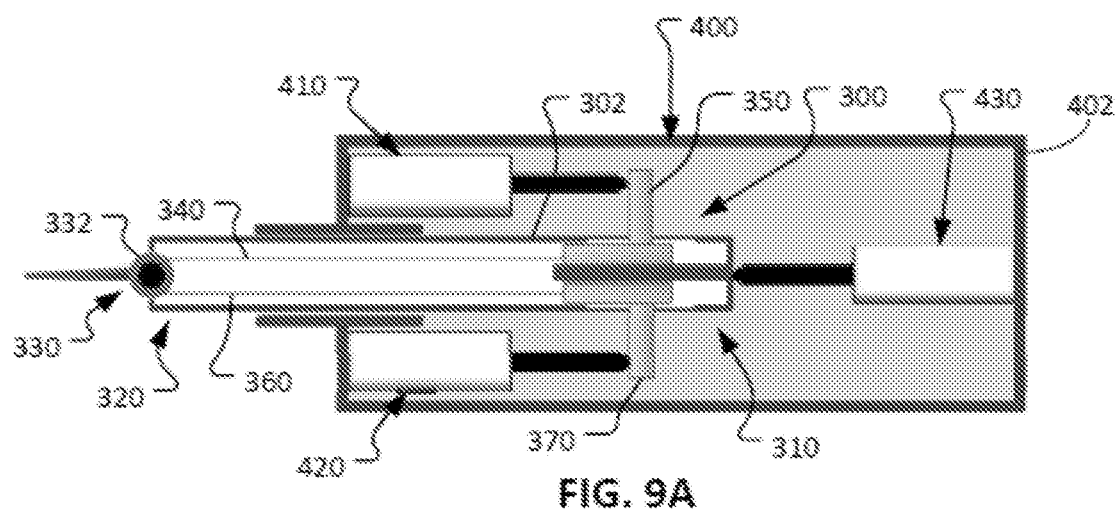
FIG. 9A is a schematic diagram of the teleoperated instrument of FIG. 8 coupled with an example instrument drive system.

Referring to FIG. 9A, the instrument 300 can be selectively coupled with an instrument drive system 400. That is, the instrument 300 can be coupled with the drive system 400 for operation as part of a computer-assisted system such as a computer-assisted teleoperated surgery system. Additionally, the instrument 300 can be uncoupled from the drive system 400 (e.g., for replacement by another type of instrument, for sterilization of the instrument 300, etc.).

In some implementations, the drive system 400 can be mounted to a manipulator, which can in turn be mounted to another structure or a base. The drive system 400 can be interchangeably mounted to a manipulator in some cases. That is, in some implementations, the drive system 400 is designed for convenient detachment from a manipulator such that it is readily interchangeable with another instrument drive system. In some implementations, the drive system 400 is interchangeable with other instrument drive systems. In some implementations, the drive system 400 is affixed to a manipulator in such a way that the drive system 400 is not readily detachable or interchangeable.

In some implementations, the instrument 300 is configured to be slidably coupled with the drive system 400. That is, the instrument 300 can be slidably extended distally and slidably retracted proximally in relation to the drive system 400.

The drive system 400 includes drive mechanisms that are configured to couple with the engagement members of the instrument 300 and drive the engagement members. The drive mechanisms include actuators operable to drive the engagement members. In the depicted example, the drive system 400 includes a first drive mechanism including a first actuator 410, a second drive mechanism including a second actuator 420, and a third drive mechanism including a shaft actuator 430. In some implementations, the first, second, and/or third drive mechanisms include drivetrains to convert torques applied by the first, second, and third actuators 410, 420, 430 into forces on, or longitudinal translation of, the engagement members 350, 370 of the instrument 300. The first actuator 410 is configured to be releasably coupled with the first engagement member 350. When thus coupled, the first actuator 410 can induce a tensile force in the first tensioning member 340. The second actuator 420 is configured to be releasably coupled with the second engagement member 370. When thus coupled, the second actuator 420 can induce a tensile force in the second tensioning member 360. The first, second, and third drive mechanisms, for example, include lead screws that can be rotated to apply forces, or cause motion, parallel to the longitudinal axis of the instrument 300 when the first, second, and third actuators 410, 420, 430 are driven.

In light of the arrangement between the instrument 300 and the first and second actuators 410 and 420 of the drive system 400 as described above, it can be envisioned that concerted modulation of the forces exerted from the first and second actuators 410 and 420 to the first and second engagement members 350 and 370, respectively, can result in controlled motion of the end effector 330 along its DOF. Moreover, it can also be envisioned (as described further below), that the tensions in the first and second tensioning members 340 and 360 can also be controlled by the concerted modulation of the forces exerted from the first and second actuators 410 and 420 to the first and second engagement members 350 and 370, respectively. Still further, it can also be envisioned that the tensions in the first and second tensioning members 340 and 360 can be controlled by the concerted modulation of the forces exerted from the first and second actuators 410 and 420 to the first and second engagement members 350 and 370, respectively, while the concerted modulation of the forces exerted from the first and second actuators 410 and 420 to the first and second engagement members 350 and 370 also concurrently cause desired movements of the end effector 330. In this way, the tensions in the first and second tensioning members 340 and 360 can be controlled to a desired amount of tensile force while movements of the end effector 330 are being made as desired. This concept can be referred to herein as "dynamic tension control."

Still referring to FIG. 9A, the drive system 400 also includes the third drive mechanism including the shaft actuator 430. The shaft actuator 430 can releasably couple with the shaft 302. In some implementations, the shaft actuator 430 can releasably couple with the shaft 302 (or to a structure coupled to the shaft 302) using a latch mechanism. Accordingly, in some such implementations, while the shaft actuator 430 is latched or otherwise physically coupled to the shaft 302, the shaft actuator 430 is able to drive the shaft 302 by applying one or more forces or torques to the shaft 302. In some such implementations the shaft actuator 430 is able to exert a distally-directed force or a proximally-directed force to the shaft 302. When the forces applied by the shaft actuator 430 is sufficient to overcome other forces experienced by the shaft 302, the forces applied by the shaft actuator 430 can distally extend or proximally retract the instrument 300 in relation to the drive system 400.

The actuators 410, 420, and 430 can be various types of actuators. Example actuator types include electrical actuators, hydraulic actuators, pneumatic actuators, magnetic actuators, light actuators, etc. Thus, although many of the examples discussed herein use motors, same or analogous techniques can utilize actuators based on other technologies. In some implementations, the first actuator 410, a second actuator 420, and a shaft actuator 430 each includes electrical motors that are coupled to lead screws that linearly drive nut members on the threads of the lead screw. In some implementations, the entire assembly of the instrument 300 in combination with the drive system 400 can be driven together to result in a desired motion of the end effector, such as a rolling motion about the longitudinal axis of the instrument 300.

Figure 9B:
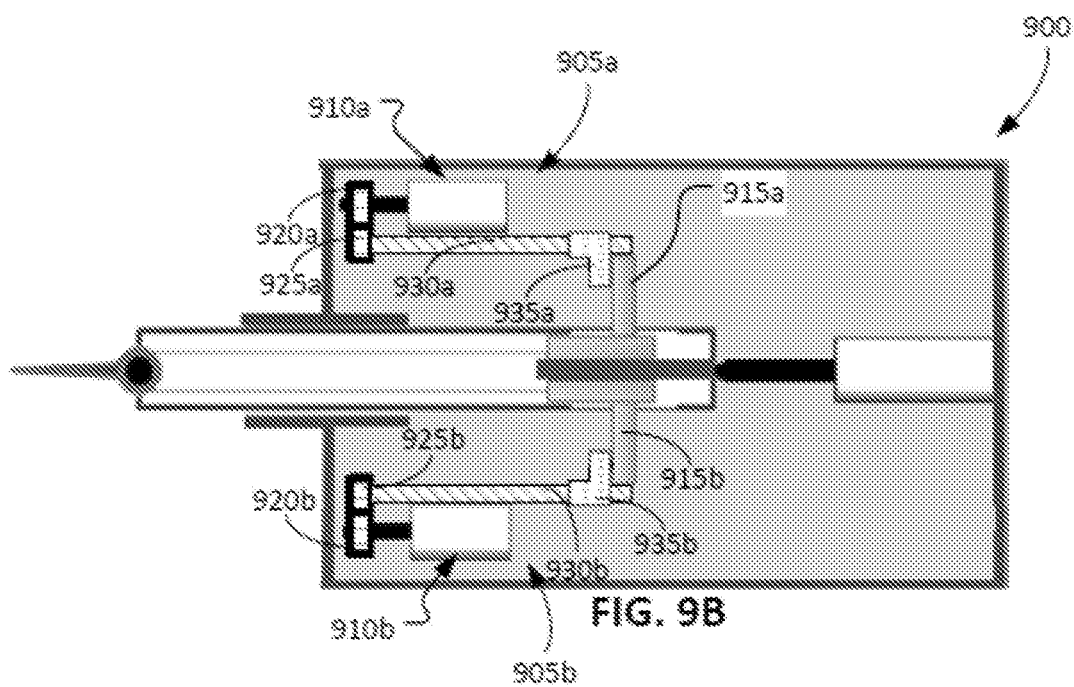
FIG. 9B is a schematic diagram of the teleoperated instrument of FIG. 8 coupled with another example instrument drive system.

FIGS. 10-14 are described with respect to FIG. 9A. However, other implementations are possible, including the one described with respect to FIG. 9B and others. Referring to FIG. 9B, an instrument 900 differs from the instrument 300 in that drive mechanisms 905a, 905b include actuators 910a, 910b as well as additional drivetrain components to move engagement members 915a, 915b. In particular, the drive mechanisms 905a, 905b include gears 920a, 920b mounted to the actuators 910a, 910b, which are rotary actuators. The gears 920a, 920b are engaged to gears 925a, 925b fixed to lead screws 930a, 930b. As the lead screws 930a, 930b rotate in response to rotation of the actuators 910a, 910b, the lead screws 930a, 930b translate longitudinally to cause abutting members 935a, 935b to translate and move the engagement members 915a, 915b. FIGS. 9A and 9B depict some examples of different possible drive mechanisms. Other drive mechanisms that facilitate linear motion of the engagement members 915a, 915b are possible.

Figure 10:
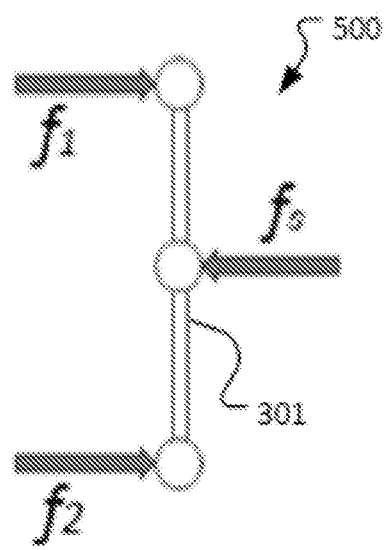
FIG. 10 is a force diagram pertaining to the instrument and drive system of FIG. 9A.

Referring also to FIG. 10, a force diagram 500 can be used to further describe the structure and operations of the instrument 300 in combination with the drive system 400. The body 301 is representative of the instrument 300. Force F1 is representative of the force applied by the first actuator 410 to the first engagement member 350. Force F2 is representative of the force applied by the second actuator 420 to the second engagement member 370. Force FS is representative of the force applied by the shaft actuator 430 to the shaft 302.

Force FS is directionally opposite to forces F1 and F2. Hence, in a static context, force FS is equal to the sum of forces F1 and F2. In a dynamic context, if force FS is greater than the sum of forces F1 and F2, then the body 301 will move in the direction of force FS. Conversely, if force FS is less than the sum of forces F1 and F2, then the body 301 will move in the direction of forces F1 and F2.

Applying the principles described above regarding the force diagram 500 to the analogous arrangement of the instrument 300 in combination with the drive system 400, the following concepts can be envisioned. While the instrument 300 is in a constant spatial relationship with the drive system 400 (i.e., in a static context), the sum of the forces exerted from the first and second actuators 410 and 420 to the first and second engagement members 350 and 370 equal the force exerted from the shaft actuator 430 to the shaft 302. In addition, while the sum of the forces exerted from the first and second actuators 410 and 420 to the first and second engagement members 350 and 370 are greater than the force exerted from the shaft actuator 430 to the shaft 302, the instrument 300 will move proximally in relation to the drive system 400. Still further, while the sum of the forces exerted from the first and second actuators 410 and 420 to the first and second engagement members 350 and 370 are less than the force exerted from the shaft actuator 430 to the shaft 302, the instrument 300 will move distally in relation to the drive system 400.

In general, the combinations of forces from the actuators 410, 420, and 430 that cause the proximal and distal movements of the instrument 300 in relation to the drive system 400 involve the sum of the forces exerted from the first and second actuators 410 and 420 to the first and second engagement members 350 and 370. Hence, it can be envisioned that the forces exerted from the first and second actuators 410 and 420 to the first and second engagement members 350 and 370 can be equal to each other, or can differ from each other while the sum of the forces is still a total amount that is appropriate to result in a desired distal/proximal movement and/or orientation between the instrument 300 and the drive system 400. For example, in the case when the forces exerted from the first and second actuators 410 and 420 to the first and second engagement members 350 and 370 differ from each other, a movement of end effector 330 will result, and in the case when the forces exerted from the first and second actuators 410 and 420 to the first and second engagement members 350 and 370 are equal to each other, the end effector 330 will be stationary in relation to the shaft 302. Again, it should be understood that, using the structure and operational concepts provided herein, distal/proximal movements of the instrument 300 in relation to the drive system 400 can be made concurrently with movements of the end effector 330 in relation to the shaft 302. Moreover, both such movements can be made concurrently while the tensions in the first tensioning member 340 and the second tensioning member 360 are maintained at a desired level of tensile force (e.g., within a target range of desired tensile force).

Figure 11:
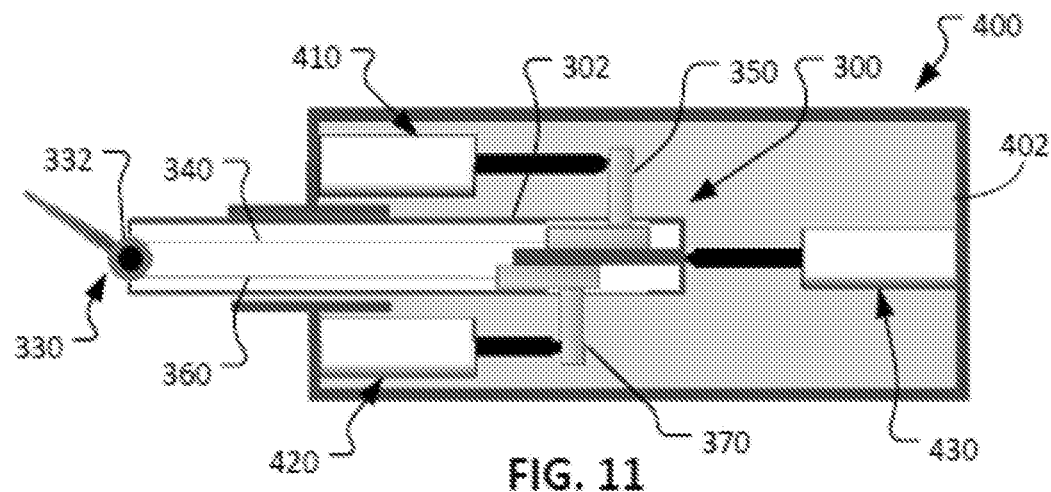
FIG. 11 is a schematic diagram of the instrument and drive system of FIG. 9A with the end effector oriented in an example pose.
Figure 12:
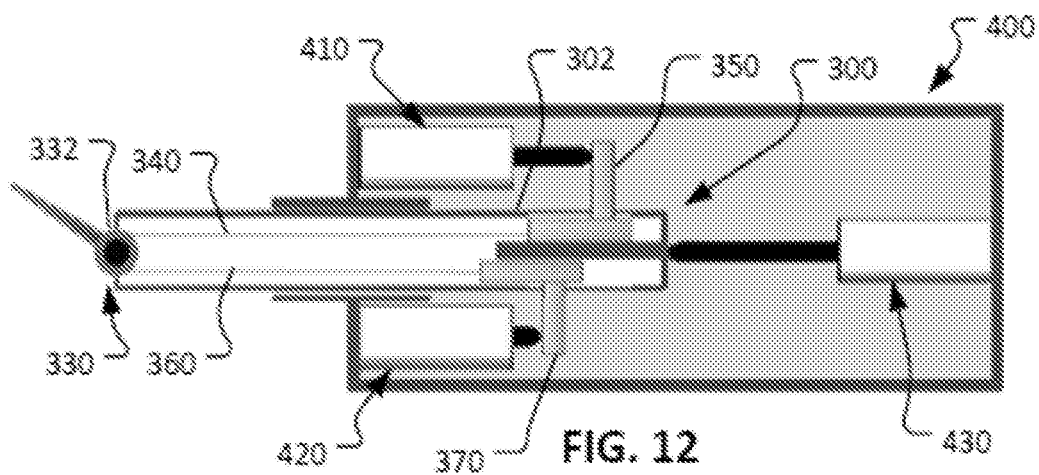
FIG. 12 is a schematic diagram of the instrument and drive system of FIG. 11 with the instrument extended distally in relation to the drive system while the end effector remains oriented in the example pose.
Figure 13:
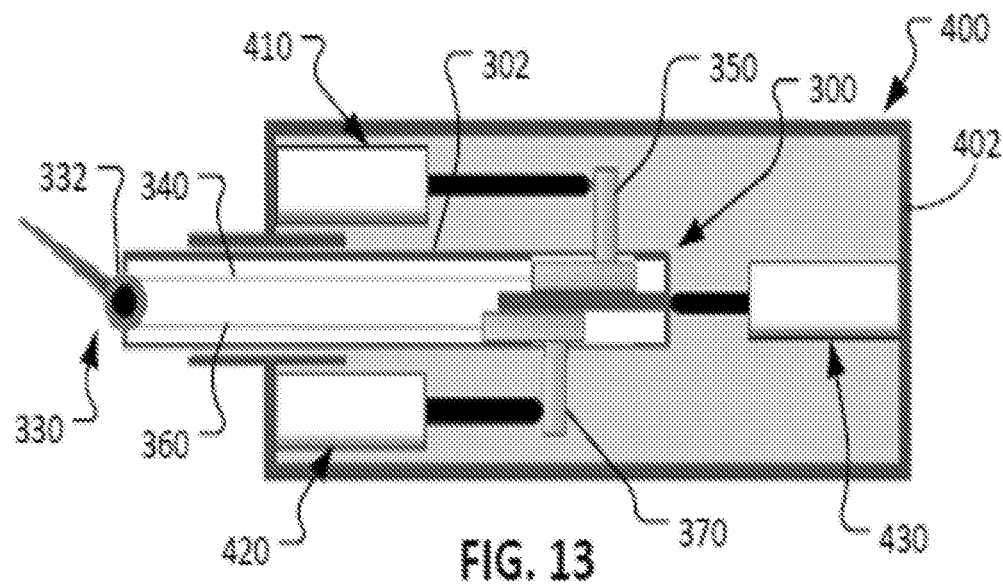
FIG. 13 is a schematic diagram of the instrument and drive system of FIG. 11 with the instrument retracted proximally in relation to the drive system while the end effector remains oriented in the example pose.

Referring also to FIGS. 11-13, the concepts described above can be further described by examples using illustrations of the instrument 300 in various orientations in relation to the drive system 400.

In a first example, the arrangement of FIG. 9A can be transitioned to that of FIG. 11 by temporarily increasing the force exerted by the first actuator 410 to the first engagement member 350 in comparison to the force exerted by the second actuator 420 to the second engagement member 370, while the sum of the two forces is held equal to the force exerted by the shaft actuator 430 to the shaft 302. In result, the second engagement member 370 moves distally relative to the first engagement member 350, and the end effector 330 moves in relation to the shaft 302 while the instrument 300 is maintained in a constant spatial relationship (i.e., no distal and proximal movements) in relation to the instrument drive system 400. Such a movement can be made while the tensions in the first tensioning member 340 and the second tensioning member 360 are maintained at a desired level of tensile force (e.g., within a target range of desired tensile force).

Ina second example, the arrangement of FIG. 9A can be transitioned to that of FIG. 12 by temporarily increasing the force exerted by the first actuator 410 to the first engagement member 350 in comparison to the force exerted by the second actuator 420 to the second engagement member 370, while the sum of the two forces is temporarily less than the force exerted by the shaft actuator 430 to the shaft 302. In result, both the first and second engagement members 350, 370 move distally. In addition, the end effector 330 moves in relation to the shaft 302, and the instrument 300 extends distally in relation to the instrument drive system 400. Such movements can be made while the tensions in the first tensioning member 340 and the second tensioning member 360 are maintained at a desired level of tensile force (e.g., within a target range of desired tensile force).

In a third example, the arrangement of FIG. 9A can be transitioned to that of FIG. 13 by temporarily increasing the force exerted by the first actuator 410 to the first engagement member 350 in comparison to the force exerted by the second actuator 420 to the second engagement member 370, while the sum of the two forces is temporarily greater than the force exerted by the shaft actuator 430 to the shaft 302. In result, the engagement members 350, 370 move proximally. In addition, the end effector 330 moves in relation to the shaft 302, and the instrument 300 retracts proximally in relation to the instrument drive system 400. Such movements can be made while the tensions in the first tensioning member 340 and the second tensioning member 360 are maintained at a desired level of tensile force (e.g., within a target range of desired tensile force).

In a fourth example, the arrangement of FIG. 12 can be transitioned to that of FIG. 13 by maintaining equal forces exerted by the first actuator 410 to the first engagement member 350 and by the second actuator 420 exerted to the second engagement member 370, while the sum of the two forces is temporarily greater than the force exerted by the shaft actuator 430 to the shaft 302. In result, the end effector 330 will not move in relation to the shaft 302, and the instrument 300 will retract proximally in relation to the instrument drive system 400. Such a movement can be made while the tensions in the first tensioning member 340 and the second tensioning member 360 are maintained at a desired level of tensile force (e.g., within a target range of desired tensile force).

In a fifth example, the arrangement of FIG. 13 can be transitioned to that of FIG. 12 by maintaining equal forces exerted by the first actuator 410 to the first engagement member 350 and by the second actuator 420 exerted to the second engagement member 370, while the sum of the two forces is temporarily less than the force exerted by the shaft actuator 430 to the shaft 302. In result, the end effector 330 will move in relation to the shaft 302, and the instrument 300 will extend distally in relation to the instrument drive system 400. Such a movement can be made while the tensions in the first tensioning member 340 and the second tensioning member 360 are maintained at a desired level of tensile force (e.g., within a target range of desired tensile force).

Figure 14:
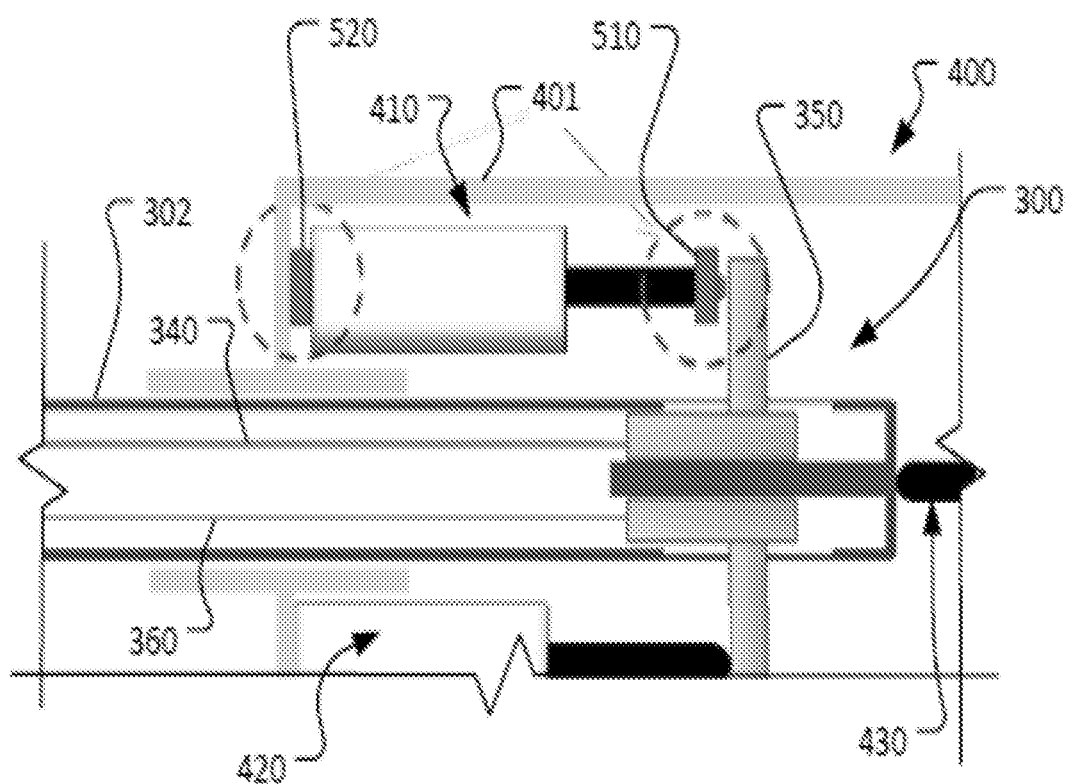
FIG. 14 is a schematic diagram of a portion of the instrument and drive system of FIG. 11 showing example locations of load cells for detecting forces such as cable tension.

Referring to FIG. 14, in some implementations, the forces exerted by the actuators 410, 420, and/or 430 to the instrument 300 can be detected by the use of one or more sensors. Output signals from these sensors can be used for controlling the actuators 410, 420, and/or 430 (i.e., to control movements of the instrument 300 and/or to control tensions of the first and second tensioning members 340 and 360).

In some implementations, a sensor 510 disposed near the juncture between the first actuator 410 and the first engagement member 350. The sensor 510 is, for example, a load cell. A sensor 520 disposed near the juncture between the first actuator 410 and a structural member 401 of the drive system 400. The sensor 520 is also, for example, a load cell. The drive system 400 can be readily interchangeable in relation to mounting on a manipulator.

In some implementations, other devices can be used to detect the forces exerted by the actuators 410, 420, and/or 430 to the instrument 300. For example, in some implementations, strain gauges can be located on the engagement members, e.g., the first engagement member 350. In another example, the electrical current drawn by electric motors of the actuators 410, 420, and/or 430 can be measured and used as an indication of the forces exerted by the actuators 410, 420, and/or 430 to the instrument 300. In some implementations, a combination of such sensors and techniques can be used.

While the sensors 510, 520 are coupled to the first actuator 410 and/or the first engagement member 350, in some implementations, the drive system 400 and/or the instrument 300 further includes sensors coupled to the second actuator 420 and/or sensors coupled to the third actuator 430. The combination of sensors present can enable forces and torques applied by each actuator 410, 420, and/or 430 to be determined. Furthermore, while described as load cells, in some implementations, additional or alternative sensors may be present. The sensors include, for example, position sensors, pressure sensors, torque sensors, encoders, etc.

Referring to FIGS. 15-18, an example instrument 600 is shown and used to illustrate various techniques that can be used with surgical and non-surgical instruments. Where instrument 600 is a surgical instrument, it can be used with or as part of a computer-assisted teleoperated surgery system. Instrument 600 includes a proximal end portion 610, an instrument shaft 640, and an end effector 650. The instrument 600 is an example of an instrument that is configured in accordance with the schematic diagrams (e.g., FIGS. 8, 9, and 11-14) described above. Hence, the instrument 600 can function in accordance with the schematic diagrams described above.

The instrument shaft 640 extends distally from the proximal end portion 610. The instrument shaft 640 includes a distal end portion to which the end effector 650 is coupled. The instrument shaft 640 defines a longitudinal axis 602 of the instrument 600. In a surgical implementation, the longitudinal axis 602 is often the axis along which the instrument 600 is inserted into and withdrawn from the patient.

The end effectors (e.g., end effector 650) of the instruments described herein can be any type of end effector (e.g., for surgical and other medical instruments, the end effectors may comprise graspers, cutters, cautery instruments, staplers, forceps, cameras, etc.). The end effectors (e.g., end effector 650) of the instruments described herein can have one or multiple degrees of freedom (e.g., two, three, four, five, six, seven, eight, or more than eight degrees of freedom). Moreover, it should be understood that the concepts described herein in the context of a single degree of freedom of the end effectors can be extended to each degree of freedom of multiple degrees of freedom of the instrument 600, of various types of surgical instruments for computer-assisted teleoperated surgery systems, and of various other types of instrument for computer-assisted medical and non-medical systems.

In the depicted embodiment, the proximal end portion 610 includes a handle 612, a plurality of engagement members 630 (depicted here disposed in a grouping at a same longitudinal location along the longitudinal axis 602), and an engagement member 620. The plurality of engagement members 630 are movably coupled to the proximal end portion 610. In the depicted embodiment, the plurality of engagement members 630 are slidably coupled to the proximal end portion 610 such that the plurality of engagement members 630 can translate parallel to the longitudinal axis 602. The engagement member 620 is coupled to the proximal end portion 610. In the depicted embodiment, engagement member 620 is pivotably coupled to the proximal end portion 610.

The handle 612 extends radially from the longitudinal axis 602. In the depicted embodiment, the handle 612 is the portion of proximal end portion 610 and of the entire instrument 600 that radially extends the farthest. The handle 612 is configured to facilitate manual gripping and manipulation of the instrument 600.

In some embodiments, the handle 612 includes an indicium that identifies the type of the instrument 600. For example, in the depicted embodiment the handle 612 includes a visible indicium that is an icon 614 that depicts that the instrument 600 is a grasper device. In some embodiments, the handle 612 includes a machine-readable indicium, such as an REID chip or NFC tag that can be used to store and communicate information pertaining to the instrument 600. For example, such information pertaining to the instrument 600 can include, but is not limited to, a unique identification or serial number, the type of instrument, the number of times the instrument has been used for the current procedure, a past selected number of procedures, or for all procedures, and/or the like.

In some embodiments, the handle 612 optionally includes one or more magnets that an instrument drive system can use to sense the presence of the instrument 600 mounted in the instrument drive system.

The proximal end portion 610 includes the plurality of engagement members. As depicted the engagement members 630 are disposed in a grouping at a common longitudinal location along the longitudinal axis 602. Optionally they may be at two or more longitudinal locations along longitudinal axis 602 so that a first coupled pair of engagement members is at a first longitudinal location and a second coupled pair of engagement members is at a second longitudinal location, or each engagement member of a coupled pair is at a different longitudinal location. The engagement members are configured to releasably engage with actuators which drive the engagement members and corresponding movements of the end effector 650 as described above in reference to FIGS. 8-14. As shown, each individual engagement member slides longitudinally in a corresponding individual longitudinal slot in proximal end portion 610. In other optional aspects, however, an individual engagement member may have a different configuration (e.g., a lever, a rotating piece such as a disk or gear, a cam surface, and the like). As shown, all individual engagement members extend radially outward slightly beyond the outer perimeter of proximal end portion 610 so that the associated actuators to not extend into proximal end portion 610. Alternatively, one or more individual engagement members may not extend to or beyond the outer perimeter of proximal end portion (e.g., they are positioned slightly inside proximal end portion 610) so they are less prone to damage or do not snag on an object. In this alternative configuration, the associated actuators extend slightly into proximal end portion 610 to engage the instrument's engagement members. All engagement members may have the same configuration, or two or more engagement member configurations may be used in a single instrument, as long as the engagement members comply with the principles of operation described with reference to FIGS. 8-14. In the depicted embodiment the following example engagement members are included: 632a, 632b, 634a, 634b, 636a, 636b, and 638. More or fewer engagement members may be included in some embodiments.

The engagement members, e.g., engagement members 632a, 632b, 634a, 634b, 636a, 636b, and 638, are coupled to tensioning members (e.g., comprising flexible cables that can be routed over small radius pulleys (e.g., 2-10 mm scale), semi-flexible cables that cannot be routed over small radius pulleys, rigid hypo-tubes, pull rods, etc.) that extend along the instrument shaft 640 and that are movably coupled to the end effector 650. Hence, movements of the engagement members result in movements of the end effector 650.

In some cases, the engagement members are paired (e.g., engagement members 632a and 632b, engagement members 634a and 634b, and engagement members 636a and 636b) such that moving one engagement member of the pair proximally results in a corresponding distal movement of the other engagement member of the pair. For example, moving engagement member 632a proximally results in a corresponding distal movement of engagement member 632b, and moving engagement member 632b proximally results in a corresponding distal movement of engagement member 632a. In other words, engagement member pairs move in opposition to each other.

When the structure of the instrument 600 includes engagement members (e.g., engagement members 632a, 632b, 634a, 634b, 636a, 636b, and 638) that are coupled to flexible tensioning cables, it can be envisioned that distal movements of the engagement members without a corresponding proximal movement of a paired engagement member will not move the end effector 650. Rather, the flexible tensioning cable attached to the engagement member being moved distally would simply become flaccid (due to the limited column strength/rigidity of a flexible tensioning cable). Hence, it can be said that, in some embodiments, the engagement members 632a, 632b, 634a, 634b, 636a, 636b, and 638 are configured to move the end effector 650 in response to receiving a proximally-directed force, and are configured to not move the end effector 650 in response to receiving a distally-directed force. However, in some embodiments one or more of the engagement members (e.g., the engagement member 638 which is not paired with another engagement member) are configured to move the end effector 650 both ways (proximally and distally). That is, such engagement members optionally drive a flexible or semi-flexible member in a manner similar to Bowden cable operation, or drive a rigid member in a manner similar to push/pull rod operation. For example, in some embodiments the engagement member 638 may be configured to operate a blade of the end effector 650 or a clamp in the case that the end effector 650 includes a stapler. In the example of the blade, the engagement member 638 works opposite to a spring (cut under drive, spring back). In the example of the stapler, the engagement member 638 moves distally to drive the firing sequence, while the grip-open actuation returns the engagement member 638 proximally.

Still referring to FIGS. 15-18, in the depicted arrangement of instrument 600, the engagement members 632a, 632b, 634a, 634b, 636a, 636b, and 638 are all positioned at the same longitudinal location along the longitudinal axis 602 of the instrument 600. However, during use of the instrument 600, the engagement members 632a, 632b, 634a, 634b, 636a, 636b, and 638 are moved to various longitudinal locations along the longitudinal axis 602 of the instrument 600. This is described further by the following example.

When the instrument 600 is coupled with an instrument drive system, actuators of the instrument drive system will releasably couple with the engagement members 632a, 632b, 634a, 634b, 636a, 636b, and 638. For example, the actuators will engage the engagement members by moving proximally until a reaction force that indicates engagement is sensed. For paired engagement members 632a and 632b, a first actuator moves proximally until engagement member 632a is engaged, and a second actuator moves proximally until engagement member 632b is engaged. The first and second actuators may then adjust the longitudinal position of the corresponding engagement members 632a and 632b to set a desired tension in corresponding paired tension members coupled to the distal end component so that all slack or backlash is removed from the drive train between the engagement members and the corresponding distal end component and so that movement of the engagement members results in immediate movement of the corresponding distal end component. That is, one or more instrument drive system actuators engage the corresponding one or more instrument engagement members and set a dynamic preload tension (which may be in addition to the static preload tension described below) in the one or more instrument tension members between the one or more engagement members and the corresponding instrument distal end component (e.g., wrist or end effector component).

Then, in response to input (such as from operator console 40 of FIG. 2), the actuators of the instrument drive system correspondingly move some or all of the engagement members (e.g., the engagement members 632a, 632b, 634a, 634b, 636a, and/or 636b) proximally to initiate desired movements of the end effector 650 or other distal end component. For example, for paired engagement members 632a and 632b, a first actuator of the instrument drive system may move engagement member 632a proximally. In concert with that proximal movement of engagement member 632a, a second actuator of the instrument drive system may resist distal movement of engagement member 632b, thus keeping tension on engagement member 632b's corresponding tension member, but still allows engagement member 632b to move distally. The second actuator's resistance to engagement member 632b's distal movement is modulated to maintain a desired tension in the tensioning members that correspond to the engagement members 632a and 632b. This operation is performed in accordance with the dynamic tensioning concepts described above in reference to FIGS. 8-14.

In one aspect, the control system controls the tension in each of the paired tension members to be equal as the tension members move the corresponding end effector. In another aspect, however, the control system controls the tension in the tension members to cause a required load force in the loaded tension member and to maintain a minimum tension, or at least a minimum tension, on the non-loaded tension member.

To explain this differential force aspect by example, consider paired engagement members 632a and 632b. When their associated end effector is at a neutral position (e.g., centered on the instrument's longitudinal axis and not engaged with another object), not moving, and not experiencing a load, the control system may cause an equal force to be applied to engagement members 632a and 632b. This equal force is at or above a minimum force required to remove backlash from the tension member connections between the end effector and the engagement members for effective control. But, the equal force is kept low in order to reduce friction and tension loads that result in mechanical wear.

To move the associated end effector, the control system moves the engagement members 632a and 632b in opposite directions. The end effector movement caused by the proximal motion of engagement member 632a may be unresisted (e.g., the end effector moves freely) or resisted (e.g., the end effector moves against tissue or another part of the end effector, such as a jaw moving against another jaw in grip). Friction in the drive train may also cause a load that requires a higher force be applied to engagement member 632a than is required to keep the end effector under effective control at a neutral position. Thus, the actuator associated with engagement member 632a must increase its force against engagement member 632 to either continue to move the corresponding end effector or to maintain the corresponding end effector's force against the resistance. In this situation, however, there is no need for the actuator associated with the paired engagement member 632b to exert a force on engagement member 632b that is the same as the force exerted on engagement member 632a. What is required is that the force exerted on engagement member 632b be at or above a minimum threshold necessary to keep the associated tension member from going slack or deviating from its path, such as by leaving a pulley.

As a further illustration, if the control system causes engagement member 632a to receive a maximum allowable force from its associated drive unit actuator in order to produce a maximum force at the corresponding end effector (e.g., to produce a maximum possible end effector grip force), then the control system may cause engagement member 632b to receive only a minimum force required to ensure that its associated tension member does not go slack and does not disengage from its proper routing, or to receive a force between this minimum force and the force applied to engagement member 632a. And, although this aspect applies for maximum force applied to engagement member 632a, it also applies when lower forces are applied so that again the conflicting tension caused by the force against engagement member 632b is minimized. It should be understood that if the end effector is then to be moved in the opposite direction, the required load force is applied against engagement member 632b, and the required tension-maintaining force is applied against engagement member 632a. It should also be understood that this differential force aspect applies if compression is used to move an end effector instead of tension, so that any unnecessary compression force is reduced or minimized.

In some embodiments of instrument 600, pre-load tensioning members (e.g., springs 633) may be included to maintain a minimal tension in the tensioning members while the instrument 600 is separated from an instrument drive system-a static preload tension. Such minimal pre-tensioning may help ensure that the tensioning members remain oriented and routed within the instrument 600 as desired. In the depicted embodiment, compression springs 633 apply a proximally-directed force to the engagement members 632a, 632b, 634a, 634b, 636a, 636b, and 638 to maintain a minimal tension in the tensioning members while the instrument 600 is separated from an instrument drive system. In some embodiments, other types of pre-load tensioning members may be used such as, but not limited to, flexures created as part of shaft 640 or proximal end portion 610, extension springs, torsion springs, leaf springs, and the like. Further, in embodiments that incorporate compression members in place of tensioning members, pre-load compression members similar to these pre-load tensioning members may be used to eliminate mechanical backlash in the drive trains between engagement members and the end effector.

Still referring to FIGS. 15-18, proximal end portion 610 includes the engagement member 620. The engagement member 620 is used for releasably coupling the proximal end portion 610 to an actuator of an instrument drive system. Since the instrument shaft 640 is rigidly coupled to the proximal end portion 610, the engagement member 620 also releasably couples the instrument shaft 640 to an actuator of an instrument drive system. This concept of using the engagement member 620 to couple an actuator to the proximal end portion 610 and the instrument shaft 640 was introduced above by the schematic diagrams and the descriptions thereof (e.g., by FIG. 9 which includes the shaft actuator 430 that can releasably couple with the instrument shaft 302). Hence, the engagement member 620, when coupled with an actuator of an instrument drive system, is used for moving the entire instrument 600 proximally and/or distally in relation to the instrument drive system. In addition (as described in reference to the force diagram of FIG. 10), the engagement member 620, when coupled with an actuator of an instrument drive system, is used for balancing proximally directed forces applied by actuators to the engagement members 632a, 632b, 634a, 634b, 636a, 636b, and 638.

In the depicted embodiment, the engagement members 632a, 632b, 634a, 634b, 636a, 636b, and 638 are configured to receive proximally-directed forces from the actuators of an instrument drive system but are not configured to receive distally-directed forces from the actuators of an instrument drive system. In other words, the engagement members 632a, 632b, 634a, 634b, 636a, 636b, and 638 are not detained (not immovably coupled with; a non-detained engagement) to the actuators of an instrument drive system. Stated differently, the engagement members 632a, 632b, 634a, 634b, 636a, 636b, and 638 are each configured for directly facilitating (causing) movement the end effector 650 in response to receiving a proximally-directed force from a corresponding actuator, and are each not configured for directly facilitating movement the end effector 650 in response to receiving a distally-directed force from a corresponding actuator. In contrast, in the depicted embodiment the engagement member 620 is configured to directly facilitate movement of the entire instrument 600 proximally in response to receiving a proximally-directed force, and is configured to directly facilitate movement of the entire instrument 600 distally in response to receiving a distally-directed force. That is the case because the engagement member 620 is configured to be releasably detained to an actuator of an instrument drive system. For example, in the depicted embodiment the engagement member 620 is a latch mechanism that can be used to releasably detain the proximal end portion 610 and the instrument shaft 640 to an actuator of an instrument drive system. It should be understood that the use of a latch mechanism for the engagement member 620 is not required in all embodiments, and other suitable coupling mechanisms at various locations on the instrument may be used.

Further, in some embodiments the engagement member 620 is configured such that the instrument drive system only exerts distally-directed forces to the instrument 600 (i.e., not proximally-directed forces). The dynamic tension and position control concepts described herein can still be performed in such a case where the engagement member 620 is configured to receive only a distally-directed force from the instrument drive system. In this aspect, distally-directed force on the instrument's shaft engagement member is balanced with proximally-directed forces on the instrument's engagement members.

Referring particularly to FIG. 18, in some embodiments the instrument 600 is configured with one or more connectors or contacts for inputting energy to the end effector 650 (e.g., energy for cauterization in a medical procedure). For example, in some embodiments the instrument 600 may be configured to use monopolar RF, bi-polar RF, or another energy form. In such a case, in some embodiments the one or more connectors are located on a proximal area 613 of the handle 612. Such a location can allow the one or more connectors to be readily accessible for connection with one or more cables that supply the energy. Such a location can also allow the connections to be made and/or disconnected while the instrument 600 is coupled with an instrument drive system.

Figure 19:
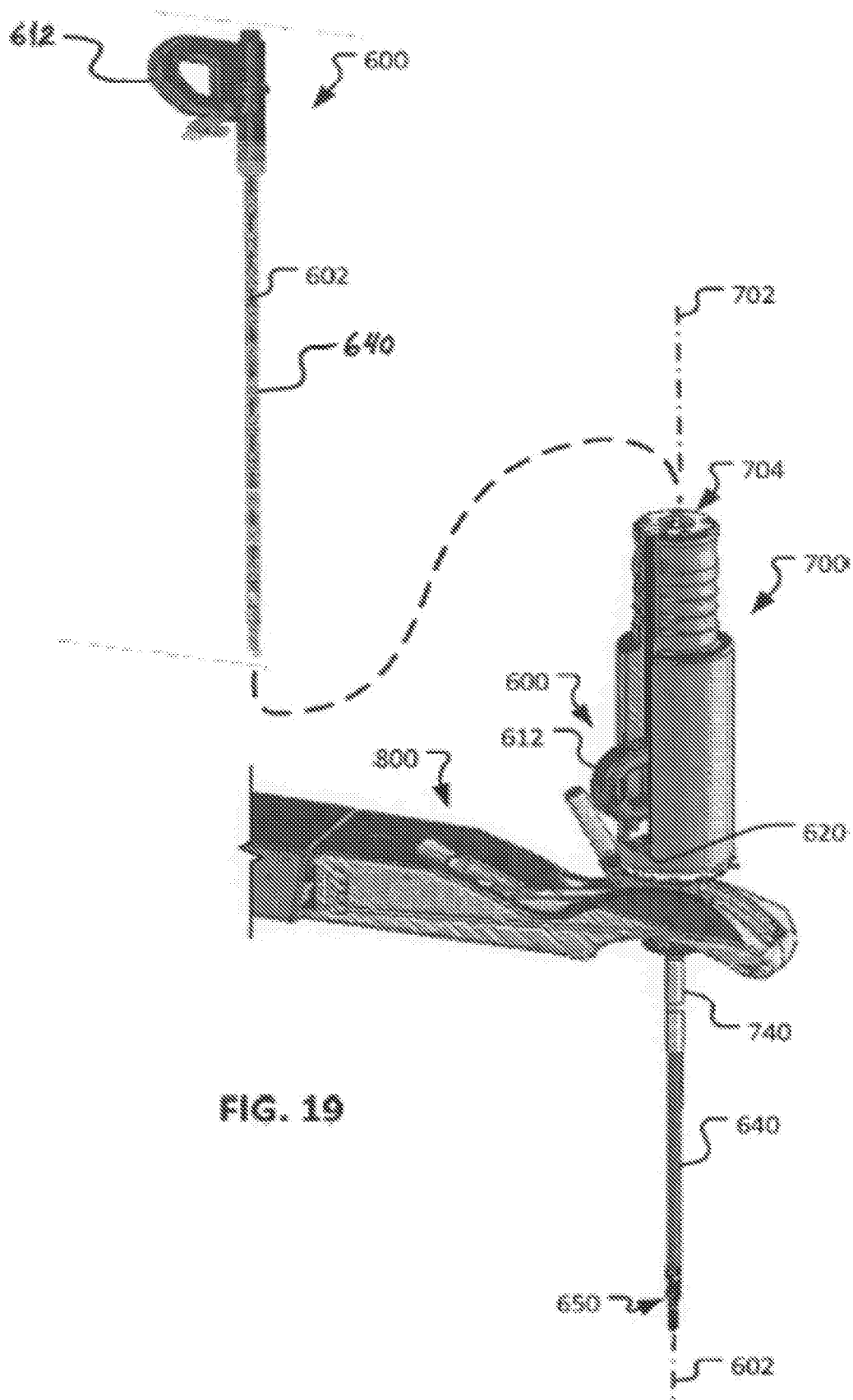
FIG. 19 depicts how the instrument of FIG. 15 can be coupled with an example instrument drive system in accordance with some embodiments.

Referring to FIG. 19, the instrument 600 can be selectively coupled with a compatible instrument drive system 700 (also referred to as pod 700) that defines a longitudinal axis 702 of a space configured to receive the instrument 600. In accordance with an implementation for computer-assisted teleoperated surgery, the instrument drive system 700 can be coupled to a manipulator assembly 800 with multiple degrees of freedom. In some embodiments, the instrument drive system 700 is readily detachable from the manipulator assembly 800 such that the instrument drive system 700 can be conveniently interchanged with another instrument drive system. The manipulator assembly 800 can be attached to a supporting structure of various types (e.g., refer to FIGS. 3 and 4). The instrument shaft 640 can slidably extend through a cannula 740 that is optionally releasably mounted to the manipulator assembly 800 or to the instrument drive system 700.

In the depicted embodiment, the instrument 600 can be releasably coupled with the instrument drive system 700 by moving the instrument 600 distally into an opening at the proximal end 704 of the instrument drive system 700. In particular, the longitudinal axis 602 of the instrument 600 can first be aligned with the longitudinal axis 702 of the instrument drive system 700. Then the instrument 600 can be slid distally in relation to the instrument drive system 700 until the engagement member 620 couples with the instrument drive system 700.

At least portions of the handle 612 and the engagement member 620 extend farther radially than adjacent portions of the instrument drive system 700 while the instrument is coupled with the instrument drive system, so that handle 612 protrudes out of instrument drive system 700. Accordingly, the handle 612 and engagement member 620 are accessible to the hands of a user. Such accessibility can advantageously facilitate ready decoupling of the instrument 600 from the instrument drive system 700.

Although not visible, the instrument drive system 700 includes multiple actuators (schematically depicted in FIGS. 9 and 11-14) that releasably couple with the engagement members 632a, 632b, 634a, 634b, 636a, 636b, and 638 while the instrument 600 is coupled with the instrument drive system 700. In some embodiments, the actuators are linear actuators that include lead screws and lead screw nut members, and other suitable linear actuators (e.g., chain, belt, hydraulic, pneumatic, electromagnetic, and the like) may be used. In some embodiments, non-linear actuators such as rotary actuators, or combinations of linear and non-linear actuators, may be used to produce the antagonistic force aspects as described. In some embodiments, one or more force sensors are included in the instrument drive system 700 by which forces applied to the engagement members 632a, 632b, 634a, 634b, 636a, 636b, and/or 638 can be determined and fed back to the processor 43 (FIG. 2).

In some embodiments, the entirety of the instrument 600 coupled to the instrument drive system 700 can be rotated or rolled about the longitudinal axes 602 and 702 as a single unit. The engagement member 620, when coupled to instrument drive system 700 either via an instrument shaft insertion/withdrawal actuator or directly to instrument drive system 700, is used to secure the instrument shaft during roll around longitudinal axis 602 as instrument drive system 700 rotates around its longitudinal axis 702. In addition, handle 612 may provide extra support against instrument drive system 700 for roll. A motor at the distal end of instrument drive system 700, either inside instrument drive system 700 or part of manipulator assembly 800, rotates the assembly of instrument drive system 700 and instrument 600. Thus the instrument shaft, and the distal end effector, may be simultaneously inserted/withdrawn and rolled.

Figure 20:
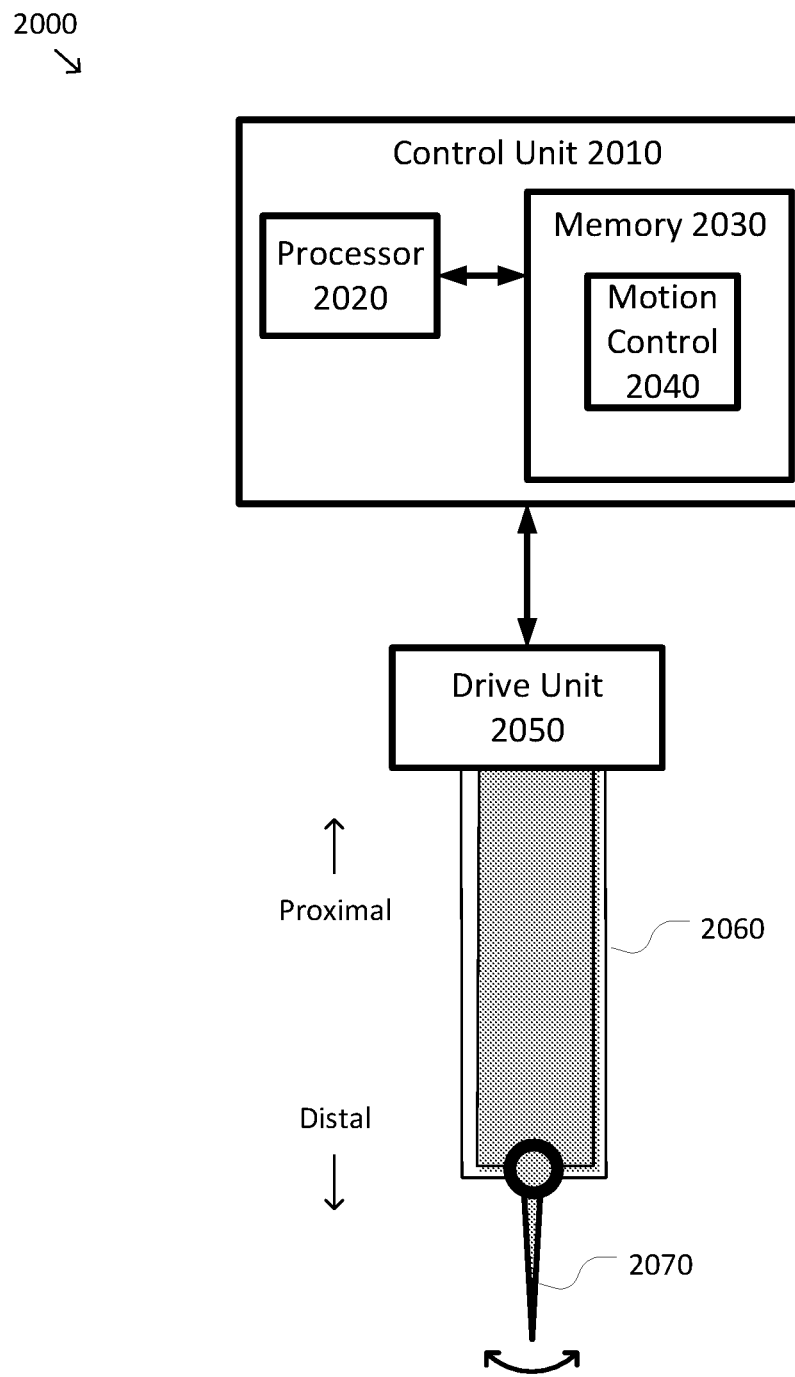
FIG. 20 depicts an end effector control system in accordance with some embodiments.

Referring to FIG. 20, an example end effector control system 2000 is depicted in accordance with some embodiments. As shown in FIG. 20, control system 2000 includes a control unit 2010. Control unit 2010 includes a processor 2020 coupled to memory 2030. In some embodiments, control unit 2010 and/or processor 2020 may be consistent with processor 43 of FIG. 2. Operation of control unit 2010 is controlled by processor 2020. And although control unit 2010 is shown with only one processor 2020, it is understood that processor 2020 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in control unit 2010. Control unit 2010 may be implemented as a stand-alone subsystem and/or as a board added to a computing device or as a virtual machine.

Memory 2030 may be used to store software executed by control unit 2010 and/or one or more data structures used during operation of control unit 2010. Memory 2030 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 2030 includes a motion control module 2040. Motion control module 2040 may support autonomous and/or semiautonomous control of one or more devices, one or more instruments, and/or one or more end effectors. Motion control module 2040 may additionally include one or more application programming interfaces (APIs) for receiving position, motion, and/or other sensor information from a device, instrument, and/or end effector being controlled, commands from an operator via an input control system (not shown), exchanging position, motion, and/or collision avoidance information with other control units regarding other devices, instruments, and/or end effectors, and/or planning and/or assisting in the planning of motion for the one or more devices, one or more instruments, and/or one or more end effectors. In addition, motion control module 2040 may provide commands to one or more actuators used to control positions and/or orientations of one or more degrees of freedom in the one or more devices, the one or more instruments, and/or the one or more end effectors. And although motion control module 2040 is depicted as a software module, motion control module 2040 may be implemented using hardware, software, and/or a combination of hardware and software.

One of the tasks of motion control module 2040 is to engage the one or more actuators with the corresponding one or more degrees of freedom being controlled. In some examples, the engagement includes making adjustments for variations among the mechanisms used to control the one or more degrees of freedom, wear and/or tear in the mechanisms, uncertainties in initial positions and/or orientations of the one or more degrees of freedom, and/or the like. Another task of motion control module 2040 is to actuate each of the one or more degrees of freedom to a known position and/or orientation (e.g., a home position and/or orientation) after the engagement is completed.

In order to perform the engagement and/or homing, control unit 2010 and motion control module 2040 are coupled to a drive unit 2050 using an interface. The interface may include one or more cables, connectors, and/or buses and may further include one or more networks with one or more network switching and/or routing devices. Drive unit 2050 includes the one or more actuators used to control each of the degrees of freedom and/or one or more sensors for monitoring the one or more actuators, tracking the one or more degrees of freedom, and/or the like.

An instrument having a shaft 2060 is coupled to drive unit 2050. Shaft 2060 may be used to introduce an end effector 2070 into a work site at a location distal to drive unit 2050. Use of shaft 2060 allows for operation of end effector 2070 in work sites where there is limited access (e.g., when the instrument is introduced into a work site through a small aperture, such as an incision site and/or natural orifice of a patient when the work site is a surgical or other medical work site). As shown in FIG. 20, end effector 2070 includes a degree of freedom that may be rotationally adjusted in the directions indicated by the double-headed arrow. And although FIG. 20 shows only a single degree of rotational freedom, it is understood that an end effector may have two, three, four, or more degrees of freedom including other rotational degrees of freedom, positional degrees of freedom, and/or the like.

Figure 21:
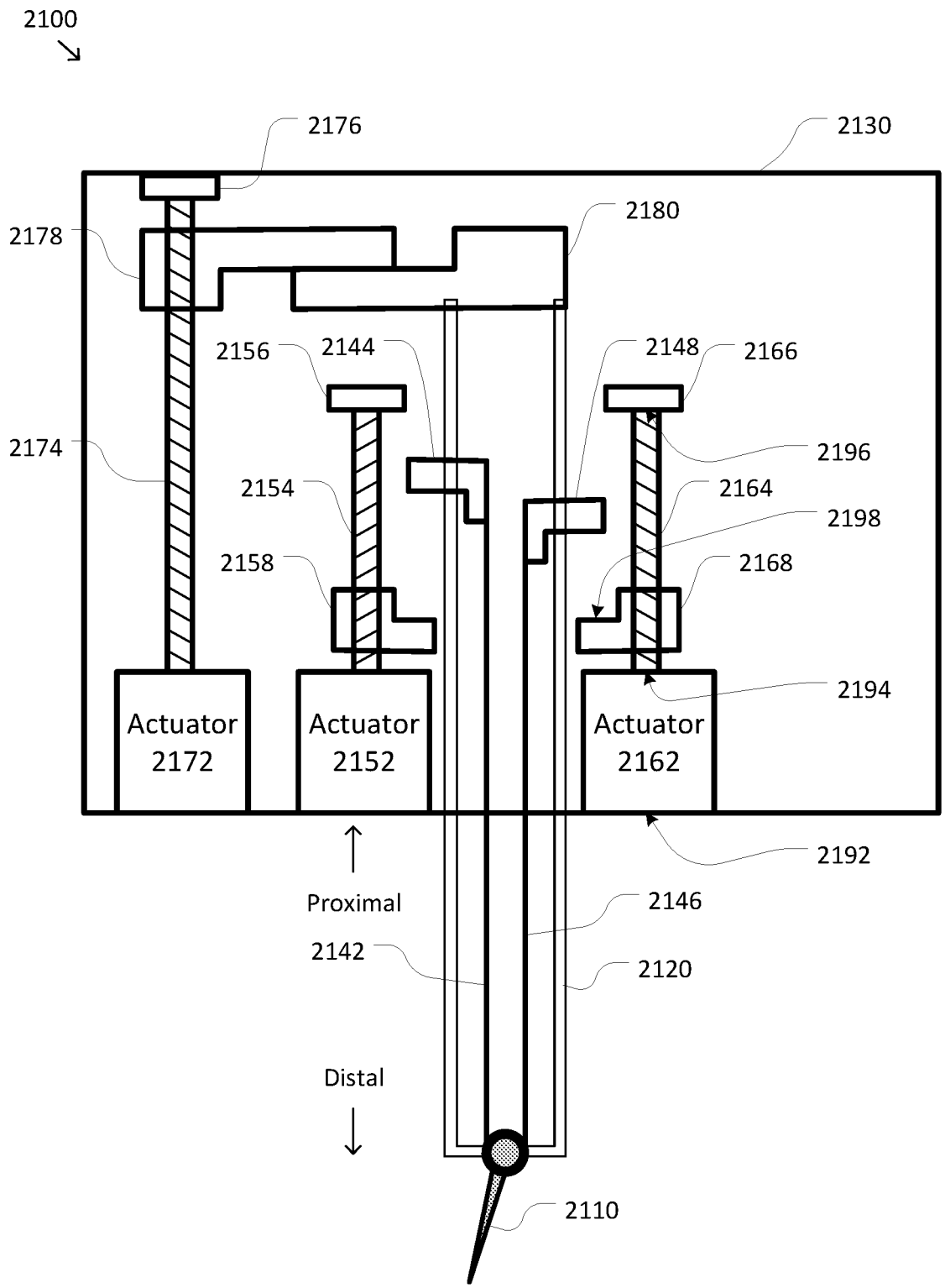
FIG. 21 depicts a drive unit and instrument prior to engagement in accordance with some embodiments.

Referring to FIG. 21, a system 2100 with an instrument having a controllable end effector 2110 is shown prior to engagement in accordance with some embodiments. As shown in FIG. 21, end effector 2110 is coupled via a shaft 2120 to a drive unit 2130. In some embodiments, end effector 2110 may be end effector 2070, shaft 2120 may be shaft 2060, and/or drive unit 2130 may be instrument drive system 700 and/or drive unit 2050. The instrument further includes a transmission mechanism 2142 coupling end effector 2110 to an engagement member 2144 located proximal to end effector 2110. As shown, movement of engagement member 2144 in a proximal direction by drive unit 2130 results in movement of a degree of freedom of end effector 2110 in a first direction. Similarly, the instrument further includes a transmission mechanism 2146 coupling end effector 2110 to an engagement member 2148 located proximal to end effector 2110. As shown, movement of engagement member 2148 in a proximal direction by drive unit 2130 results in movement of the degree of freedom of end effector 2110 in a second direction opposite the first direction in an antagonistic fashion. In some examples, transmission mechanisms 2142 and/or 2146 may perform a function similar to tensioning members 340 and/or 360. In some examples, transmission mechanisms 2142 and/or 2146 may each be a mechanism for transferring force or torque from drive unit 2130 to the degree of freedom of end effector 2110 and each may include a cable, a wire, a belt, a band, a chain, a shaft, and/or the like. In some examples, each of engagement members 2144 and/or 2148 may perform a similar function as engagement member 350, 370, 632a, 632b, 634a, 634b, 636a, 636b, and/or 638.

Drive unit 2130 includes an actuator 2152 mounted to drive unit 2130. In some examples, actuator 2152 is a motor and/or the like. Actuator 2152 is drivably coupled to a lead screw 2154 at a first end of lead screw 2154. A second end of lead screw 2154 is anchored to the housing of drive unit 2130 via a mounting member 2156 that allows rotation of lead screw 2154 by actuator 2152. As lead screw 2154 is rotated by actuator 2152, the rotation causes an engagement member 2158 to move along lead screw 2154. In some examples, engagement member 2158 is a threaded nut, such as treaded nuts 740a-h as described in further detail in International Patent Application No. PCT/US2017/51846. If engagement member 2158 is moved far enough along lead screw 2154, engagement member 2158 makes contact with engagement member 2144 and can be used to control movement of the degree of freedom of end effector 2110.

Drive unit 2130 further includes an actuator 2162 mounted to drive unit 2130. In some examples, actuator 2162 is a motor and/or the like. Actuator 2162 is drivably coupled to a lead screw 2164 at a first end of lead screw 2164. A second end of lead screw 2164 is anchored to the housing of drive unit 2130 via a mounting member 2166 that allows rotation of lead screw 2164 by actuator 2162. As lead screw 2164 is rotated by actuator 2162, the rotation causes an engagement member 2168 to move along lead screw 2164. In some examples, engagement member 2168 is a threaded nut, such as treaded nuts 740a-h as described in further detail in International Patent Application No. PCT/US2017/51846. If engagement member 2168 is moved far enough along lead screw 2164, engagement member 2168 makes contact with engagement member 2148 and can be used to control movement of the degree of freedom of end effector 2110.

Drive unit 2130 further includes an actuator 2172 mounted to drive unit 2130. In some examples, actuator 2172 is a motor and/or the like. Actuator 2172 is drivably coupled to a lead screw 2174 at a first end of lead screw 2174. A second end of lead screw 2174 is anchored to the housing of drive unit 2130 via a mounting member 2176 that allows rotation of lead screw 2174 by actuator 2172. As lead screw 2174 is rotated by actuator 2172, the rotation causes an engagement member 2178 to move along lead screw 2174. In some examples, engagement member 2178 is a threaded nut, such as treaded nuts 740a-h as described in further detail in International Patent Application No. PCT/US2017/51846. If engagement member 2178 is moved far enough along lead screw 2174, engagement member 2178 makes contact with an engagement member 2180 located at the end of shaft 2120 opposite end effector 2110 and can be used to help control insertion and/or retraction of shaft 2120 and end effector 2110 relative to drive unit 2130.

Drive unit 2130 may additionally include one or more sensors that may be used to monitor actuators 2152, 2162, and/or 2172, the locations of engagement members 2158, 2168, and/or 2178, engagement between engagement members 2158, 2168, and/or 2178 with engagement members 2144, 2148, and/or 2180, respectively, and/or the like. In some examples, signals from one or more force and/or torque sensors may be used to estimate an amount of force and/or torque being applied by a respective engagement member 2144, 2148, and/or 2180 to a corresponding engagement member 2158, 2168, or 2178. Possible locations for the one or more force and/or torque sensors include any portion where the force and/or torque is transmitted, and some possible locations are indicated by arrows 2192-2198 for engagement member 2168, with engagement members 2158 and/or 2178 having similar possible locations. As shown, location 2192 is between an end of actuator 2162 opposite lead screw 2164 and the housing of drive unit 2130. Location 2194 is where lead screw 2164 is coupled to actuator 2162. Location 2196 is located where lead screw 2164 is coupled to mounting member 2166 or alternatively between mounting member 2166 and the housing of drive unit 2130. Location 2198 is on a surface of engagement member 2168 where engagement member 2168 makes contact with engagement member 2148. In some examples, other locations are possible. In some examples, multiple force and/or torque sensors may be used at any combination of locations. In some examples, the forces or torques measured by each of the force and/or torque sensors may be aggregated to estimate the force or torque applied by the respective engagement member (the engagement member being moved by an actuator of the drive unit) to the corresponding engagement member of the instrument. In some examples, the aggregation may be a weighted sum, such as an average. In some examples, each of the one or more force and/or torque sensors may include a strain gauge, a pressure transducer, a force transducer, a piezoelectric device, and/or the like.

In some embodiments, other type of sensors may be used to monitor actuators 2152, 2162, and/or 2172, the locations of engagement members 2158, 2168, and/or 2178, and/or the like. In some examples, one or more position and/or speed/velocity sensors located at, for example, location 2194 may be used to track a position and/or velocity of lead screw 2164 and/or engagement member 2168 along lead screw 2164. In some examples, one or more proximity and/or contact sensors located at, for example, location 2198 may be used to detect proximity and/or contact between engagement member 2168 and engagement member 2148. In some examples, the one or more proximity and/or contact sensors may include mechanical, resistive, or capacitive switches, pressure transducers, strain gauges, Hall Effect sensors, RFID devices, and/or the like.

FIG. 21 shows a configuration of system 2100 before drive unit 2130 is engaged with end effector 2110. More specifically, FIG. 21 shows engagement members 2158 and 2168 moved, respectively, along lead screws 2154 and 2164 toward actuators 2152 and 2162 so as to reduce the likelihood of undesirable contact between engagement member 2158 and engagement member 2144 and/or between engagement member 2168 and engagement member 2148 when the instrument is mounted to drive unit 2130 and/or to help address the possible unknown location of engagement member 2144 and/or engagement member 2148. Engagement member 2178 is moved along lead screw 2174 away from actuator 2172 and is further shown in contact with engagement member 2180 as a result of mounting the instrument to drive unit 2130. In some examples, engagement member 2178 may additionally be moved along lead screw 2174 until engagement member 2178 contacts engagement member 2180. In the configuration of FIG. 21, engagement between engagement member 2158 and engagement member 2144 and engagement between engagement member 2168 and engagement member 2148 has not occurred and control of the degree of freedom of end effector 2110 using actuators 2152 and 2162 is not yet possible. Further, as a result of the lack of engagement, the position of the degree of freedom of end effector 2110 may not be known and may further not be in a default, centered, and/or homed position.

As discussed above and further emphasized here, FIG. 21 is merely an example which should not unduly limit the scope of the claims. One of ordinary skill in the art would recognize many variations, alternatives, and modifications. According to some embodiments, the engagement between engagement member 2178 and engagement member 2180 may include other and/or different components than those shown in FIG. 21. In some examples, engagement member 2178 and/or engagement member 2180 may each include a hook, tab, clip, latch, and/or the like so that engagement member 2178 and engagement member 2180 are coupled in a detained fashion (see, e.g., engagement member 620 of FIG. 16) when the instrument is attached to drive unit 2130.

According to some embodiments, drive unit 2130 and the instrument may include additional components that are not shown. In some examples, engagement members 2144 and/or 2148 may have a limited range of motion. In some examples, the motion may be limited by slots similar to the longitudinal slots of FIG. 16. In some examples, engagement members 2144 and/or 2148 may each be associated with one or more pre-tensioning and/or pre-positioning elements, such as springs 633 of FIG. 16 to control a position of respective engagement members 2144 and/or 2148 and/or slack in respective transmission mechanisms 2142 and/or 2146.

Figure 22:
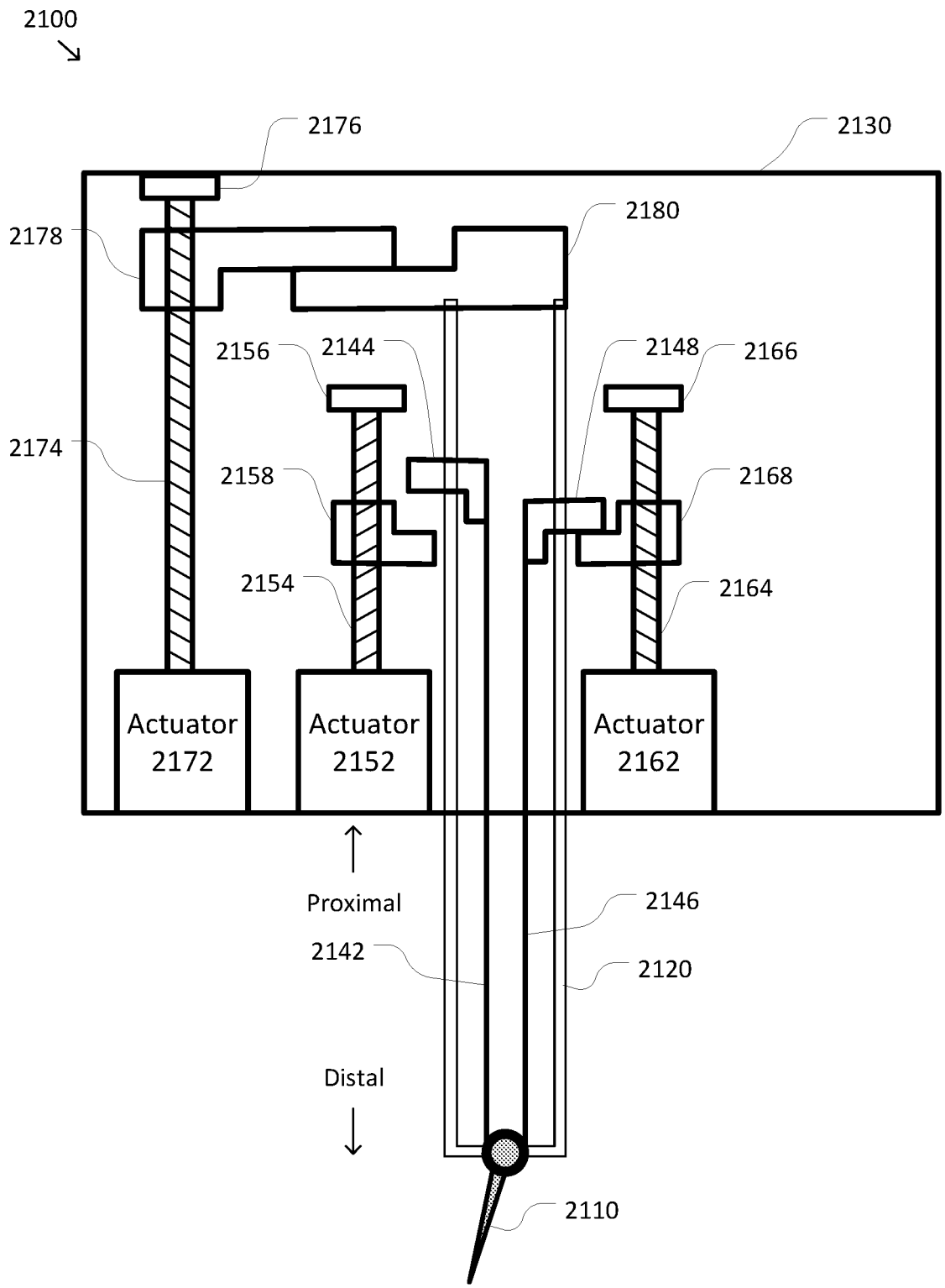
FIG. 22 depicts the drive unit and instrument of FIG. 21 after partial engagement in accordance with some embodiments.

Referring to FIG. 22, the configuration of system 2100 is shown after partial engagement in accordance with some embodiments. As shown actuator 2152 has been actuated and engagement member 2158 is moved along lead screw 2154 toward engagement member 2144. Similarly, actuator 2162 has been actuated and engagement member 2168 is moved along lead screw 2164 and has just made contact with engagement member 2148. At this point during the engagement process, actuation of actuator 2162 may change so as to maintain engagement member 2168 at the position along lead screw 2164 where engagement member 2168 contacted engagement member 2148. Alternatively, further actuation of actuator 2162 occurs to continue moving engagement member 2168 along lead screw 2164; this further actuation, if not counteracted, causes further movement of engagement member 2148 and possible movement of the degree of freedom of end effector 2110 once any slack and/or give in transmission mechanism 2146 and/or any gap between engagement member 2178 and/or engagement 2180 is taken up. In some examples, a physical stop (not shown) provides a position limit for engagement member 2148, and engagement member 2168 is limited from moving engagement member 2148 past this physical stop. In some examples, one or more biasing components such as compression springs, extension springs, constant force springs, elastomeric bands, and/or the like provide a counteracting force against the movement of engagement member 2148 and/or engagement member 2168. In some examples, such biasing component may be coupled to provide counteracting force continuously or may be configured to provide counteracting force only within a certain position range of engagement member 2148 and/or engagement member 2168. In some examples, such biasing component may be configured to provide counteracting forces that help retain engagement member 2148 and/or engagement member 2168 in a position range. In some examples, such biasing components may be located parallel to transmission mechanism 2146 or placed in series with transmission mechanism 2146, and/or used to tune the compliance of the transmission system. As a specific example, springs coupled in series with transmission mechanism 2146 may be used to increase the compliance of the transmission system including transmission mechanism 2146. In some examples, one or more dampers are placed in series or in parallel with transmission mechanism 2146 to provide counteracting damping force. In some examples, an amount of motion of actuator 2162 and/or engagement member 2148 and/or engagement member 2168 (or a position of actuator 2162 and/or engagement member 2148 and/or engagement member 2168) may be monitored in order to stop actuation before a motion limit of engagement member 2168 and/or engagement member 2148 is reached.

Figure 23:
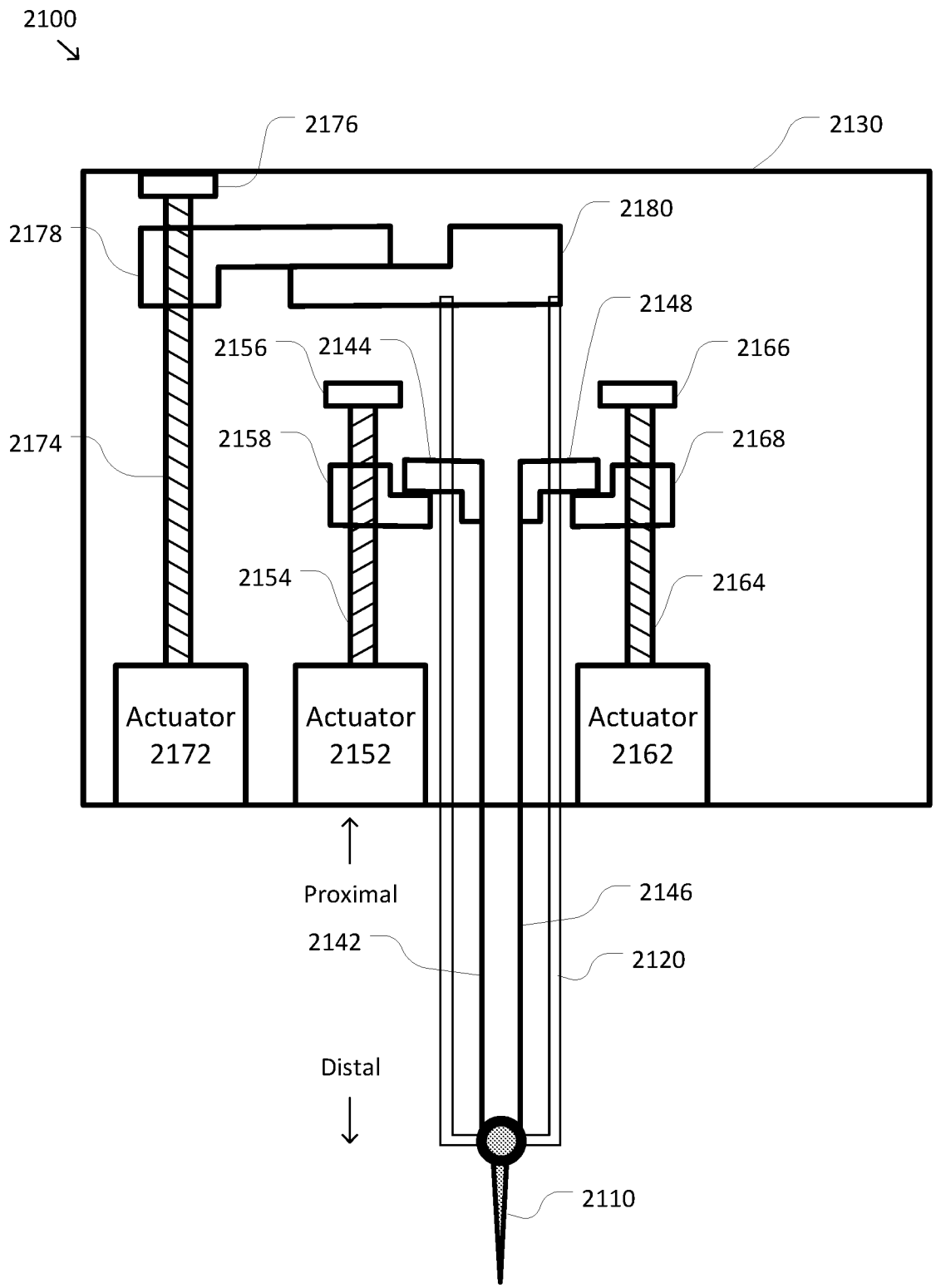
FIG. 23 depicts the drive unit and instrument of FIG. 21 after engagement in accordance with some embodiments.

Referring to FIG. 23, the configuration of system 2100 is shown after engagement in accordance with some embodiments. As shown actuator 2152 has been actuated and engagement member 2158 is moved along lead screw 2154 and has made contact with engagement member 2144. Engagement member 2168 continues to make contact with engagement member 2148. The degree of freedom of end effector 2110 has also moved as a result of movement of engagement member 2148 by engagement member 2168 due to continued movement of engagement member 2168 along lead screw 2164. In some examples, actuators 2152 and/or 2162 may continue to be actuated so as to further move engagement member 2158 along lead screw 2154 and engagement member 2168 along lead screw 2164 until a pre-tension level is reached by both actuator 2152 and actuator 2162 indicating that any slack and/or give in transmission mechanisms 2142 and 2146 is taken up. In some examples, each of actuator 2152 and/or actuator 2162 may reach the pre-tension level by commanding movement of actuator 2152 and/or actuator 2162 subject to a pre-tension force or torque limit. In some examples, the pre-tension force or torque limit may be implemented by limiting drive current in each of actuator 2152 and/or actuator 2162 to a corresponding current limit.

As a further consequence of the configurations in FIGS. 21-23, actuators 2152 and 2162 and the rest of the corresponding elements control the degree of freedom of end effector 2110 in antagonistic fashion similar to the antagonistic control described with respect to FIGS. 8-14. Thus, the movement of the degree of freedom of end effector 2110 depends on the relative forces and/or torques applied by actuators 2152 and 2162 once engagement member 2158 engages with engagement member 2144 and engagement member 2168 engages with engagement member 2148. Additionally, actuators 2152, 2162, and 2172 and the rest of the corresponding elements control insertion and/or retraction of shaft 2120 and end effector 2110 relative to drive unit 2130 in a fashion similar to that described with respect to FIGS. 10-13.

Although not shown in FIGS. 21-23, actuators 2152, 2162, and/or 2172 are each coupled to one or more corresponding control signals that are used to control rotation of the respective actuator. In some examples, the one or more control signals may be provided by a control unit (e.g., control unit 2010) and/or a motion control module (e.g., motion control module 2014). In some examples, the one or more control signals may correspond to one or more voltages, one or more currents, one or more pulse-width modulated signals, and/or the like.

Although FIGS. 21-23 depict control of end effector 2110 using rotational actuators (e.g., motors) and lead screws, other mechanisms may be used. In some examples, one or more of lead screws 2154, 2164, and/or 2174 may be replaced with other types of rotational to linear motion converters. In some examples, one or more of actuators 2152, 2162, and 2172 may be replaced by servos, hydraulic, electromagnetic, and/or pneumatic solenoids, pistons, and/or the like. In some examples, one or more of lead screws 2154, 2164, and/or 2174 may be replaced by cables, belts, bands, chains, shafts, and/or the like.

Although FIGS. 21-23 depict the relative orientation of actuators 2152, 2162, and/or 2172 and their corresponding lead screws, etc. as being coplanar, this orientation is not the only possible relative orientation. In some examples, each of actuators 2152, 2162, and 2172 may be located at different angular positions around shaft 2120, such as is shown in International Patent Application No. PCT/US2017/51846.

Figure 24:
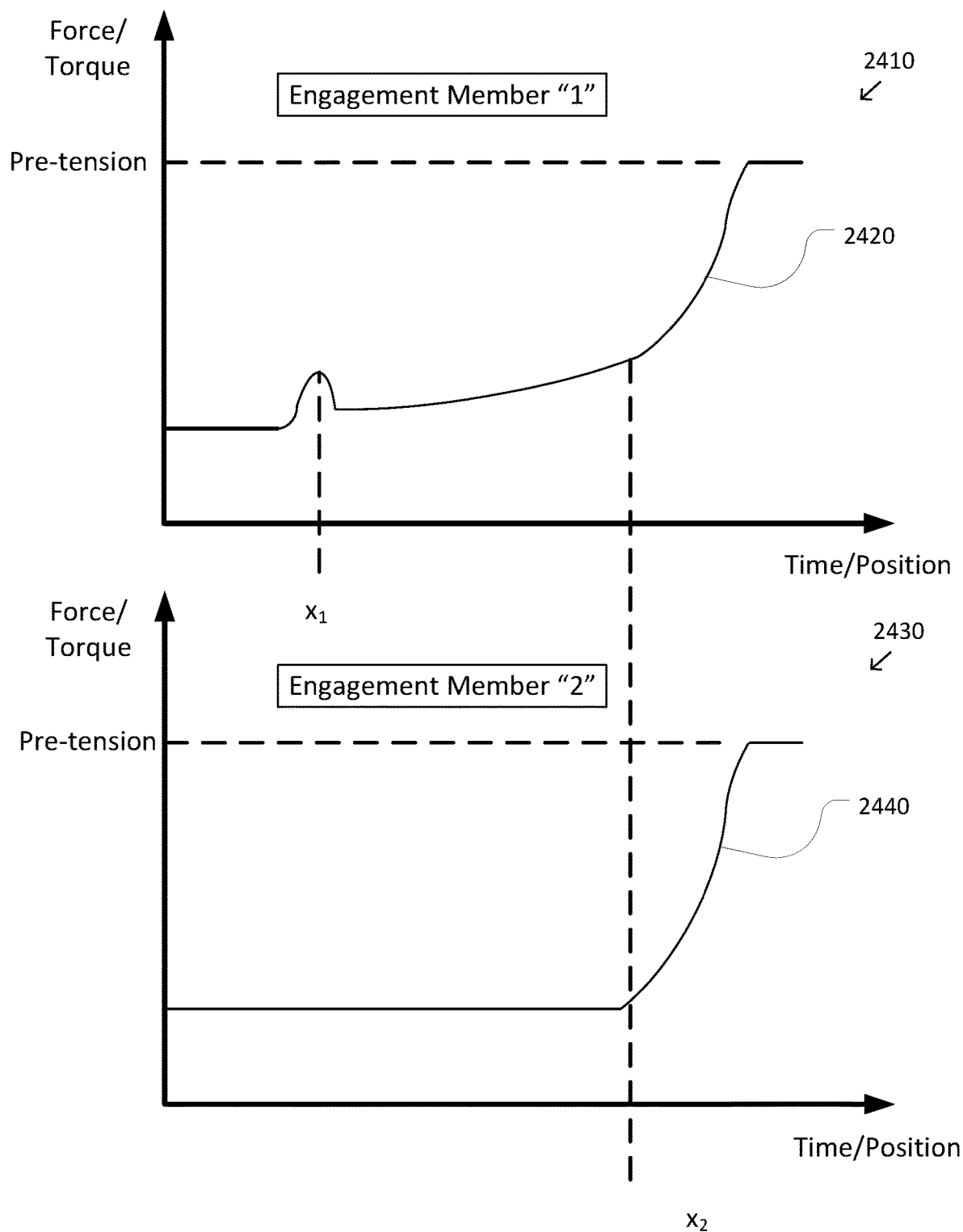
FIG. 24 depicts force and/or torque profiles during an engagement process in accordance with some embodiments.

Referring to FIG. 24, examples of force and/or torque profiles representative of engagement between two pairs of engagement members during an engagement process are shown in accordance with some embodiments. As shown FIG. 24 includes a force and/or torque profile 2410 representative of a force and/or torque being exerted to move a first engagement member and a force and/or torque profile 2430 representative of a force and/or torque being exerted to move a second actuator. In some examples, these force/torque profiles 2410 and/or 2430 represent the forces applied by engagement members to other engagement members (e.g. engagement members 2168 and 2148). In the examples of FIGS. 21-23, the first engagement member may correspond to engagement member 2168 and the second engagement member may correspond to engagement member 2158. Each of profiles 2410 and 2430 is representative of a force and/or torque used to engage an engagement member (e.g., engagement member 2158 and/or 2168) with a corresponding engagement member (e.g., engagement member 2144 and/or 2148) of an instrument and coupled to a degree of freedom of an end effector. In some examples, profiles 2410 and 2430 are consistent with the antagonistic control of a degree of freedom as described with respect to FIGS. 21-23. In profiles 2410 and 2430 the horizontal axis corresponds to either a position of the engagement member being moved by the actuator and/or a time since the beginning of the engagement process and the vertical axis corresponds to a force and/or torque associated with the corresponding engagement member. In some examples, the force and/or torque may be determined using one or more sensors, such as the force and/or torque sensors described with respect to FIG. 21.

As shown, the engagement process begins with both actuators being actuated to move its corresponding engagement member. In some examples, this actuation may include position control where each actuator begins moving its engagement member to a far end of its lead screw in the direction of engaging and/or velocity control where each actuator begins moving its engagement member at a configurable velocity away from the actuator. In some examples, the actuator may be further constrained by a configurable actuation threshold, such as a force, torque, and/or current limit to prevent driving its engagement member with excessive force and/or torque. In some examples, the pre-tension force, torque, and/or current limit may be set based on one or more of a type of instrument and/or end effector being engaged with, a type of drive unit, operator preference, a desired lifetime and/or number of procedures to be performed by the instrument and/or the end effector, anticipated force, torque, current and/or the like to be used to actuate the end effector, and/or the like. In some examples, the pre-tension force may be set to a value between 4 Newtons and 30 Newtons. In some examples, the force, torque, and/or current limit may correspond to the pre-tension value indicated on profiles 2410 and 2430.

During a first stage of the engagement process, neither of the engagement members has contacted the corresponding engagement member used to control the degree of freedom of the end effector. During this first stage an approximately constant amount of force and/or torque is used to overcome friction and/or inertia and to move the corresponding engagement member along its lead screw. This is shown by the flat left (initial) end of corresponding force and/or torque curves 2420 and 2440. In some embodiments, the initial end of the corresponding force and/or torque curves 2420 and/or 2440 may not be approximately constant and may follow a different profile. In some examples, the different profile may be due to changes in speed at which the two actuators are actuated, changes in and/or non-linear characteristics as the corresponding engagement member moves along its lead screw (e.g., a change in friction based on position along the lead screw), and/or the like.

At or near time/position $x_1$, the first engagement member makes contact with the corresponding engagement member of the instrument. As the first engagement member begins to make contact with the corresponding engagement member of the instrument, the force and/or torque associated with the first engagement member begins to rise as any slack and/or give in the transmission mechanism (e.g., transmission mechanism 2142 and/or 2146) it taken up and/or static friction and/or inertia of the instrument is overcome. After an initial increase in force (e.g., of 0.25 Newtons to 2.0 Newtons) and/or torque, the force and/or torque associated with the first engagement member typically decreases. As shown, the decrease in force and/or torque is not as large as the initial increase as movement of the engagement member of the instrument and corresponding motion of the transmission mechanism and the degree of freedom takes additional force and/or torque to sustain due to dynamic friction, mass, and/or the like of the corresponding transmission mechanism 2142 or 2146 and/or end effector 2110. In some examples, other factors such as one or more of changes in speed at which the corresponding actuator is actuated, changes in and/or non-linear characteristics as the corresponding engagement member moves along its lead screw, and/or the like.

In some embodiments, this initial increase in force and/or torque may be used to detect the contact and engagement between the first engagement member and the corresponding engagement member of the instrument. In some examples, the initial increase may be identified based on a shape and/or or one or more characteristics of force and/or torque curve 2420 (e.g., any combination of a value, a rate of change/velocity/first derivative, an acceleration/second derivative, and/or the like) in the temporal domain or spatial domain. In some examples, the initial increase may be identified based on the force and/or torque exceeding a configurable force or torque threshold, a force or torque threshold based on a configurable percentage of the force and/or torque observed before the initial increase, a rate of increase in the force and/or torque, an amount of inflection in the force and/or torque, a pattern of rapid increase followed by partial decrease, a frequency signature in the frequency spectrum of the force and/or torque, and/or the like, and/or any combination thereof. In some examples, any suitable change in the temporal, spatial, and/or frequency pattern of the force and/or torque may be used to identify the change in the force and/or torque at time/position $x_1$.

In some examples, a piezoelectric transducer may measure higher frequency content in the estimate of force or pressure when the first engagement member makes contact with the third engagement member. In some examples, experiments may be used to determine the frequency response of this estimated signal to create an expected pattern. In some examples, this pattern may be stored in memory on the processor as a discretized look up table and/or parameters from which an analytical function approximation may be determined. During engagement, the frequency response of the force signal is analyzed and compared against the expected pattern using any of the pattern matching techniques known in the art. In some examples, a force sensor may measure the contact of the first engagement member with the third engagement member. In some examples, a frequency response estimator may be used to determine the power contribution in various frequency bands. Frequency bands may be chosen based on knowledge of the sensor bandwidth and/or mechanical resonances of the drive mechanism. In some examples, a contact of the type (characterized potentially by impact loads) shown at time/position $x_1$, may correspond to higher power contribution from higher frequency bands.

As the engagement process continues, the second actuator continues to move the second engagement member along the corresponding lead screw at an approximately constant force and/or torque value as shown in force and/or torque curve 2440. This occurs irrespective of whether the first actuator continues to move the first engagement member or servos it in place. As shown in FIG. 24, the force and/or torque profile for the first actuator continues to gradually increase indicating that the first actuator is continuing to move the first engagement member between time/position $x_1$ and time/position $x_2$. At or near time/position $x_2$, the second engagement member makes contact with its corresponding engagement member of the instrument. And as the slack and/or give in the transmission mechanism is taken up, the second actuator begins to operate antagonistically against the first actuator as both the first and second actuators attempt to move the corresponding degree of freedom in different directions. As a result, the force and/or torque associated with both the first and second engagement members begin to increase at approximately the same rate.

Thus, the contact and/or engagement between the second engagement member and its corresponding engagement member of the instrument may be detected by noting an increase in the force and/or torque associated with both the first and the second engagement members. In some examples, the increase may be identified based on a shape and/or or one or more characteristics of force and/or torque curves 2420 and 2440 (e.g., any combination of a value, a rate of change/velocity/first derivative, an acceleration/second derivative, and/or the like). In some examples, the increase may be identified based on each force and/or torque exceeding a configurable force or torque threshold, a force or torque threshold based on a configurable percentage of the force and/or torque observed before the increase, a rate of increase in the force and/or torque, an amount of inflection in the force and/or torque, a pattern of rapid increase, and/or the like, and/or any combination thereof. In some examples, any suitable change in the temporal, spatial, and/or frequency pattern of the force and/or torque associated with both the first and second engagement members may be used to identify the change in the force and/or torque at time/position $x_2$.

As shown, the first and second actuators continue to further actuate the first and second engagement members, respectively until the force and/or torque profiles reaches a configurable pre-tension force and/or torque threshold. In some examples, each configurable pre-tension force and/or torque threshold may be obtained by actuating each of the first and second actuators subject to a corresponding force, torque, and/or current limit. Once the pre-tension force and/or torque is reached, the force and/or torque associated with each of the first and second engagement members levels out.

As discussed above and further emphasized here, FIG. 24 is merely an example which should not unduly limit the scope of the claims. One of ordinary skill in the art would recognize many variations, alternatives, and modifications. According to some embodiments, the engagement between the first and/or second engagement members and the corresponding engagement members of the instrument may be detected using other metrics than force and/or torque. In some examples, a position of the corresponding actuator may be monitored to detect corresponding changes in the position of the actuator over time as indicated by the velocity, acceleration, and/or other characteristics of the positions. In some examples, an error between a commanded position of the actuator and an actual position of the actuator may indicate that the contact between the engagement members is interfering with the ability of the actuator to actuate to the desired position and/or at the desired speed. In some examples, a reduction in speed of the first actuator and the corresponding speed at which its engagement member is moved may show a temporary decrease at or near $x_1$ and both the first and second actuator may have a more sustained reduction in speed at or near $x_2$. In some examples, these corresponding speed profiles may exhibit decreases similar to the corresponding increases in curves 2420 and 2440. In some examples, contact and/or proximity sensors may be used to detect the contact between the corresponding engagement members. In some examples, combinations of two or more of the force and/or torque, speed, and/or contact/proximity may be used to detect the engagement.

Figure 25:
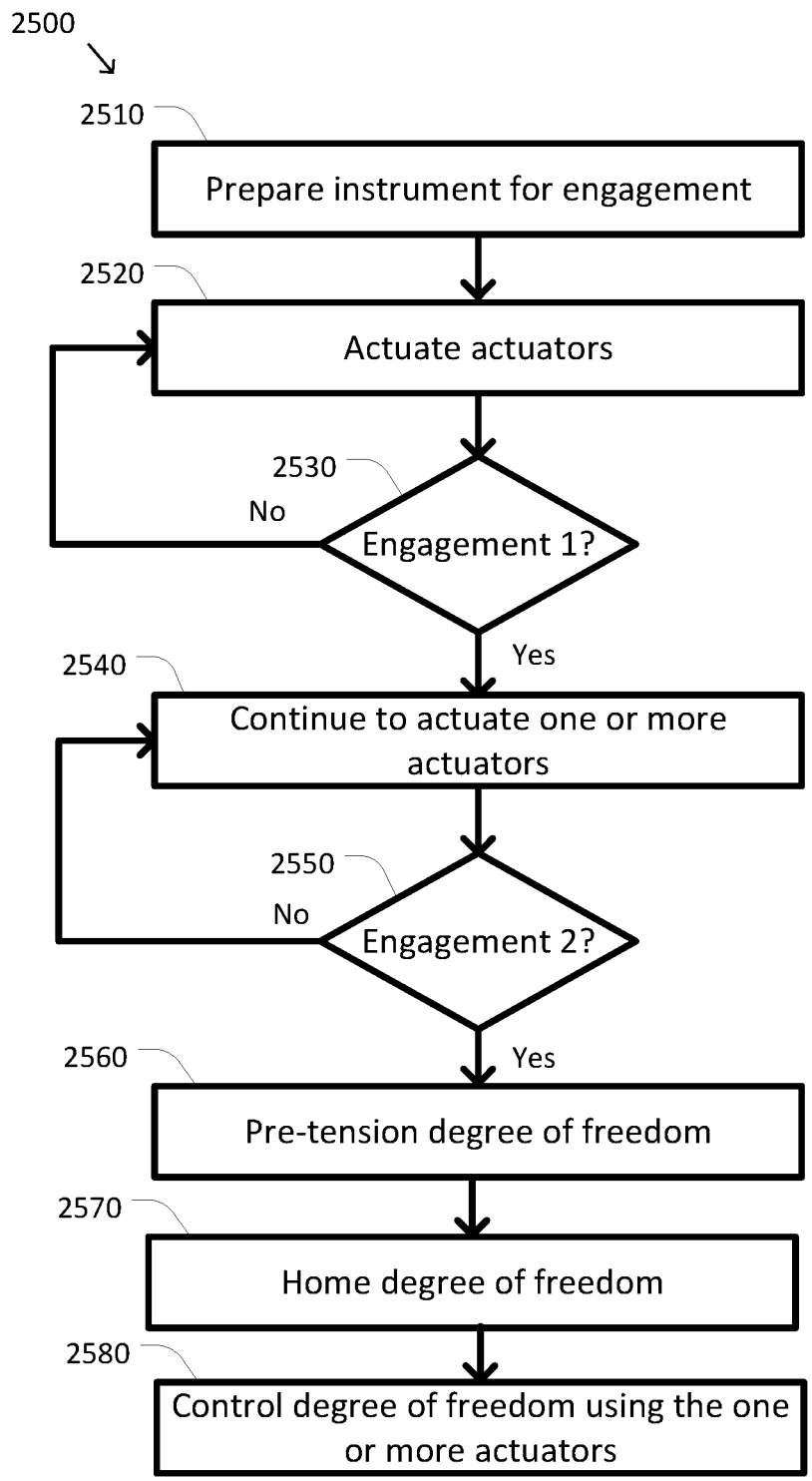
FIG. 25 depicts a method of engagement in accordance with some embodiments.

Referring to FIG. 25, a method 2500 of engagement in accordance with some embodiments is shown. One or more of the processes 2510-2580 of method 2500 may be implemented, at least in part, in the form of executable code stored on non-transitory, tangible, machine-readable media that when run by one or more processors (e.g., processor 2020 in control unit 2010) may cause the one or more processors to perform one or more of the processes 2510-2580. In some embodiments, method 2500 may be performed by a module, such as motion control module 2040. In some examples, method 2500 may be used to control actuators 2152 and 2162 of drive unit 2130 as shown in FIGS. 21-23, which are used to antagonistically control the degree of freedom of end effector 2110. In some embodiments, process 2570 is optional and may be omitted.

At a process 2510, an instrument is prepared for engagement. In some examples, before engagement can occur the instrument is attached to a drive unit, such as drive unit 2130. In some examples, any gap between a pair of engagement members, such as engagement members 2178 and 2180, which are used to move a shaft of the instrument in an insertion direction is removed. In some examples, the gap may be removed when the instrument is attached to the drive unit when the pair of engagement members is coupled in a detained fashion. In some examples the gap may be removed by moving the engagement member (e.g., engagement member 2178) of the drive unit to its retraction end of travel, attaching the instrument to the drive unit, and moving the engagement member of the drive unit until it engages with the engagement member of the instrument. In some examples, one or more of a force, a torque, a current, a position, a speed, a position error, and/or the like associated with the engagement member of the drive unit, a contact and/or proximity sensor associated with the engagement member of the drive unit, and/or the like. may be used to detect this engagement. In some examples, process 2510 may further place the drive unit and instrument in an engagement mode. In some examples, at the end of process 2510, drive unit 2130, actuators 2152 and 2162, and engagement members 2158, 2168, 2144, and 2148 may be in the configuration as shown in FIG. 21.

At a process 2520, the actuators used to control a degree of freedom of an end effector are concurrently actuated. In some examples, the actuators correspond to actuators 2152 and 2162. The actuators are actuated so as to move and/or drive corresponding first and second engagement members (e.g., engagement members 2158 and 2168) from a position near a corresponding actuator to a position away from the corresponding actuator. In some examples, this actuation may include position control where each actuator begins moving its engagement member to a far end of its lead screw and/or a velocity control where each actuator begins moving its engagement member at a configurable velocity away from the actuator. In some examples, the actuator may be further constrained by a configurable force, torque, and/or current limit to prevent driving its engagement member with excessive force and/or torque. In some examples, the force, torque, and/or current limit may correspond to a corresponding pre-tension value. In some examples, process 2520 corresponds to the period before time/period $x_1$ in FIG. 24.

At a process 2530, it is determined whether a first one of the actuators has moved a first corresponding engagement member so that it is engaged with a third corresponding engagement member (e.g., engagement member 2144 or 2148) of the instrument used to control the degree of freedom. In some examples, the engagement between the first engagement member and the third engagement member may be detected based on any combination of one or more of a force, a torque, a current, a position, a speed, a position error, and/or the like associated with the first engagement member, a contact and/or proximity sensor associated with the first engagement member, and/or the like. In some examples, the engagement between the first engagement member and the third engagement member may be detected as described with respect to detecting the changes in curve 2420 at time/position $x_1$. When engagement between the first engagement member and the third engagement member is not yet detected, the actuators continue to be actuated by returning to process 2520. When engagement between the first engagement member and the third engagement member is detected, further actuation occurs beginning with a process 2540.

At the process 2540, actuation of one or more of the actuators continues. In some examples, the actuation of process 2520 continues with both actuators being actuated so as to cause further movement and/or driving of both the first engagement member and the second engagement member. In some examples, actuation of the first actuator is stopped and actuation of the second actuator continues. In some examples, stopping actuation of the first actuator may include servoing the position of the first actuator to a current position of the first actuator and correspondingly the first engagement member. In some examples, the servoing may include setting a position set point for the first actuator at the current position, setting a velocity set point of first actuator to zero, and/or the like. In some examples, the first actuator may continue to be constrained by the corresponding force, torque, and/or current limit. In some examples, process 2540 may correspond to the period between time/period $x_1$ and time/period $x_2$ of FIG. 24 and/or the configuration of FIG. 22.

At a process 2550, it is determined whether the second engagement member has engaged with a fourth corresponding engagement member (e.g., engagement member 2144 or 2148) of the instrument used to control the degree of freedom. In some examples, the engagement between the second engagement member and the fourth engagement member may be detected based on any combination of one or more of a force, a torque, a current, a position, a speed, a position error, and/or the like associated with both the first and second engagement members, contact and/or proximity sensors associated with the first and second engagement members, and/or the like. In some examples, the engagement between the second engagement member and the fourth engagement member may be detected as described with respect to detecting the changes in curves 2420 and 2440 at time/position $x_2$. When engagement between the second engagement member and the fourth engagement member is not yet detected, the one or more actuators continue to be actuated by returning to process 2540. When engagement between the second engagement member and the fourth engagement member is detected, further control occurs beginning with a process 2560.

At the process 2560, pre-tensioning of the degree of freedom is performed. In some examples, the force and/or torque associated with both the first and second actuators is increased until each reaches a configurable pre-tension value. In some examples, the pre-tensioning increases the likelihood that any slack and/or give in the transmission mechanisms used to control the degree of freedom are taken up. In some examples, the pre-tensioning provides actuation forces to counteract actuation forces used to control an insertion and/or retraction of the instrument (e.g., the actuation provided by actuator 2172). In some examples, the pre-tension may be performed by setting the force, torque, and current limit of the first and section actuators to the configurable pre-tension value and continuing actuation similar to the actuation of processes 2520 and/or 2540 until further movement of both the first and second actuators is constrained by the corresponding force, torque, and/or current limit. In some examples, the pre-tensioning may correspond to the configuration of FIG. 23.

Figure 26:
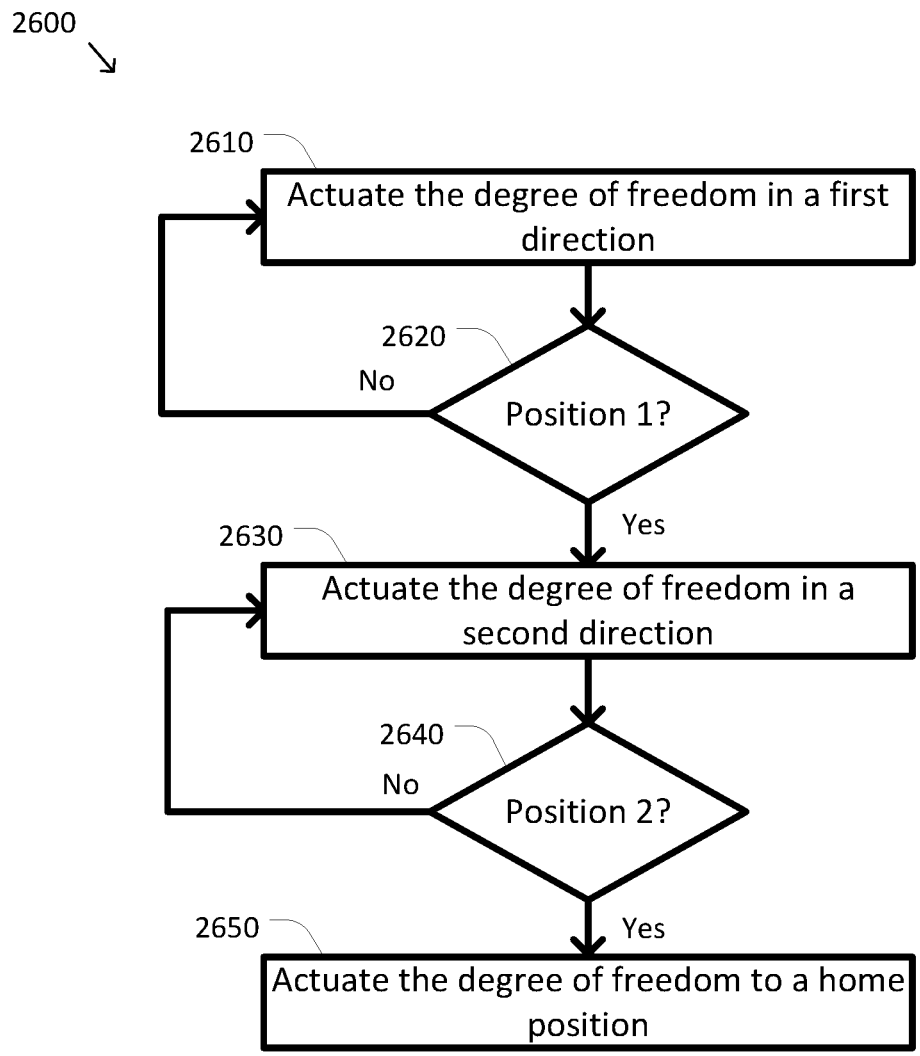
FIG. 26 depicts a method of homing a degree of freedom of an end effector in accordance with some embodiments.

At an optional process 2570, the degree of freedom being controlled by the first and second actuators is homed. In some examples, because of variations between end effectors, wear and tear on the end effectors, and/or the like, when the pre-tensioning of process 2560 is complete the actual location of the degree of freedom is not known. The homing of process 2570 allows the location of the degree of freedom to be known with greater certainty. In some examples, the degree of freedom may be homed according to a method 2600 as shown in FIG. 26. One or more of the processes 2610-2650 of method 2600 may be implemented, at least in part, in the form of executable code stored on non-transitory, tangible, machine-readable media that when run by one or more processors (e.g., processor 2020 in control unit 2010) may cause the one or more processors to perform one or more of the processes 2610-2650. In some embodiments, method 2600 may be performed by a module, such as motion control module 2040. In some examples, method 2600 may be used to control actuators 2152 and 2162 of drive unit 2130 as shown in FIGS. 21-23, which are used to antagonistically control the degree of freedom of end effector 2110. In some examples, method 2600 may begin with drive unit 2130, actuators 2152 and 2162, engagement members 2158, 2168, 2144, and 2148 in the configuration as shown in FIG. 23. In some examples, method 2600 may begin after an instrument whose end effector is being manipulated is attached to a cannula.

Figure 27C:
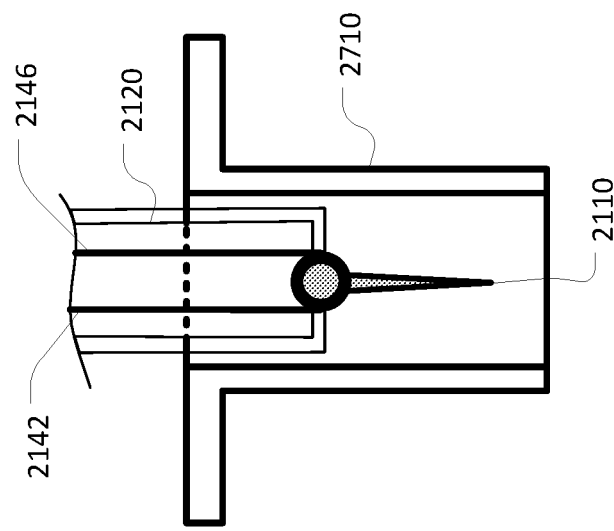
FIGS. 27A-27C depict an end effector during a homing method in accordance with some embodiments.
Figure 27B:
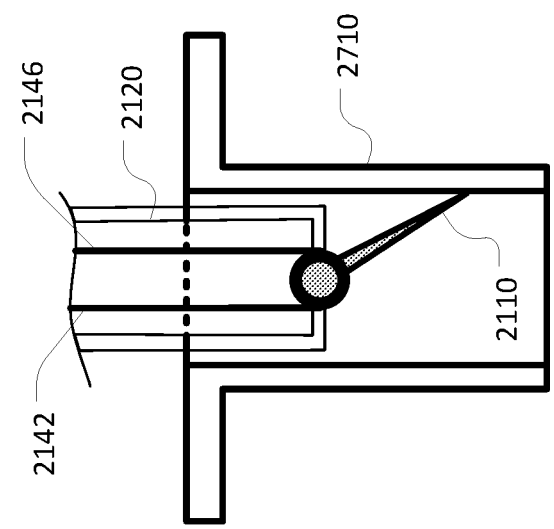
Figure 27A:
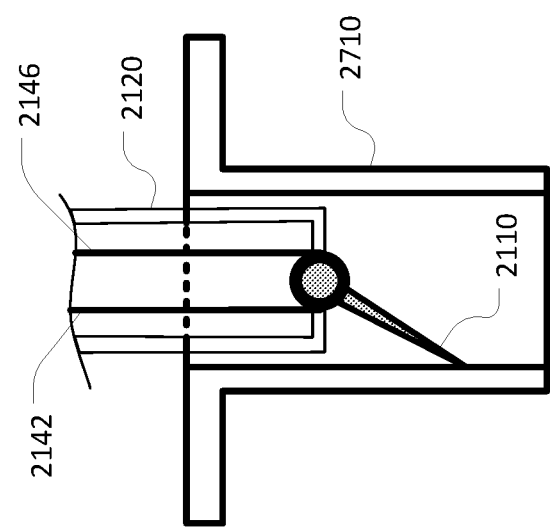

According to some embodiments, method 2600 is described with respect to the representative embodiments of FIGS. 27A-27C, which depict an end effector during a homing method. As shown in FIGS. 27A-27C, the detectable positions of method 2600 correspond to collisions between the end effector 2110 and a cannula 2710 through which shaft 2120 and end effector 2110 are inserted. In some examples, cannula 2710 is consistent with cannula 256. In some examples, the locations of cannula 2710 relative to end effector 2110 are known so that when end effector 2110 collides with cannula 2710 the position of the degree of freedom of end effector 2110 becomes known. However, one skilled in the art would recognize that other types of detectable positions are possible other than those corresponding to collision between a cannula and an end effector. In some examples, the detectable positions may correspond to collisions between the end effector and other structures, range of motion limits of the degree of freedom of the end effector, position feedback associated with the degree of freedom of the end effector, and/or the like. In some examples, the position feedback may correspond to sensors readings used to detect the position of the degree of freedom from one or more sensors located in the end effector (e.g., a potentiometer, an encoder, and/or the like detecting a rotation angle of the degree of freedom) and/or external to the end effector. (e.g., an external imaging or detecting device, such as a fluoroscope, a computer-aided tomography device, and/or the like).

In reference to FIG. 26, at a process 2610, the degree of freedom is actuated in a first direction. In some examples, the degree of freedom is actuated in the first direction by applying differential actuation using the two actuators (e.g., actuators 2152 and 2162) as, for example, described with respect to FIGS. 10-13. In some examples, the differential actuation may be similar to the actuation of process 2520 except that different position, velocity, force, torque, and/or current set points are used with the two actuators in order to cause the differential actuation. As a result of the differential actuation, the degree of freedom begins to move in the first direction.

At a process 2620, it is determined whether a first detectable position is reached. As shown in the embodiments of FIG. 27A, the first detectable position corresponds to end effector 2110 colliding with a first side of cannula 2710. In some examples, the collision between end effector 2210 and the first side of cannula 2710 may be detected using a process similar to the engagement detections of processes 2530 and/or 2550. In some examples, when end effector 2110 collides with the first side of cannula 2710 a force and/or torque associated with a first one of the actuators used to control the degree of freedom increases as the actuator is prevented from moving the degree of freedom further in the first direction. In some examples, the collision between end effector 2210 and the first side of cannula 2710 may be detected based on any combination of one or more of a force, a torque, a current, a position, a speed, a position error, and/or the like associated with the actuator that is primarily responsible for actuating the degree of freedom in the first direction. Once the first detectable position is reached, the positions of both actuators used to control the first degree of freedom are recorded. In some examples, the positions may correspond to values from corresponding position sensors such as shaft encoders, turn counters, and/or the like. When the first detectable position is not reached, further actuation of the degree of freedom continues in the first direction by returning to process 2610. When the first detectable position is reached, the degree of freedom is actuated in a second direction using a process 2630.

At the process 2630, the degree of freedom is actuated in a second direction. In some examples, the second direction is opposite the first direction. In some examples, the degree of freedom is actuated in the second direction by applying differential actuation opposite to the differential actuation used during process 2610. As a result of the differential actuation, the degree of freedom begins to move in the second direction.

At a process 2640, it is determined whether a second detectable position is reached. As shown in the embodiments of FIG. 27B, the second detectable position corresponds to end effector 2110 colliding with a second side of cannula 2710. In some examples, the collision between end effector 2210 and the second side of cannula 2710 may be detected using a process similar to process 2620, but based on a force, a torque, a current, a position, a speed, a position error, and/or the like associated with the actuator that is primarily responsible for actuating the degree of freedom in the second direction. Once the second detectable position is reached, the positions of both actuators used to control the first degree of freedom are recorded in similar fashion to the recorded positions from process 2620. When the second detectable position is not reached, further actuation of the degree of freedom continues in the second direction by returning to process 2630. When the second detectable position is reached, the degree of freedom is actuated to a home position using a process 2650.

At the process 2650, the degree of freedom is actuated to the home position. In some examples, the home position is reached by actuating the degree of freedom in the first direction. The home position is determined based on a combination of the actuator positions recorded during processes 2620 and 2640. In some examples, the home position for each of the actuators is determined based on a weighted sum (e.g., an average) of the recorded positions for that actuator recorded during processes 2620 and 2640. Once the home position for each of the actuators is determined, the actuators are actuated to their respective home positions. In some examples, position control using a position set point based on the respective home position is used to actuate the degree of freedom to the home position. In some examples, the home position corresponds to a center position for the degree of freedom as shown in FIG. 27C.

Referring back to FIG. 25, at a process 2580, the degree of freedom is controlled using the one or more actuators. In some examples, the one or more actuators are cooperatively actuated to control the degree of freedom. In some examples, processes similar to processes 2610, 2630, and/or 2650 may be used to control the degree of freedom. In some examples, the one more actuators may control the degree of freedom using one or more of position control, velocity control, force control, torque control, and/or the like. In some examples, each of the one or more actuators may be further constrained by a configurable force, torque, and/or current limit to prevent driving its respective engagement member with excessive force and/or torque.

Figure 28:
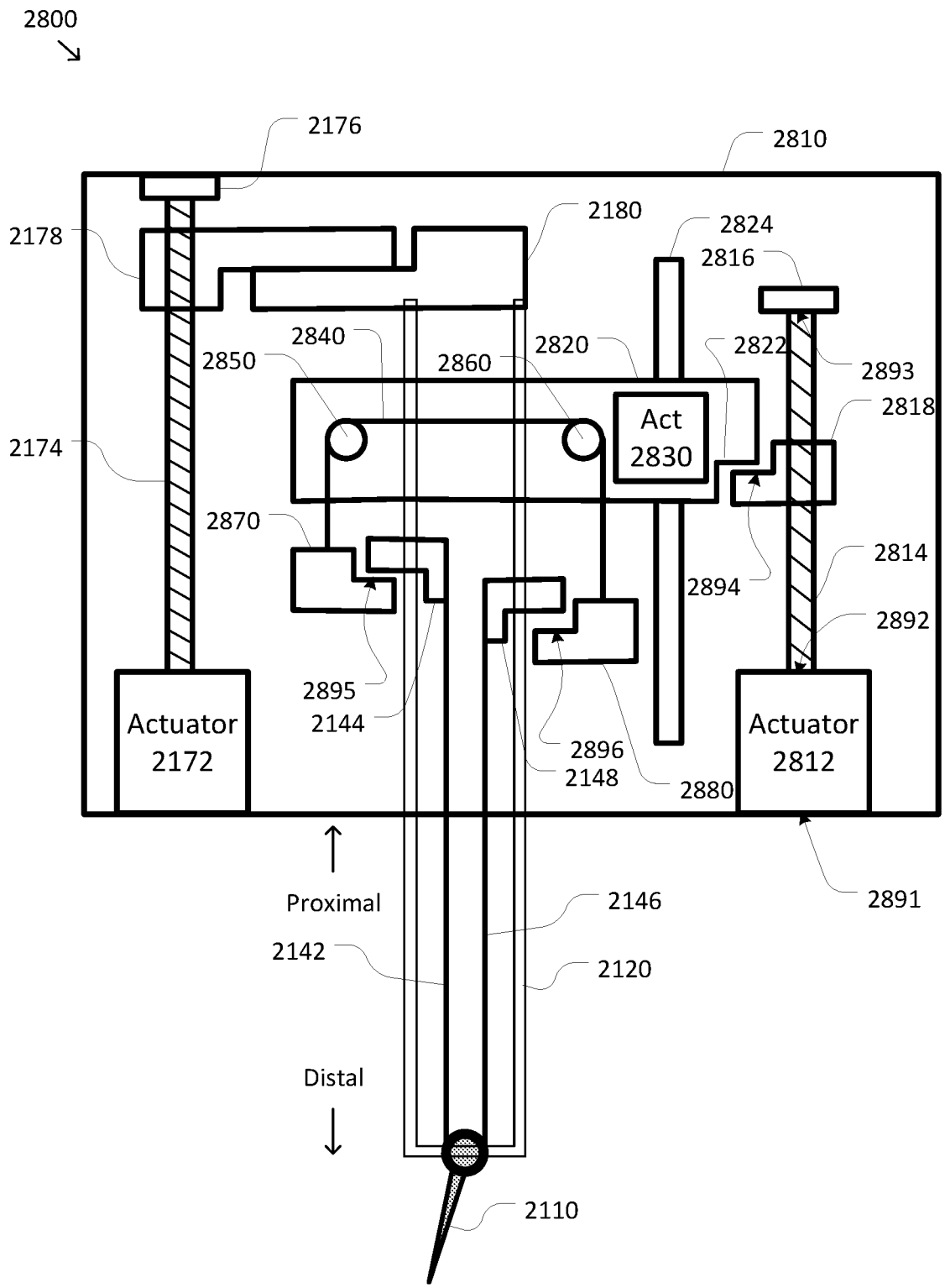
FIG. 28 depicts another drive unit and instrument in accordance with some embodiments.

Referring to FIG. 28, another system 2800 with an instrument having a controllable end effector 2110 is shown prior to engagement in accordance with some embodiments. System 2800 includes several features that are similar to corresponding features in system 2100 and thus features with the same reference numbers in FIG. 28 have similar corresponding structures and purposes as the features with the same reference numbers in FIGS. 21-23. As shown in FIG. 28, end effector 2110 is coupled via a shaft 2120 to a drive unit 2810. In some embodiments, end effector 2110 may be end effector 2070, shaft 2120 may be shaft 2060, and/or drive unit 2810 may be instrument drive system 700 and/or drive unit 2050. The instrument further includes a transmission mechanism 2142 coupling end effector 2110 to an engagement member 2144 located proximal to end effector 2110. As shown, movement of engagement member 2144 in a proximal direction by drive unit 2810 results in movement of a degree of freedom of end effector 2110 in a first direction. Similarly, the instrument further includes a transmission mechanism 2146 coupling end effector 2110 to an engagement member 2148 located proximal to end effector 2110. As shown, movement of engagement member 2148 in a proximal direction by drive unit 2810 results in movement of the degree of freedom of end effector 2110 in a second direction opposite the first direction in an antagonistic fashion. In some examples, transmission mechanisms 2142 and/or 2146 may perform a function similar to tensioning members 340 and/or 360. In some examples, transmission mechanisms 2142 and/or 2146 may each be a mechanism for transferring force or torque from drive unit 2810 to the degree of freedom of end effector 2110 and each may include a cable, a wire, a belt, a band, a chain, a shaft, and/or the like. In some examples, each of engagement members 2144 and/or 2148 may perform a similar function as engagement member 350, 370, 632a, 632b, 634a, 634b, 636a, 636b, and/or 638.

Drive unit 2810 includes an actuator 2172 mounted to drive unit 2810. In some examples, actuator 2172 is a motor and/or the like. Actuator 2172 is drivably coupled to a lead screw 2174 at a first end of lead screw 2174. A second end of lead screw 2174 is anchored to the housing of drive unit 2810 via a mounting member 2176 that allows rotation of lead screw 2174 by actuator 2172. As lead screw 2174 is rotated by actuator 2172, the rotation causes an engagement member 2178 to move along lead screw 2174. In some examples, engagement member 2178 is a threaded nut, such as treaded nuts 740a-h as described in further detail in International Patent Application No. PCT/US2017/51846. If engagement member 2178 is moved far enough along lead screw 2174, engagement member 2178 makes contact with an engagement member 2180 located at the end of shaft 2120 opposite end effector 2110 and can be used to help control insertion and/or retraction of shaft 2120 and end effector 2110 relative to drive unit 2810.

Drive unit 2810 further includes an actuator 2812 mounted to drive unit 2810. In some examples, actuator 2812 is a motor and/or the like. Actuator 2812 is drivably coupled to a lead screw 2814 at a first end of lead screw 2814. A second end of lead screw 2814 is anchored to the housing of drive unit 2810 via a mounting member 2816 that allows rotation of lead screw 2814 by actuator 2812. As lead screw 2814 is rotated by actuator 2812, the rotation causes an engagement member 2818 to move along lead screw 2814. In some examples, engagement member 2818 is a threaded nut, such as treaded nuts 740a-h as described in further detail in International Patent Application No. PCT/US2017/51846. If engagement member 2818 is moved far enough along lead screw 2814, engagement member 2818 makes contact with an engagement member 2822 located on a moveable platform 2820. Moveable platform 2820 is mounted on one or more guide rails 2824, guide bars, and/or the like mounted to drive unit 2810. The one or more guide rails 2828 are arranged parallel to shaft 2120 and constrain platform 2820 so that platform 2820 moves along an axis parallel to shaft 2120. Platform 2820 includes an actuator 2830 mounted thereon. In some examples, actuator 2830 is a motor and/or the like. Actuator 2830 is drivably coupled to a transmission mechanism 2840 that passes around two capstans or pulleys 2850 and 2860. In some examples, each of the capstans 2850 and 2860 are fixedly mounted to platform 2820 or are mounted so as to rotate freely relative to platform 2820 about an axle (not shown). In some examples, transmission mechanism 2840 may be passed over each of the capstans 2850 and 2860 and/or may be wrapped one or more times around capstans 2850 and 2860. In some examples, actuator 2830 may drive transmission mechanism 2840 in either direction by pulling and/or pushing transmission mechanism 2840 and/or by drivably rotating capstan 2850 and/or capstan 2860. A first end of transmission mechanism 2840 is attached to an engagement member 2870 and a second end of transmission mechanism 2840 opposite the first end is attached to an engagement member 2880. In some examples, transmission mechanism 2840 may perform a function similar to tensioning members 340 and/or 360 and/or transmission mechanisms 2142 and/or 2146 with respect to engagement members 2870 and 2880. In some examples, transmission mechanism 2840 may be a mechanism for transferring force or torque from drive unit 2810 to one or both of engagement members 2870 or 2880. In some examples, transmission mechanism 2840 may include a cable, a wire, a belt, a band, a chain, a shaft, and/or the like.

According to some embodiments, drive unit 2810 operates by actuating actuator 2812 as a common mode actuator to engage engagement member 2818 with engagement member 2822. Continued actuation of actuator 2812 causes platform 2820 to be pushed proximally until a first one of engagement members 2870 or 2880 engages with engagement member 2144 or 2148, respectively. Further actuation of actuators 2172 and/or 2812 further pushes platform 2820 proximally until engagement member 2870 engages with engagement member 2144 and engagement member 2880 engages with engagement member 2148. This actuation may continue until a desired pre-tension is obtained in transmission mechanism 2840. In some examples, when actuator 2830 is allowed to be back driven by transmission mechanism 2840, transmission mechanism 2840 moves during this continued actuation and engagement between engagement member 2870 and engagement member 2144 and engagement between engagement member 2880 and engagement member 2148 occurs with little or no motion in the degree of freedom of end effector 2110. Once pre-tensioning is complete, actuator 2830 may be used as a differential mode actuator to mutually move engagement members 2870 and 2880 in opposite directions, which results in corresponding movement in engagement members 2144 and 2148, respectively, and corresponding motion in the degree of freedom of end effector 2110.

Drive unit 2810 may additionally include one or more sensors that may be used to monitor actuators 2172, 2812, and/or 2830, the locations of engagement members 2178, 2818, 2870, and/or 2880, engagement between engagement members 2178, 2818, 2870, and/or 2880 with engagement members 2180, 2822, 2144, and/or 2148, respectively, and/or the like. In some examples, signals from one or more force and/or torque sensors may be used to estimate an amount of force and/or torque being applied by a respective engagement member 2178, 2818, 2870, and/or 2880 to a corresponding engagement member 2180, 2822, 2144, and/or 2148. Possible locations for the one or more force and/or torque sensors include any portion where the force and/or torque is transmitted, and some possible locations are indicated by arrows 2891-2894 for engagement member 2818, with engagement member 2178 having similar possible locations. As shown, location 2891 is between an end of actuator 2812 opposite lead screw 2814 and the housing of drive unit 2810. Location 2892 is where lead screw 2814 is coupled to actuator 2812. Location 2893 is located where lead screw 2814 is coupled to mounting member 2816 or alternatively between mounting member 2816 and the housing of drive unit 2810. Location 2894 is on a surface of engagement member 2818 where engagement member 2818 makes contact with engagement member 2822. Additional possible locations are shown for actuator 2830 as indicated by arrows 2895 and 2896. As shown, location 2895 is on a surface of engagement member 2870 where engagement member 2870 makes contact with engagement member 2144 and location 2896 is on a surface of engagement member 2880 where engagement member 2880 makes contact with engagement member 2148. Additional possible locations associated with actuator 2172 include where actuator 2172 is mounted to the housing of drive unit 2810, where lead screw 2174 is coupled to actuator 2172, between mounting member 2176 and the housing of drive unit 2810, where engagement member 2178 makes contact with engagement member 2180, and/or the like. Additional possible locations associated with actuator 2830 include where actuator 2830 is mounted, where transmission mechanism 2840 is coupled to actuator 2830, with either of capstans 2850 and/or 2860, and/or the like.

In some examples, other locations are possible. In some examples, multiple force and/or torque sensors may be used at any combination of locations. In some examples, the forces or torques measured by each of the force and/or torque sensors may be aggregated to estimate the force or torque applied by the respective engagement member (the engagement member being moved by an actuator of the drive unit) to a corresponding engagement member. In some examples, the aggregation may be a weighted sum, such as an average. In some examples, each of the one or more force and/or torque sensors may include a strain gauge, a pressure transducer, a force transducer, a piezoelectric device, and/or the like.

In some embodiments, other type of sensors may be used to monitor actuators 2172, 2812, and/or 2830, the locations of engagement members 2178, 2818, 2870, and/or 2880, and/or the like. In some examples, one or more position and/or speed/velocity sensors located at, for example, location 2892 may be used to track a position and/or velocity of lead screw 2814 and/or engagement member 2818 along lead screw 2814. In some examples, one or more proximity and/or contact sensors located at, for example, location 2894 may be used to detect proximity and/or contact between engagement member 2818 and engagement member 2822. In some examples, transmission mechanism 2840 and/or one or both of capstans 2850 and/or 2860 may be monitored by one or more position and/or speed/velocity sensors to track a position and/or velocity of transmission mechanism 2840. In some examples, platform 2820 and/or one or more of the guide rails 2824 may be monitored by one or more position and/or speed/velocity sensors to track a position and/or velocity of platform 2820. In some examples, one or more proximity and/or contact sensors located at, for example, location 2895 may be used to detect proximity and/or contact between engagement member 2870 and engagement member 2144. In some examples, one or more proximity and/or contact sensors located at, for example, location 2896 may be used to detect proximity and/or contact between engagement member 2880 and engagement member 2148. In some examples, the one or more proximity and/or contact sensors may include mechanical, resistive, or capacitive switches, pressure transducers, strain gauges, Hall Effect sensors, RFID devices, and/or the like.

FIG. 28 shows a configuration of system 2800 before drive unit 2810 is engaged with end effector 2110. More specifically, FIG. 28 shows engagement members 2870 and 2880 separated from engagement members 2144 and 2148, respectively, and before engagement member 2818 is engaged with engagement member 2822, such as might occur when the instrument is mounted to drive unit 2810. As drive unit 2810 operates to engage with the instrument and then to control the degree of freedom of the instrument, additional configurations of system 2800 are possible, which have similarities to the configurations of FIGS. 22 and 23 for system 2100. More specifically, in some embodiments, drive unit 2810 operates by actuating actuator 2812 as a common mode actuator to engage engagement member 2818 with engagement member 2822. Continued actuation of actuator 2812 causes platform 2820 to be pushed proximally until a first one of engagement members 2870 or 2880 engages with engagement member 2144 or 2148, respectively. Further actuation of actuators 2172 and/or 2812 further pushes platform 2820 proximally until engagement member 2870 engages with engagement member 2144 and engagement member 2880 engages with engagement member 2148. This actuation may continue until a desired pre-tension is obtained in transmission mechanism 2840. In some examples, when actuator 2830 is allowed to be back driven by transmission mechanism 2840, transmission mechanism 2840 moves during this continued actuation and engagement between engagement member 2870 and engagement member 2144 and engagement between engagement member 2880 and engagement member 2148 occurs with little or no motion in the degree of freedom of end effector 2110. Once pre-tensioning is complete, actuator 2830 may be used as a differential mode actuator to mutually move engagement members 2870 and 2880 in opposite directions, which results in corresponding movement in engagement members 2144 and 2148, respectively, and corresponding motion in the degree of freedom of end effector 2110.

As discussed above and further emphasized here, FIG. 28 is merely an example which should not unduly limit the scope of the claims. One of ordinary skill in the art would recognize many variations, alternatives, and modifications. According to some embodiments, system 2800 may include different arrangements and/or include additional elements. In some example, one or more sterile barriers (e.g., a drape and/or the like) may be placed between any two of the engagement members that are configured to engage with each other. In some examples, actuator 2830 may be mounted to the housing of drive unit 2810 and not to platform 2820 with force and/or torque being transmitted from actuator 2830 to transmission mechanism 2840 using a spline and/or the like. In some examples, one or more portions of capstans 2850 and 2860 and/or transmission mechanism 2840 may be replaced with a gear train. In some examples, the gear train may include one or more idler gears and/or racks to achieve equivalent motion between the two ends of transmission mechanism 2840.

According to some embodiments, platform 2820 may be coupled directly to lead screw 2814 and engagement members 2818 and 2822 omitted. In this case, rotation of lead screw 2814 causes movement of platform 2820 directly so that actuation of actuator 2812 results in motion of platform 2820 without engagement between engagement member 2818 and engagement member 2822 having to take place first.

According to some embodiments, the engagement between engagement member 2178 and engagement member 2180 may include other and/or different components than those shown in FIG. 28. In some examples, engagement member 2178 and/or engagement member 2180 may each include a hook, tab, clip, latch, and/or the like so that engagement member 2178 and engagement member 2180 are coupled in a detained fashion (see, e.g., engagement member 620 of FIG. 16) when the instrument is attached to drive unit 2810.

According to some embodiments, drive unit 2810 and the instrument may include additional components that are not shown. In some examples, engagement members 2144 and/or 2148 may have a limited range of motion. In some examples, the motion may be limited by slots similar to the longitudinal slots of FIG. 16. In some examples, engagement members 2144 and/or 2148 may each be associated with one or more pre-tensioning and/or pre-positioning elements, such as springs 633 of FIG. 16 to control a position of respective engagement members 2144 and/or 2148 and/or slack in respective transmission mechanisms 2142 and/or 2146. In some embodiments, platform 2820 and/or the one or more guide rails 2824 include one or more mechanisms, such as one or more springs that push platform 2820 distally relative to drive unit 2810 when engagement member 2822 is not engaged with engagement member 2818.

Although not shown in FIG. 28, actuators 2172, 2812, and/or 2830 are each coupled to one or more corresponding control signals that are used to control rotation of the respective actuator. In some examples, the one or more control signals may be provided by a control unit (e.g., control unit 2010) and/or a motion control module (e.g., motion control module 2014). In some examples, the one or more control signals may correspond to one or more voltages, one or more currents, one or more pulse-width modulated signals, and/or the like.

Although FIG. 28 depicts control of end effector 2110 using, in part, rotational actuators (e.g., motors) and lead screws, other mechanisms may be used. In some examples, one or more of lead screws 2174 and/or 2814 may be replaced with other types of rotational to linear motion converters. In some examples, one or more of actuators 2172 and 2812 may be replaced by servos, hydraulic, electromagnetic, and/or pneumatic solenoids, pistons, and/or the like. In some examples, one or more of lead screws 2174 and/or 2814 may be replaced by cables, belts, bands, chains, shafts, and/or the like.

Although FIG. 28 depicts the relative orientation of actuators 2172, 2812, and 2830 and their corresponding lead screws, platform 2820, etc. as being coplanar, this orientation is not the only possible relative orientation. In some examples, each of actuators 2172, 2812, and/or 2830 and/or platform 2820 may be located at different angular positions around shaft 2120, such as is shown in International Patent Application No. PCT/US2017/51846.

Figure 29:
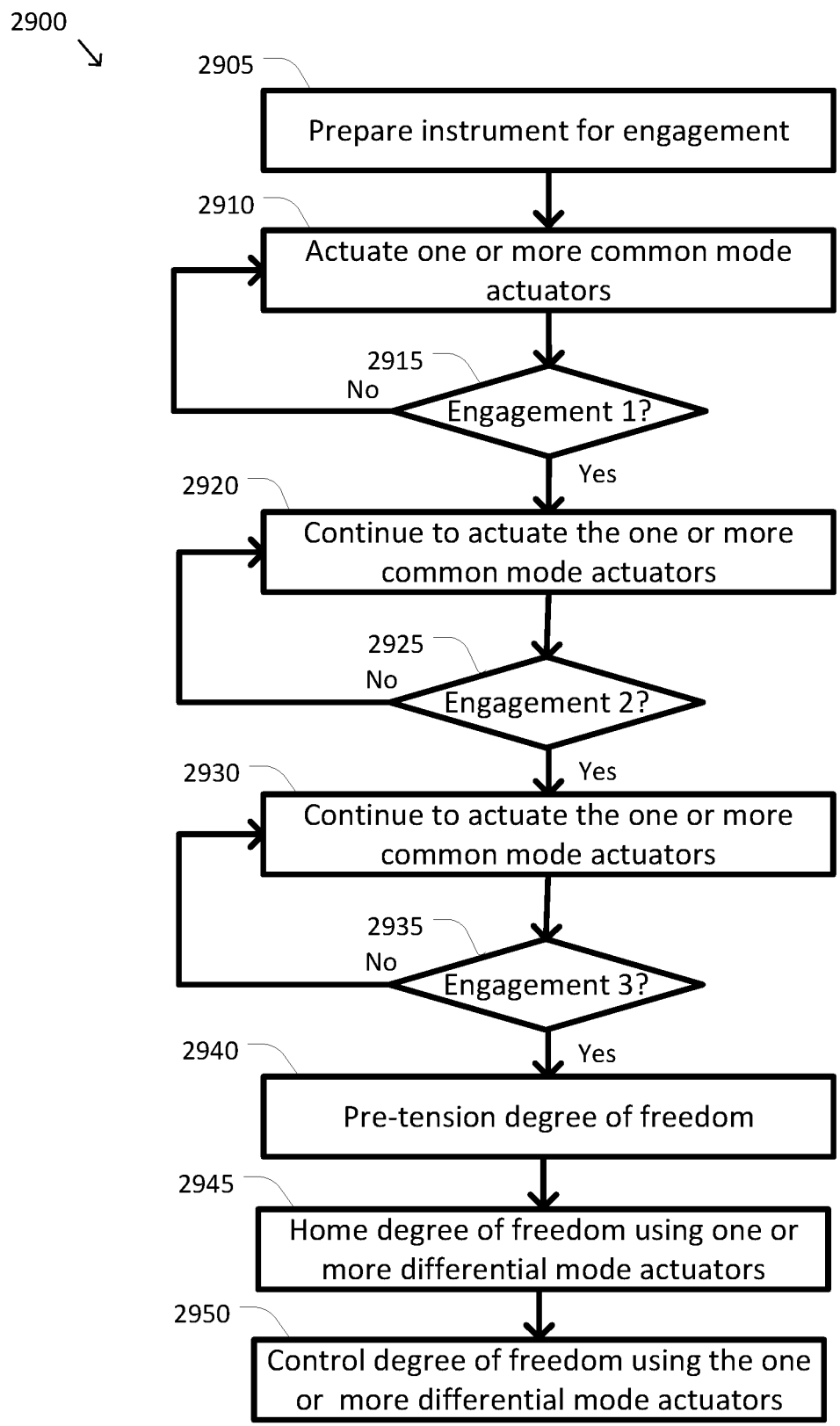
FIG. 29 depicts another method of engagement in accordance with some embodiments.

Referring to FIG. 29, a method 2900 of engagement in accordance with some embodiments is shown. One or more of the processes 2905-2950 of method 2900 may be implemented, at least in part, in the form of executable code stored on non-transitory, tangible, machine-readable media that when run by one or more processors (e.g., processor 2020 in control unit 2010) may cause the one or more processors to perform one or more of the processes 2905-2950. In some embodiments, method 2900 may be performed by a module, such as motion control module 2040. In some examples, method 2900 may be used to control actuators 2172, 2812, and/or 2830 of drive unit 2810 as shown in FIG. 28, which are used to control the degree of freedom of end effector 2110. In some embodiments, process 2945 is optional and may be omitted.

At a process 2905, an instrument is prepared for engagement. In some examples, before engagement can occur the instrument is attached to a drive unit, such as drive unit 2810. In some examples, process 2905 is substantially similar to process 2810. In some examples, at the end of process 2910, drive unit 2810, actuators 2172, 2812, and 2830, and engagement members 2178, 2180, 2818, 2822, 2870, 2880, 2144, and 2148 may be in the configuration as shown in FIG. 28.

At a process 2910, one or more common mode actuators used to control a degree of freedom of an end effector are actuated. In some examples, the one or more common mode actuators include actuator 2812. The one or more common mode actuators are actuated so as to move and/or drive a first engagement member, such as engagement member 2818, toward a second engagement member of a platform, such as platform 2820. In some examples, this actuation may include position control where each of the one or more common mode actuators begins moving its engagement member to a far end of its lead screw and/or a velocity control where each of the one or more common mode actuators begins moving its engagement member at a configurable velocity away from the respective common mode actuator. In some examples, each of the one or more common mode actuators may be further constrained by a configurable force, torque, and/or current limit to prevent driving its respective engagement member with excessive force and/or torque. In some examples, the force, torque, and/or current limit may correspond to a corresponding pre-tension value. In some examples, process 2910 corresponds to the period before a first temporary increase in force or torque or a first temporary decrease in speed is detected, such as occurs in curve 2420 at time/period $x_1$ in FIG. 24.

At a process 2915, it is determined whether the one or more common mode actuators has moved the first engagement member so that it is engaged with the second engagement member (e.g., when engagement member 2818 engages with engagement member 2822). In some examples, the engagement between the first engagement member and the second engagement member may be detected based on any combination of one or more of a force, a torque, a current, a position, a speed, a position error, and/or the like associated with the first engagement member, a contact and/or proximity sensor associated with the first engagement member, and/or the like. In some examples, the engagement between the first engagement member and the second engagement member may be detected using an approach similar to that described with respect to detecting the changes in curve 2420 at time/position $x_1$, when monitoring the one or more common mode actuators, such as by detecting a temporary increase in force or torque, detecting an increase in force or torque followed by a smaller decrease, detecting a temporary reduction in speed, detecting a decrease in speed followed by a smaller increase, and/or the like. When engagement between the first engagement member and the second engagement member is not yet detected, the one or more common mode actuators continue to be actuated by returning to process 2910. When engagement between the first engagement member and the second engagement member is detected, further actuation occurs beginning with a process 2920.

At the process 2920, actuation of the one or more of the common mode actuators continues. In some examples, the actuation of process 2910 continues with the one or more common mode actuators being actuated so as to cause further movement and/or driving of the first engagement member and thus the platform via the engagement between the first engagement member and the second engagement member. In some examples, process 2920 may correspond to a period between time/period $x_1$ of FIG. 24 and a time/period where a second temporary increase in force or torque or a second temporary decrease in speed occurs (not shown in FIG. 24).

At a process 2925, it is determined whether the one or more common mode actuators has moved the first engagement member so that it has pushed the second engagement member and thus the platform so that a third engagement member associated with the platform engages with a fourth engagement member (e.g., when platform 2820 has moved such that engagement member 2870 engages with engagement member 2114 or engagement member 2818 engages with engagement member 2822). In some examples, the engagement between the third engagement member and the fourth engagement member may be detected based on any combination of one or more of a force, a torque, a current, a position, a speed, a position error, and/or the like associated with the first and/or third engagement members, a contact and/or proximity sensor associated with the third engagement member, and/or the like. In some examples, the engagement between the third engagement member and the fourth engagement member may be detected using an approach similar to that described with respect to detecting the changes in curve 2420 at time/position $x_1$, when monitoring the one or more common mode actuators, such as by detecting a temporary increase in force or torque, detecting an increase in force or torque followed by a smaller decrease, detecting a temporary reduction in speed, detecting a decrease in speed followed by a smaller increase, and/or the like. When engagement between the third engagement member and the fourth engagement member is not yet detected, the one or more common mode actuators continue to be actuated by returning to process 2920. When engagement between the third engagement member and the fourth engagement member is detected, further actuation occurs beginning with a process 2930.

At the process 2930, actuation of the one or more of the common mode actuators continues. In some examples, the actuation of process 2910 and 2920 continues with the one or more common mode actuators being actuated so as to cause further movement and/or driving of the first engagement member. In some examples, process 2930 may correspond to a period after the second time/period where the second temporary increase in force or torque or a second temporary decrease in speed occurred.

At a process 2935, it is determined whether the one or more common mode actuators have moved the first engagement member so that it has pushed the second engagement member and thus the platform so that the third engagement member associated with the platform engages with the fourth engagement member and a fifth engagement member associated with the platform engages with a sixth engagement member (e.g., when platform 2820 has moved such that engagement member 2870 engages with engagement member 2114 and engagement member 2818 engages with engagement member 2822). In some examples, the engagement between the third engagement member and the fourth engagement member and the engagement between the fifth engagement member and the sixth engagement member may be detected based on any combination of one or more of a force, a torque, a current, a position, a speed, a position error, and/or the like associated with both the first, third, and/or fifth engagement members, contact and/or proximity sensors associated with the fifth engagement member, and/or the like. In some examples, the engagement between both the third engagement member and the fourth engagement member and engagement between the fifth engagement member and the sixth engagement member may be detected as described with respect to detecting the changes in curves 2420 and 2440 at time/position $x_2$ when monitoring the one or more common mode actuators. When engagement between the third engagement member and the fourth engagement member and engagement between the fifth engagement member and the sixth engagement member is not yet detected, the one or more common mode actuators continue to be actuated by returning to process 2930. When engagement between the third engagement member and the fourth engagement member and engagement between the fifth engagement member and the sixth engagement member is detected, further control occurs beginning with a process 2940.

At the process 2940, pre-tensioning of the degree of freedom is performed. In some examples, the force and/or torque associated with the one or more common mode actuators is increased until each reaches a configurable pre-tension value. In some examples, the pre-tensioning increases the likelihood that any slack and/or give in the transmission mechanisms used to control the degree of freedom are taken up. In some examples, the pre-tensioning provides actuation forces to counteract actuation forces used to control an insertion and/or retraction of the instrument (e.g., the actuation provided by actuator 2172). In some examples, the pre-tension may be performed by setting the force, torque, and current limit of the one or more common mode actuators to the configurable pre-tension value and continuing actuation similar to the actuation of processes 2910, 2920, and/or 2930 until further movement of the one or more common mode actuators is constrained by the corresponding force, torque, and/or current limit.

At an optional process 2945, the degree of freedom is homed using one or more differential mode actuators. In some examples, because of variations between end effectors, wear and tear on the end effectors, and/or the like, when the pre-tensioning of process 2940 is complete the actual location of the degree of freedom is not known. In some examples, the one or differential mode actuators include actuator 2830. The homing of process 2945 allows the location of the degree of freedom to be known with greater certainty. In some examples, the degree of freedom may be homed according to method 2600 as shown in FIG. 26 but by using the one or more differential mode actuators rather than the antagonistic control of actuators 2152 and 2162. In some examples, each of the common mode actuators are prevented from moving during process 2945, such as by servoing each of the one or more common mode actuators to a current respective position.

At a process 2950, the degree of freedom is controlled using the one or more differential actuators. In some examples, when each the one or more differential mode actuators is actuated in a first actuation direction, the degree of freedom of the end effector is moved in the first direction and when each of the one or more differential mode actuators is actuated in a second actuation direction opposite the first actuation direction, the degree of freedom of the end effector is moved in the second direction. In some examples, this differential actuation may include position control where each of the one or more differential mode actuators begins moving toward a configurable position set point and/or a velocity control where each of the differential mode actuators begins moving at a configurable velocity set point. In some examples, each of the differential mode actuators may be further constrained by a configurable force, torque, and/or current limit to prevent driving with excessive force and/or torque. In some examples, each of the common mode actuators are prevented from moving during process 2950, such as by servoing each of the one or more common mode actuators to a current respective position.

As discussed above and further emphasized here, FIGS. 25, 26, and/or 29 are merely examples which should not unduly limit the scope of the claims. One of ordinary skill in the art would recognize many variations, alternatives, and modifications. In some embodiments, the actuators may be actuated in different patterns and combinations during method 2500. In some examples, only the first actuator may be actuated during process 2520 with the second actuator being maintained in place.

In some embodiments, the actuators may be actuated in different patterns and combinations during method 2900. In some examples, during one or more of processes 2905-2940, each of the one or more differential mode actuators may be placed in a floating mode so that during the engagement of processes 2905-2940 the degree of freedom of the end effector does not move much as the engagement between the third engagement member and the fourth engagement member and engagement between the fifth engagement member and the sixth engagement member occurs. In some examples, each of the one or more differential mode actuators may be back driven so as to adjust the positions of the third and fifth engagement members without moving the fourth and sixth engagement members. In some examples, each of the one or more differential mode actuators may be servoed to a current position set point during one or more of the processes 2905-2940 so that the positions of the third and fifth engagement members do not change during the engagement process. In some examples, this servoing may result in movement in the degree of freedom of the end effector.

Although not shown in FIGS. 25, 26, and 29, various conditions may result in termination and/or retry of methods 2500, 2600, and/or 2900 before engagement and/or homing may be completed. In some examples, methods 2500 and/or 2900 may be terminated or retried when the engagement of any one of processes 2530, 2550, 2915, 2925, and/or 2935 does not occur (e.g., the expected, force, torque, speed, position error, contact, and/or like is not detected) within a configurable time interval (e.g., as tracked by a timer started when method 2500 and/or 2900 begins). Similarly, method 2600 may be terminated or retried when either the first position and/or the second position are not reached (e.g., as detected by processes 2620 and/or 2640) within a configurable time interval. In some examples, methods 2500 and/or 2900 may be terminated or retried when the pre-tensioning of processes 2560 and/or 2940 is not reached within a configurable time limit, a force, torque, speed, position error or contact pattern is not an expected pattern, and/or the like. In some examples, any of methods 2500, 2600, and/or 2900 may be terminated or retried if any of the actuators reaches a configurable travel limit (e.g., actuation members 2158, 2168, and/or 2818 reach a far end of lead screws 2154, 2164, and/or 2814, respectively) and/or transmission mechanism 2840 reaches a travel limit, and/or the like before engagement is detected and/or the detectable positions are reached. In some examples, any of methods 2500, 2600, and/or 2900 may be terminated or retried by operator command, change in mode of the instrument, detection that the instrument is un-mounted from the drive unit, a system fault, and/or the like.

In some embodiments, when the first engagement member and the second engagement member are omitted and the one or more common mode actuators drive the platform directly, processes 2910 and 2915 may be omitted. In this case, processes 2920, 2930, and 2940 operate such that actuation of the one or more common mode actuators causes movement of the platform directly without the movement of the platform involving the first engagement member.

In some embodiments, either of methods 2500 and/or 2900 may further include a process for confirming engagement between the various engagement members either before or after the pre-tensioning of processes 2560 and/or 2840. In some examples, engagement may be confirmed by actuating the degree of freedom in either or both the first direction or second direction and using a detected position of degree of freedom to confirm that corresponding movement in the degree of freedom is taking place. In some examples, engagement may be confirmed by actuating the first and second actuators and/or the one or more differential mode actuators, such as during the pre-tensioning of processes 2560 and/or 2840, respectively, and confirming a corresponding increase in the force and/or torque (or speed decrease, position error increase, and/or the like) associated with the first and second actuators and/or the one or more differential mode actuators. In some examples, engagement may be confirmed by actuating the first and second actuators and/or the one or more common mode actuators away from engagement and confirming a corresponding decrease in the force and/or torque (or position error decrease, loss of contact or proximity, and/or the like) occurs.

In some embodiments, either of method 2500 and/or 2900 may be adapted to handle the case where process 2510 does not engage the pair of engagement members that are used to move a shaft of the instrument in the insertion direction. In some examples, during method 2500, when the first engagement member makes contact with the third engagement member (e.g., at time/position $x_1$) further movement of the first engagement member also moves the engagement member at the proximal end of the instrument shaft (e.g., engagement member 2180) toward the corresponding engagement member of the drive unit (e.g., engagement member 2178). In some examples, this may increase a magnitude of changes in curve 2420 at time/position $x_1$, but the overall temporal, positional or other spatial, or frequency pattern remains similar. In some examples, the slope of curve 2420 may also increase between time/position $x_1$ and time/position $x_2$. Depending upon the relative locations of the other engagement members, either the engagement member at the proximal end of the instrument shaft will engage with the corresponding engagement member of the drive unit or the second engagement member will engage with the fourth engagement member will occur next. When the engagement member at the proximal end of the instrument shaft engages with the corresponding engagement member of the drive unit first, then the upward slope of curve 2420 may decrease slightly as the first engagement member no longer has to move the instrument shaft proximally, but no corresponding change in curve 2440 will occur until the second engagement member engages with the fourth engagement member. When the second engagement member engages with the fourth engagement member first, then an increase will occur in curve 2440, but a decrease will occur in curve 2420 because both the first and second engagement members are cooperatively moving the instrument shaft proximally. However, when the engagement member at the proximal end of the instrument shaft engages with the corresponding engagement member of the drive unit both curves 2420 and 2440 will show the characteristic increase at time/position $x_2$ as the first and second engagement members act in antagonism with each other. In some examples, the pre-tensioning of process 2560 will further increase the engagement between the engagement member at the proximal end of the instrument shaft will engage and the corresponding engagement member of the drive unit. In some examples, when the engagement member at the proximal end of the instrument shaft engages with the corresponding engagement member of the drive unit this may also cause the engagement member at the proximal end of the instrument shaft and the corresponding engagement member of the drive unit to be coupled in a detained fashion when so configured. In some examples, the magnitude change at time/position $x_1$ and the slope between time/position $x_1$ and time/position $x_2$ may be different if the user is supporting the instrument as the instrument engages. In some examples, the magnitude at time/position $x_1$ may depend on the speed at which the first contact between first and third engagement members are made. In some examples, the slope at any instant between time/position $x_1$ and time/position $x_2$ may depend on the resistance provided by the user before the next engagement happens (either proximal engagement members for insertion or the second/fourth engagement member pair). In some examples, one or more of a force, a torque, a current, a position, a speed, a position error, and/or the like associated with the engagement member of the drive unit, a contact and/or proximity sensor associated with the engagement member of the drive unit, and/or the like may be used to detect the engagement between the engagement member at the proximal end of the instrument shaft and the corresponding engagement member of the drive unit. In some examples, similar results may occur during method 2900 where the pushing of the fourth and sixth engagement members by the third and fifth engagement members, respectively, may move the second engagement member at the proximal end of the instrument shaft into engagement with the first engagement member.

In some embodiments, either of methods 2500 and/or 2900 may also be used for mutually antagonistic degrees of freedom. In some examples, mutually antagonistic degrees of freedom may exist when two degrees of freedom of a same or different end effector interact with each other in an antagonistic fashion. As an example, a gripper-style end effector may include two jaws that are actuated using separate degrees of freedom. When both jaws are actuated in a same first direction the end effector articulates in the first direction and when both jaws are actuated in a same second direction the end effector articulates in the second direction. However, when the first and second degrees of freedom are actuated in opposite directions, the jaws either open or close depending on which jaw is actuated in the first direction and which jaw is actuated in the second direction. Once the jaws are closed, further actuation of the jaws in the closing direction causes mutual antagonism between the degrees of freedom of the two jaws as movement of one jaw is resisted by the other. In some examples, this mutual antagonism may interfere with the ability of the actuators to perform the actuations of processes 2510, 2530, 2910, 2920, and/or 2930. In some examples, when the first engagement is detected during process 2520 and/or the second engagement is detected during process 2925, even if the corresponding jaw is in contact with the second jaw (e.g., because the second jaw is already engaged or happens to in contact) at most a higher initial increase in the force and/or torque associated with the first engagement member occurs (similarly for speed changes, position errors, and/or the like). In some examples, before the second engagement is detected during process 2540 and/or the third engagement is detected during process 2935, when the first actuator continues to move the first engagement member during process 2540 and the continued movement of the degree of freedom causes the first jaw to push against the second jaw, the force and/or torque associated with the first engagement member may increase before time/position $x_2$ is reached, but engagement of the second engagement member with the fourth engagement member is not accidentally detected, because the force and/or torque associated with the second engagement member does not increase until the second engagement member contacts the fourth engagement member. Similar results occur if speed changes, position error, and/or the like are used to detect the engagement between the second engagement member and the fourth engagement member. In some examples, the use of the force, torque, and/or current limit during processes 2510, 2530, 2910, 2920, and/or 2930 further prevent the engagement of the first jaw from exerting too much force and/or torque against the second jaw.

In some embodiments, method 2600 may also be used for mutually antagonistic degrees of freedom by coordinating the homing of both degrees of freedom. In some examples, both degrees of freedom may be homed concurrently. In some examples, a first degree of freedom may be moved out of the way while a second degree of freedom is homed and then the first degree of freedom may be actuated until it collides with the second degree of freedom.

Some examples of control units, such as control unit 2010 may include non-transitory, tangible, machine readable media that include executable code that when run by one or more processors (e.g., processor 2020) may cause the one or more processors to perform the processes of methods 2500, 2600, and/or 2900. Some common forms of machine readable media that may include the processes of methods 2500, 2600, and/or 2900 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described herein as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   a drive unit comprising a first actuator and a second actuator;
   a first engagement member drivably coupled to the first actuator;
   a second engagement member drivably coupled to the second actuator; and
   a control unit coupled to the drive unit;
   wherein the control unit is configured to, in an engagement mode:
      actuate the first actuator to drive the first engagement member;
      detect engagement of the first engagement member with a third engagement member of an instrument, where a movement of the third engagement member causes a movement of an end effector of the instrument in a first direction of a degree of freedom;
      actuate the second actuator to drive the second engagement member;
      detect engagement of the second engagement member with a fourth engagement member of the instrument, where a movement of the fourth engagement member causes a movement of the end effector in a second direction of the degree of freedom, the second direction being opposite the first direction;
      in response to detecting engagement of the first engagement member with the third engagement member and detecting engagement of the second engagement member with the fourth engagement member, actuate the first and second actuators such that a force or torque experienced by the first engagement member reaches a preset level; and
      actuate the first and second actuators to cause movement of the end effector along the degree of freedom while maintaining the force or torque experienced by the first engagement member at or below the preset level.

2. The computer-assisted device of claim 1, wherein the movement of the first engagement member is linear, and wherein the first engagement member and the third engagement member engage in a non-detained fashion.

3. The computer-assisted device of claim 1, wherein the control unit is further configured to: in response to detecting engagement of the first engagement member with the third engagement member and detecting engagement of the second engagement member with the fourth engagement member, control movement of the end effector along the degree of freedom by controlling driving of the first and second engagement members.

4. The computer-assisted device of claim 1, wherein actuation of the first and second actuators is concurrent until at least the engagement between the first engagement member and the third engagement member is detected.

5. The computer-assisted device of claim 1, wherein the control unit is further configured to servo the first actuator to a constant commanded position after a detection of the engagement of the first engagement member with the third engagement member and before a detection of engagement of the second engagement member with the fourth engagement member.

6. The computer-assisted device of claim 1, wherein the control unit is further configured to continue actuation of the first actuator after detection of the engagement of the first engagement member with the third engagement member and before detection of engagement of the second engagement member with the fourth engagement member.

7. The computer-assisted device of claim 1, wherein the control unit is further configured to: in response to both detecting engagement of the first engagement member with the third engagement member and detecting engagement of the second engagement member with the fourth engagement member, actuate the first actuator to a first actuation threshold.

8. The computer-assisted device of claim 1, wherein the control unit is further configured to detect engagement of the first engagement member with the third engagement member based on an estimate of a force or torque associated with engagement between the first engagement member and the third engagement member.

9. The computer-assisted device of claim 8, wherein the control unit is further configured to detect engagement of the first engagement member with the third engagement member based on a temporal, spatial, or frequency pattern in the estimated force or torque.

10. The computer-assisted device of claim 9, wherein the temporal, spatial, or frequency pattern comprises a temporal or spatial increase in a magnitude of the estimated force or torque followed by a decrease in the magnitude of estimated force or torque.

11. The computer-assisted device of claim 9, wherein the temporal, spatial, or frequency pattern comprises a frequency spectrum corresponding to contact of the first engagement member with the third engagement member.

12. The computer-assisted device of claim 1, wherein the control unit is further configured to detect engagement of the first engagement member with the third engagement member based on a position error of the first actuator or a speed change in the first actuator.

13. The computer-assisted device of claim 1, wherein the control unit is further configured to: in response to detecting engagement of the second engagement member with the fourth engagement member, confirm engagement of the first engagement member with the third engagement member and the second engagement member with the fourth engagement member.

14. The computer-assisted device of claim 13, wherein to confirm engagement of the first engagement member with the third engagement member and the second engagement member with the fourth engagement member, the control unit is configured to:
confirm movement of the end effector with respect to the degree of freedom in response to actuating the first actuator at a first force or torque and actuating the second actuator at a second force or torque; or
detect a change in one or more of a force, a torque, a position error, or a speed associated with each of the first and second engagement members in response to actuating the first and second actuators.

15. The computer-assisted device of claim 13, wherein the control unit is further configured to, in response to detecting engagement of the second engagement member with the fourth engagement member:
actuate the first actuator to drive the first engagement member to cause movement of the end effector in the first direction of the degree of freedom to a first detectable position;
actuate the second actuator to drive the second engagement member to cause movement of the end effector in the second direction of the degree of freedom to a second detectable position; and
actuate at least one of the first actuator or the second actuator to cause movement of the end effector to a home position between the first detectable position and the second detectable position that is determined based on the first detectable position and the second detectable position.

16. The computer-assisted device of claim 1, further comprising:
a fifth engagement member;
wherein the engagement mode is entered when the control unit detects engagement between the fifth engagement member and a sixth engagement member at a proximal end of the instrument.

17. The computer-assisted device of claim 1, further comprising:
a fifth engagement member;
wherein the movement of the first engagement member or the movement of the first engagement member and the second engagement member causes engagement between the fifth engagement member and a sixth engagement member at a proximal end of the instrument.

18. A method of engaging a drive unit with an instrument, the method comprising:
actuating a first actuator of the drive unit to drive a first engagement member;
detecting engagement of the first engagement member with a third engagement member of the instrument, where actuation of the third engagement member causes a movement of an end effector of the instrument in a first direction of a degree of freedom;
actuating a second actuator of the drive unit to drive a second engagement member;
detecting engagement of the second engagement member with a fourth engagement member of the instrument, where actuation of the fourth engagement member causes a movement of the end effector in a second direction of the degree of freedom, the second direction being opposite the first direction;
in response to detecting engagement of the first engagement member with the third engagement member and detecting engagement of the second engagement member with the fourth engagement member, actuating the first and second actuators such that a force or torque experienced by the first engagement member reaches a preset level; and
actuating the first and second actuators to cause movement of the end effector along the degree of freedom while maintaining the force or torque experienced by the first engagement member at or below the preset level.

19. The method of claim 18, wherein the first engagement member is driven linearly, wherein the first engagement member and the third engagement member engage in a non-detained fashion, and wherein the third engagement member and the fourth engagement member control movement of the end effector with respect to the degree of freedom in an antagonistic fashion.

20. The method of claim 18, wherein:
actuating of the first and second actuators is concurrent until at least the engagement between the first engagement member and the third engagement member is detected; or
the method further comprises: servoing the first actuator to a constant commanded position after detecting engagement of the first engagement member with the third engagement member and before detecting engagement of the second engagement member with the fourth engagement member; or
the method further comprises: continuing actuation of the first actuator after detecting engagement of the first engagement member with the third engagement member and before detecting engagement of the second engagement member with the fourth engagement member.

21. The method of claim 18, further comprising: in response to both detecting engagement of the first engagement member with the third engagement member and detecting engagement of the second engagement member with the fourth engagement member, actuating the first actuator to a first actuation threshold.

* * * * *